United States Patent [19]

Yurugi et al.

[11] Patent Number: 5,783,678
[45] Date of Patent: Jul. 21, 1998

[54] ACRYLIC ESTER DERIVATIVE AND PRODUCING OF THE SAME AND ACRYLIC-ESTER-BASED POLYMER

[75] Inventors: Keiji Yurugi; Koichi Nakagawa; Hideaki Nagano, all of Himeji; Yuichi Kita, Akashi, all of Japan

[73] Assignee: Nippon Shokubai Co., Ltd., Osaka, Japan

[21] Appl. No.: 617,586

[22] Filed: Mar. 19, 1996

[30] Foreign Application Priority Data

Mar. 24, 1995 [JP] Japan .................. 7-066300
Mar. 24, 1995 [JP] Japan .................. 7-066306

[51] Int. Cl.⁶ .................................................. C07H 15/10
[52] U.S. Cl. ............................................................ 536/18.2
[58] Field of Search ............................................... 536/18.2

[56] References Cited

U.S. PATENT DOCUMENTS 3,225,012 12/1965 Black et al. .................. 260/78
3,356,652 12/1967 Ray-Chaudhuri ........... 260/78.4

FOREIGN PATENT DOCUMENTS 54-163981 A 12/1979 Japan .
56-5137 A 1/1981 Japan .
56-76419 A 6/1981 Japan .
57-42641 B2 9/1982 Japan .
60-106802 A 6/1985 Japan .
60-192704 A 10/1985 Japan .
2-275892 A 11/1990 Japan .

*Primary Examiner*—Joseph L. Schofer
*Assistant Examiner*—Wu C. Cheng
*Attorney, Agent, or Firm*—Kubovcik & Kubovcik

[57] ABSTRACT

An acrylic ester derivative expressed by Formula (1) below is produced by reacting an acrylic ester expressed by Formula (2) below with a saccharide containing a hemiacetal hydroxyl group expressed by Formula (3) below and/or an alkylglycoside expressed by Formula (4) below:

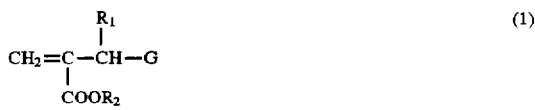

where $R_1$ represents a hydrogen atom or organic residue, $R_2$ represents a hydrogen atom, counter ion, or organic residue, and G represents a saccharic residue;

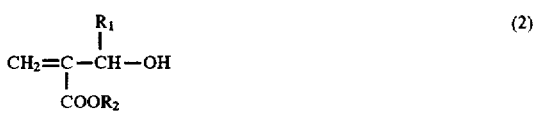

where $R_1$ represents a hydrogen atom or organic residue and $R_2$ represents a hydrogen atom, a counter ion, or organic residue;

$$G-H \quad (3)$$

where G represents a saccharic residue; and $$G-R_3 \quad (4)$$

where G represents a saccharic residue and $R_3$ represents an organic residue. An acrylic-ester-based polymer is produced by letting a monomeric component containing such an acrylic ester derivative undergo polymerization. The resulting acrylic-ester-based polymer renders excellent hydrophilic property, biodegradability, and bioadaptability, and therefore, can be preferably used as a surface finishing agent, a medical material, a water absorptive resin, a surfactant, etc.

6 Claims, 16 Drawing Sheets

ACRYLIC ESTER DERIVATIVE AND PRODUCING OF THE SAME AND ACRYLIC-ESTER-BASED POLYMER

FIELD OF THE INVENTION

The present invention relates to a new acrylic ester derivative and a producing process of the same and to an acrylic-ester-based polymer, and more particularly, to an acrylic-ester-based polymer rendering excellent hydrophilic property, biodegradability, and bioadaptability, and to a new acrylic ester derivative utilized for synthesizing such an acrylic-ester-based polymer and a producing process of the same. A crosslinked product of the above acrylic-ester-based polymer renders excellent water absorption power, and therefore, can be preferably used as a water absorptive resin.

BACKGROUND OF THE INVENTION

It is known that a polymer containing saccharic residues at side chains renders excellent hydrophilic property and bioadaptability. Thus, such a polymer has been used in various forms including a surface finishing agent, medical materials, etc. An example polymer containing saccharic residues is disclosed in Japanese Patent Official Gazette No. Showa 60-106802 and Japanese Patent Official Gazette No. Showa 60-192704. More precisely, a polymer disclosed herein is produced by the steps of: (1) hydroxymethylating polystyrene, (2) attaching a saccharide whose hydroxyl groups are protected by protective groups, such as acetyl groups and halogen atoms, to the product produced in the first step, and (3) saponifying the protective groups of the saccharide using an alkali.

Another example polymer is disclosed in U.S. Pat. No. 3,225,012, U.S. Pat. No. 3,356,652, and Japanese Examined Patent Publication No. Showa 57-42641. More precisely, a polymer disclosed herein is produced by the steps of: (1) attaching a saccharide whose hydroxyl groups are protected by protective groups, such as acetyl groups and isopropylidene groups, to an olefin-based monomer, and (2) removing the protective groups of the saccharide after the product produced in the first step is polymerized.

However, these polymers have a problem that the protective groups of the saccharic residues are not removed completely, thereby rendering unsatisfactory hydrophilic property and bioadaptability. Also, in some cases, there occurs a problem that the saccharic residues are not attached uniformally, or an alkali or acid used to remove the protective groups degrades the quality of the resulting polymer. In addition, when the protective groups are removed from the hydroxyl groups, the polymer increases affinity to water and turns into a high-viscous water solution or gel, thereby making neutralization using an alkali or acid and ensuing desalination impossible.

To solve these problems, a polymer containing protective-group-free saccharic residues at side chains is proposed in Japanese Patent Official Gazette No. Heisei 2-275892. Herein, saccharic residues are attached to carboxyl groups in a polymer of (meta)acarylic acid as side chains through ester linkage.

With such a polymer, however, the ester linkage may be hydrolyzed in the presence of a base and the saccharic residues may be released from the side chains. In view of the foregoing, there is a need for a new polymer containing saccharic residues that are not released from the side chains by hydrolysis or the like.

Incidentally, the use of water absorptive resins is not limited to sanitary materials, such as paper diapers and sanitary items, and they are now used in many ways in various fields: a body fluid absorber in the medical industry, a sealing material (water stopping material) or dewing inhibitor in the civil engineering and construction industry, a freshness preserver in the food industry, a dehydrating material for removing water from a solvent in the manufacturing industry, a planting material in the agricultural and gardening industry, etc. Accordingly, the water absorptive resins for a specific use have been developed in each field.

Of all the available water absorptive resins, a compound based on polyacrylic acid(salt) is preferred due to its excellent water absorption power and low price. However, a water absorptive resin based on polyacrylic acid(salt) renders only a slight photodegrability when it has absorbed water and substantially no biodegrability. This means that when such a water absorptive resin is disposed, for example, buried in soil, it is not decomposed by bacteria and microbes, thereby posing an environmental problem.

On the other hand, natural products, such as cellulose including a pulp or paper, starch, carboxymethyl cellulose salt, are known as a biodegradable water absorptive material. However, such a natural water absorptive material uses a capillary phenomenon with respect to water or an increase in viscosity caused by absorbing water. Thus, when an external pressure is applied to the natural water absorptive material, the water absorption power decreases.

To solve these problems, a polysaccharide has been graft polymerized or crosslinked experimentally to produce a biodegradable water absorptive resin having excellent water absorption power. For example, Japanese Patent Official Gazette No. Showa 56-76419 discloses a process for graft polymerizing a polysaccharide with a hydrophilic monomer. Also, Japanese Patent Official Gazette No. Showa 56-5137 discloses a process for crosslinking a polysaccharide, and Japanese Patent Official Gazette No. Showa 54-163981 discloses a process for crosslinking a polysaccharide, namely, a cellulose derivative.

However, the water absorptive resins produced out of a polysaccharide by the processes of the above three gazettes are inferior to the raw material in biodegrability, and the biodegrability can be enhanced only by sacrificing the water absorption power. In addition, since the raw material is a natural product, the quality and a stable supply of the same are not ensured. Thus, these three processes are not suitable for a mass production of water absorptive resins.

In view of the foregoing, there is an increasing need for a water absorptive resin whose water absorption power is as excellent as a water absorptive resin based on polyacrylic acid(salt), and whose biodegrability is at least as good as the natural counterparts. In other words, there is an increasing need for a water absorptive resin made of a synthetic polymer.

SUMMARY OF THE INVENTION

It is therefore an object of the present invention to provide a multi-purpose new acrylic ester derivative containing a saccharic residue and a producing process of the same and to provide an acrylic-ester-based polymer. To be more specific, the present invention has a first object to provide an acrylic-ester-based polymer rendering excellent hydrophilic property, biodegrability, and bioadaptability, and a new acrylic ester derivative utilized for synthesizing such an acrylic-ester-based polymer and a producing process of the same.

When an acrylic ester derivative contains a great amount of compounds having more than one double bond within a single molecule as impurities, it is confirmed that the acrylic ester derivative turns into gel during polymerization, thereby making it impossible to produce a desired acrylic-ester-based polymer. Also, when an acrylic ester derivative includes colored compounds as impurities, it is confirmed that the acrylic ester derivative and a polymer based on the same show some color as well. Thus, the present invention has a second object to provide a process of producing a desired acrylic ester derivative, that is to say, a highly pure new acrylic ester derivative of the present invention.

The inventors of the present invention repetitively performed experiments on an acrylic-ester-based polymer whose saccharic residues are not released from side chains by hydrolysis or the like, and succeeded in producing (1) a new acrylic-ester-based polymer containing saccharic residues at side chains other than those of the carboxyl groups, and (2) a new acrylic ester derivative utilized for synthesizing the above acrylic-ester-based polymer.

To fulfill the first object, a process of producing an acrylic ester derivative of the present invention expressed by Formula (1) below is characterized by reacting an acrylic ester expressed by Formula (2) below with a saccharide containing a hemiacetal hydroxyl group expressed by Formula (3) below and/or an alkylglycoside expressed by Formula (4) below:

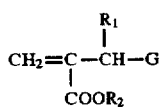

(1)

where $R_1$ represents a hydrogen atom or organic residue, $R_2$ represents a hydrogen atom, counter ion, or organic residue, and G represents a saccharic residue;

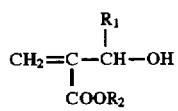

(2)

where $R_1$ represents a hydrogen atom or organic residue and $R_2$ represents a hydrogen atom, counter ion, or organic residue;

(3)

where G represents a saccharic residue; and

(4)

where G represents a saccharic residue and $R_3$ represents an organic residue.

An acrylic-ester-based polymer of the present invention is characterized in that it has a structure unit expressed by Formula (5) below and a number average molecular amount in a range between 1,000 and 2,000,000:

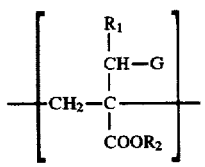

(5)

where $R_1$ represents a hydrogen atom or organic residue, $R_2$ represents a hydrogen atom, counter ion, or organic residue, and G represents a saccharic residue.

Saccharic residues are attached to side chains in the above acrylic ester derivative and acrylic-ester-based polymer without using ester linkage, thereby making the linkage highly resistant to hydrolysis. To be more specific, the linkage of the saccharic residues is not hydrolyzed even in the presence of a base, and the saccharic residues are not released from the side chains. Hence, the above acrylic-ester-based polymer contains the saccharic residues at side chains in a stable manner. In addition, the saccharic residues are attached to the side chains in the same manner as seen in organisms or nature (glycoside linkage or the like), meaning that the above acrylic-ester-based polymer renders excellent biodegrability and bioadaptability.

Thus, the above acrylic-ester-based polymer renders excellent hydrophilic property, biodegrability, and bioadaptability, and can be used in various fields as a surface finishing agent, a medical material, a water absorptive resin, a surfactant, etc. A crosslinked product of such an acrylic-ester-based polymer particularly renders excellent water absorption power, and therefore, can be preferably used as a water absorptive resin. Also, an acrylic ester derivative utilized for synthesizing the above acrylic-ester-based polymer can be readily produced by the above producing process.

For a fuller understanding of the nature and advantages of the invention, reference should be made to the ensuing detailed description taken in conjunction with the accompanying drawings.

DESCRIPTION OF EMBODIMENT

Figure 1:
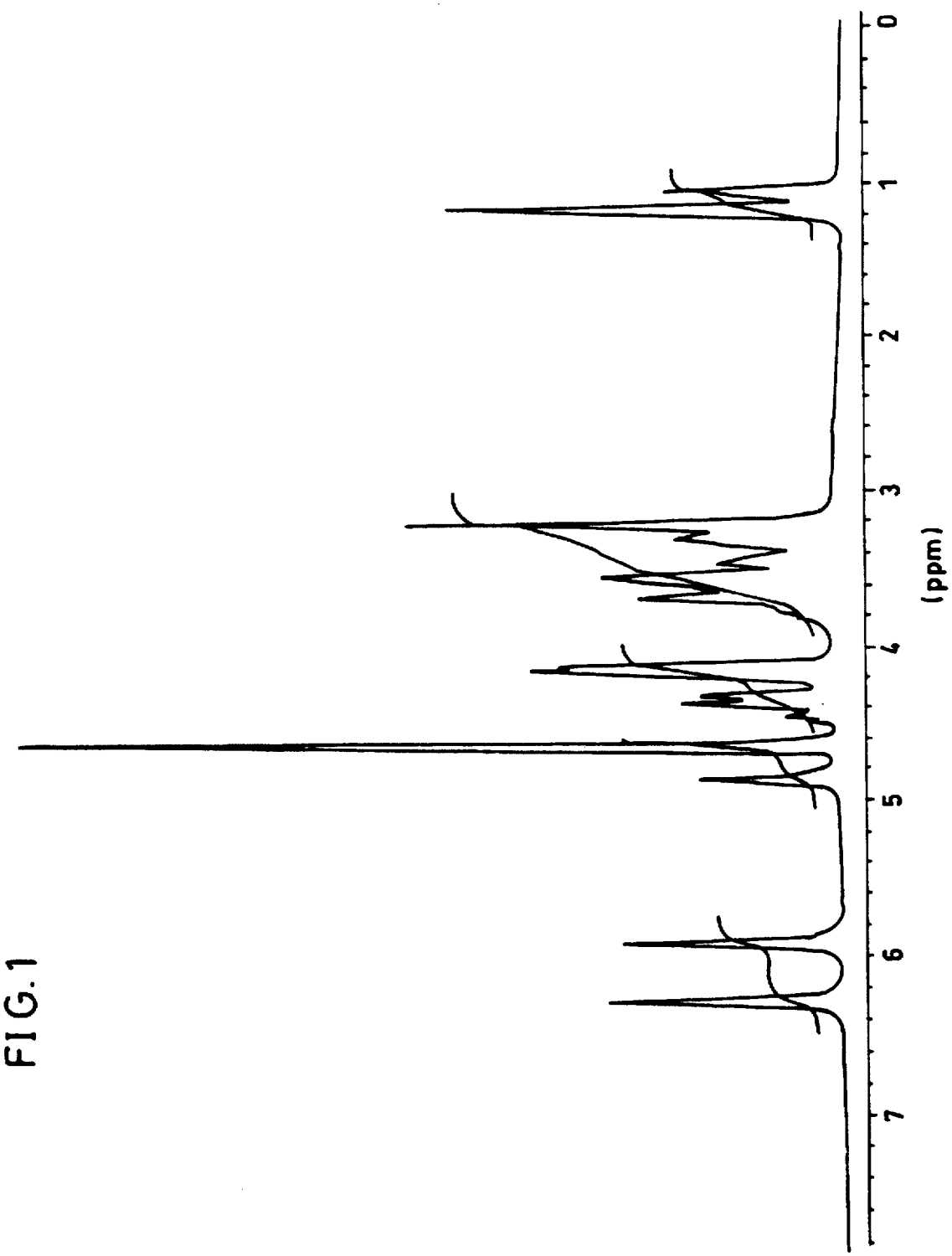
FIG. 1 is an $^1$H-NMR chart of a reaction product obtained in EXAMPLE 1 of the present invention.

The present invention relates to an acrylic ester derivative expressed by:

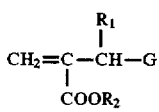

where $R_1$ represents a hydrogen atom or organic residue, $R_2$ represents a hydrogen atom, counter ion, or organic residue, and G represents a saccharic residue.

The present invention also relates to an acrylic ester derivative expressed by Formula (1) above, where $R_1$ represents a hydrogen atom and $R_2$ represents a hydrogen atom, alkaline metal, alkaline earth metal, or alkyl group having up to eight carbon atoms.

Further, the present invention relates to a producing process of an acrylic ester derivative expressed by Formula (1) above characterized by reacting an acrylic ester expressed by Formula (2) below with a saccharide containing a hemiacetal hydroxyl group expressed by Formula (3) below and/or an alkylglycoside expressed by Formula (4) below:

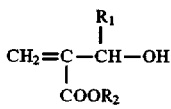

where $R_1$ represents a hydrogen atom or organic residue and $R_2$ represents a hydrogen atom, counter ion, or organic residue;

       (3)

where G represents a saccharic residue; and

       (4)

where G represents a saccharic residue and $R_3$ represents an organic residue.

Still, the present invention relates to an acrylic-ester-based polymer having a number average molecular weight of 1,000–2,000,000, whose structure unit is expressed by:

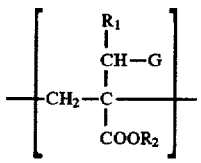

where $R_1$ represents a hydrogen atom or organic residue, $R_2$ represents a hydrogen atom, counter ion, or organic residue, and G represents a saccharic residue.

The following description will describe the present invention more in detail.

An acrylic ester derivative of the present invention expressed by Formula (1) above is, but not limited to, a compound whose substitutional group represented by $R_1$ is a hydrogen atom or organic residue, whose substitutional group represented by $R_2$ is a hydrogen atom, counter ion, or organic residue, and whose substitutional group represented by G is a saccharic residue. A compound whose substitutional group represented by $R_1$ is a hydrogen atom and whose substitutional group represented by $R_2$ is a hydrogen atom, alkaline metal, alkaline earth metal, or alkyl group having up to eight carbon atoms is more preferable.

An acrylic-ester-based polymer of the present invention whose structure unit is expressed by Formula (5) above is, but not limited to, a polymer whose substitutional group represented by $R_1$ is a hydrogen atom or organic residue, whose substitutional group represented by $R_2$ is a hydrogen atom, counter ion, or organic residue, and whose substitutional group represented by G is a saccharic residue. The number average molecular weight (Mn) of the acrylic-ester-based polymer is in a range between 1,000 and 2,000,000. An acrylic-ester-based polymer whose number average molecular weight is in a range between 5,000 and 1,500,000 is particularly useful because it is readily produced by normal radical polymerization, besides it is easy to handle.

To be more specific, the organic residue referred to as the substitutional group represented by either $R_1$ or $R_2$ includes: a straight-chain, branched chain, or cyclic alkyl group having up to eighteen carbon atoms; a hydroxyalkyl group having up to eight carbon atoms; an alkoxylalkyl group having two to twenty carbon atoms; an alkyl halide group having up to eight carbon atoms; and an aryl group. Examples of the alkyl halide group are a chlorinated alkyl group, a brominated alkyl group, and a fluorinated alkyl group.

Of all these organic residues, a methyl group, an ethyl group, and an aryl group including a phenyl group are particularly preferred as the substitutional group represented by $R_1$. Also, an alkyl group having up to eight carbon atoms (for example, a methyl group, an ethyl group, an n-propyl group, an isopropyl group, an n-butyl group, an isobutyl group, a t-butyl group, a pentyl group, a hexyl group, a 2-ethylhexyl group, a cyclohexyl group, etc.) and an aryl group including a phenyl group are particularly preferable for the substitutional group represented by $R_2$.

Examples of the counter ion referred to as the substitutional group represented by $R_2$ include, but are not limited to, ions of: alkaline metals, such as lithium, sodium, potassium, and caesium; alkaline earth metals, such as magnesium, calcium, strontium, and barium; transition metals, such as zinc, nickel, tin, lead, and silver; and ammonium compounds, such as ammonia, monomethylamine, dimethylamine, trimethylamine, and triethylamine. Of all these counter ions, ions of alkaline metals, alkaline earth metals, and ammonium compounds, are preferred, and, in particular, sodium, potassium, magnesium, calcium, etc. are preferred. Ions of ammonium compounds referred herein (referred to as ammonium groups, hereinafter) are quaternary compounds derived from ammonium compounds by adding cations, such as protons.

The substitutional group represented by G includes a group derived from any saccharide containing a hemiacetal hydroxyl group at the terminal end of the basic structure of monosaccharides, oligosaccharides, and polysaccharides by removing one hydrogen atom from the hydroxyl group at the position 1, or a group derived from any saccharide having a glycoside linkage with alkyl groups by removing one alkyl group from the acetal group at the position 1. Note that hydroxyl groups other than the hydroxyl group (or acetal group) at the position 1 of the above saccharides may be protected, either entirely or partially, through ester linkage of an acetyl group, acetal linkage of an isopropylidene group, a halogen atom of a bromo group, etc.

Preferred as the substitutional group represented by $R_3$ in Formula (4) above is, but not limited to, an alkyl group having up to five carbon atoms (for example, a methyl group, an ethyl group, an n-propyl group, an isopropyl group, an n-butyl group, an isobutyl group, a t-butyl group, etc.).

Examples of the monosaccharide are: hexoses, such as glucose, galactose, mannose, glucosamine, galactosamine, mannosamine, N-acetylglucosamine, N-acetylgalactosamine, and N-acetylmannosamine; pentoses, such as xylose, ribose, and arabinose; etc.

Examples of the oligosaccharide are disaccharides, such as maltose, lactose, cellobiose, trehalose, isomaltose, gentiobiose, melibiose, laminaribiose, chitobiose, xylobiose, mannobiose, and sophorose; trisaccharides, such as maltotriose, isomaltotriose, mannotriose, and manninotriose; tetrasaccharides, such as maltotetraose; pentasaccharides, such as maltopentaose; etc. Examples of the polysaccharide are cellulose, amylose (starch), chitin, chitosan, etc.

Of all these saccharides, glucose, galactose, mannose, glucosamine, galactosamine, N.-acetylglucosamine, maltose, lactose maltotriose, cellulose, amylose, chitin, and chitosan are particularly preferred. One or more than one of these saccharides are used.

Therefore, the most preferable acrylic ester derivative expressed by Formula (1) above is a compound whose substitutional group represented by $R_1$ is a hydrogen atom, whose substitutional group represented by $R_2$ is an alkyl group having up to eight carbon atoms, a hydrogen atom or sodium, and whose substitutional group represented by G is a residue of at least one saccharide selected from a group consisting of glucose, galactose, mannose, N-acetylglucosamine, maltose, lactose, maltotriose, and amylose.

To be more specific, examples of such a compound are:

methyl-α-(glucosidemethyl)acrylate, methyl-α-(galactosidemethyl)acrylate, methyl-α-(mannosidemethyl)acrylate, methyl-α-(2-acetamide-2-deoxyglucosidemethyl)acrylate, methyl-α-(maltosidemethyl)acrylate, methyl-α-(lactosidemethyl)acrylate, methyl-α-(maltotriosidemethyl)acrylate, methyl-α-(amilosidemethyl)acrylate;

ethyl-α-(glucosidemethyl)acrylate, ethyl-α-(galactosidemethyl)acrylate, ethyl-α-(mannosidemethyl)acrylate, ethyl-α-(2-acetamide-2-deoxyglucosidemethyl)acrylate, ethyl-α-(maltosidemethyl)acrylate, ethy-α-(lactosidemethyl)acrylate, ethyl-α-(maltotriosidemethyl)acrylate, ethyl-α-(amilosidemethyl)acrylate;

n-propyl-α-(glucosidemethyl)acrylate, n-propyl-α-(galactosidemethyl)acrylate, n-propyl-α-(mannosidemethyl)acrylate, n-propyl-α-(2-acetamide-2-deoxyglucosidemethyl)acrylate, n-propyl-α-(maltosidemethyl)acrylate, n-propyl-α-(lactosidemetyl)acrylate, n-propyl-α-(maltotriosidemethyl)acrylate, n-propyl-α-(amilosidemethyl)acrylate;

isopropyl-α-(glucosidemethyl)acrylate, isopropyl-α-(galactosidemethyl)acrylate, isopropyl-α-(mannosidemethyl)acrylate, isopropyl-α-(2-acetamide-2-deoxyglucosidemethyl)acrylate, isopropyl-α-(maltosidemethyl)acrylate, isopropyl-α-(lactosidemethyl)acrylate, isopropyl-α-(maltotriosidemethyl)acrylate, isopropyl-α-(amilosidemethyl)acrylate;

n-butyl-α-(glucosidemethyl)acrylate, n-butyl-α-(galactosidemethyl)acrylate, n-butyl-α-(mannosidemethyl)acrylate, n-butyl-α-(2-acetamide-2-deoxyglucosidemethyl)acrylate, n-butyl-α-(maltosidemethyl)acrylate, n-butyl-α-(lactosidemethyl)acrylate, n-butyl-α-(maltotriosidemethyl)acrylate, n-butyl-α-(amilosidemethyl)acrylate;

isobutyl-α-(glucosidemethyl)acrylate, isobutyl-α-(galactosidemethyl)acrylate, isobutyl-α-(mannosidemethyl)acrylate, isobutyl-α-(2-acetamide-2-deoxyglucosidemethyl )acrylate, isobutyl-α-(maltosidemethyl)acrylate, isobutyl-α-(lactosidemethyl)acrylate, isobutyl-α-(maltotriosidemethyl)acrylate, isobuty-α-(amilosidemethyl)acrylate;

t-butyl-α-(glucosidemethyl)acrylate, t-butyl-α-(galactosidemethyl)acrylate, t-butyl-α-(mannosidemethyl)acrylate, t-butyl-α-(2-acetamide-2-deoxyglucosidemethyl)acrylate, t-butyl-α-(maltosidemethyl)acrylate, t-butyl-α-(lactosidemethyl)acrylate, t-butyl-α-(maltotriosidemethyl)acrylate, t-butyl-α-(amilosidemethyl)acrylate;

pentyl-α-(glucosidemethyl)acrylate, pentyl-α-(galactosidemethyl)acrylate, pentyl-α-(mannosidemethyl)acrylate, pentyl-α-(2-acetamide-2-deoxyglucosidemethyl)acrylate, pentyl-α-(maltosidemethyl)acrylate, pentyl-α-(lactosidemethyl)acrylate, pentyl-α-(maltotriosidemethyl)acrylate, pentyl-α-(amilosidemethyl)acrylate;

hexyl-α-(glucosidemethyl)acrylate, hexyl-α-(galactosidemethyl)acrylate, hexylα-(mannosidemethyl)acrylate, hexyl-α-(2-acetamide-2-deoxyglucosidemethyl)acrylate, hexyl-α-(maltosidemethyl)acrylate, hexyl-α-(lactosidemethyl)acrylate, hexyl-α-(maltotriosidemethyl)acrylate, hexyl-α-(amilosidemethyl)acrylate;

2-ethylhexyl-α-(glucosidemethyl)acrylate, 2-ethylhexyl-α-(galactosidemethyl)acrylate, 2-ethylhexyl-α-(mannosidemethyl)acrylate, 2-ethylhexyl-α-(2-acetamide-2-deoxyglucosidemethyl)acrylate, 2-ethylhexyl-α-(maltosidemethyl)acrylate, 2-ethylhexyl-α-(lactosidemethyl)acrylate, 2-ethylhexyl-α-(maltotriosidemethyl)acrylate, 2-ethylhexyl-α-(amilosidemethyl)acrylate;

cyclohexyl-α-(glucosidemethyl)acrylate, cyclohexyl-α-(galactosidemethyl)acrylate, cyclohexyl-α-(mannosidemethyl)acrylate, cyclohexyl-α-(2-acetamide-2-deoxyglucosidemethyl)acrylate, cyclohexyl-α-(maltosidemethyl)acrylate, cyclohexyl-α-(lactosidemethyl)acrylate, cyclohexyl-α-(maltotriosidemethyl)acrylate, cyclohexyl-α-(amilosidemethyl)acrylate;

α-(glucosidemethyl)acrylate, α-(galactosidemethyl)acrylate, α-(mannosidemethyl)acrylate, α-(2-acetamide-2-deoxyglucosidemethyl)acrylate, α-(maltosidemethyl)acrylate, α-(lactosidemethyl)acrylate, α-(maltotriosidemethyl)acrylate,α-(amilosidemethyl)acrylate;

sodium-α-(glucosidemethyl)acrylate, sodium-α-(galactosidemethyl)acrylate, sodium-α-(mannosidemethyl)acrylate, sodium-α-(2-acetamide-2-deoxyglucosidemethyl)acrylate, sodium-α-(maltosidemethyl)acrylate, sodium-α-(lactosidemethyl)acrylate, sodium-α-(maltotriosidemethyl)acrylate, sodium-α-(amilosidemethyl ) acrylate; etc.

The acrylic ester derivative of the present invention can be readily produced by, in the presence of a catalyst, an acetalization reaction of an acrylic ester expressed by Formula (2) above with any saccharide containing a hemiacetal hydroxyl group at the terminal end expressed by Formula (3) above, and/or an acetal exchange reaction of an acrylic ester expressed by Formula (2) above with an alkylglycoside expressed by Formula (4) above, namely, any saccharide having glycoside linkage with an alkyl group.

In other words, an acrylic ester derivative expressed by Formula (1) above can be readily produced by, for example, reacting an acrylic ester expressed by Formula (2) above with a saccharide expressed by Formula (3) above in the presence of a catalyst. Also, an acrylic ester derivative expressed by Formula (1) above can be readily produced by, for example, reacting an acrylic ester expressed by Formula (2) above with an alkylglycoside expressed by Formula (4) above in the presence of a catalyst.

An acrylic ester expressed by Formula (2) above includes, but is not limited to, alkyl-α-hydroxyalkylester acrylate, and examples of which are: alkyl-α-hydroxyalkylacrylates, such as methyl-α-hydroxymethylacrylate, ethyl-α-hydroxymethylacrylate, n-propyl-α-hydroxymethylacrylate, isopropyl-α-hydroxymethylacrylate, n-butyl-α-hydroxymethylacrylate, isobutyl-α-hydroxymethylacrylate, t-butyl-α-hydroxymethylacrylate, pentyl-α-hydroxymethylacrylate, hexyl-α-hydroxymethylacrylate, 2-ethylhexyl-α-hydroxymethylacrylate, methyl-α-(1-hydroxyethyl)acrylate, ethyl-α-(1-hydroxyethyl)acrylate, n-butyl-α-(1-hydroxyethyl)acrylate, and 2-ethylhexyl-α-(1-hydroxyethyl)acrylate; α-hydroxymethylacrylate, α-hydroxymethylsodium acrylate; etc. One or more than one of these acrylic esters are used as occasion demands.

A producing process of the above acrylic esters is not especially limited. Any of the above acrylic esters is readily produced by a known method, for example, by reacting an adequate acrylate compound with an adequate aldehyde compound in the presence of a catalyst, such as a basic ion exchange resin, which is disclosed in, for example, Japanese Official Patent Gazette No. Heisei 6-135896.

Examples of the saccharide containing a hemiacetal hydroxyl group expressed by Formula (3) above include, but are not limited to, the above-mentioned saccharides, namely, all saccharides containing a hemiacetal hydroxyl group at the terminal end of the basic structure of monosaccharides, oligosaccharides, or polysaccharides. One or more than one of these saccharides are used as occasion demands.

Examples of the alkylglycoside expressed by Formula (4) above include, but are not limited to: methylglucoside, methylgalactoside, methylmannoside, methyl-N-acetylglucoside, methylmaltoside, methyllactoside, methylmaltotrioside, methylamiloside, methylxyloside; ethylglucoside, ethylgalactoside, ethylmannoside, ethylxyloside; n-propylglucoside, isopropylglucoside, n-butylglucoside, n-butylgalactoside, n-butylmannoside, n-butylxyloside; etc. One or more than one of these alkylglycosides are used as occasion demands.

An adding amount of a saccharide expressed by Formula (3) above and/or an alkylglycoside expressed by Formula (4) above with respect to an amount of an acrylic ester is not especially limited. However, a preferable adding amount to 1 mole of an acrylic ester is in a range between 0.01 mole and 10 mole. A range between 0.02 mole and 5 mole is more preferable, a range between 0.03 mole and 2 mole is further preferable, and a range between 0.05 mole and 1 mole is most preferable.

Acid catalysts are preferred as the catalyst used herein, and examples of which are: mineral acids, such as hydrochloric acid, sulfuric acid, phosphoric acid, and boric acid, and partial-neutralized salts of these acids; heteropolyacids, such as tungstophosphoric acid, molybudophosphoric acid, tungstosilicic acid, and molybdosilicic acid, and partial-neutralized salts of these acids; organic sulfonic acids, such as methanesulfonic acid and paratoluenesulfonic acid; protonic acid of organic carbonic acids, such as formic acid, acetic acid, lauric acid, and oleic acid; Lewis acids, such as boron fluoride, boron chloride, aluminium chloride, tin dichloride, and tin tetrachloride; acid ion exchange resins based on either phenol or styrene of a gel, porous, or macroporous type containing at least one ion exchange group selected from a group consisting of a sulfonic acid group and an alkylsulfonic acid group; etc. One or more than one of these catalysts are used. Of all these catalysts, protonic acid is preferred in terms of promoting the reaction of an acrylic ester with a saccharide expressed by Formula (3) above and/or an alkylglycoside expressed by Formula (4) above.

An adding amount of a catalyst with respect to an amount of an acrylic ester varies depending on the kinds of the acrylic ester and catalyst. A preferable adding amount is in a range between 0.001 percent by weight and 20 percent by weight and a range between 0.005 percent by weight and 15 percent by weight is more preferable. A range between 0.01 percent by weight and 10 percent by weight is further preferable and a range between 0.1 percent by weight and 5 percent by weight is most preferable. An adding amount less than 0.001 percent by weight is not preferable because the catalyst does not promote the reaction sufficiently and the reaction takes too long, thereby making efficient production of an acrylic ester derivative impossible. An adding amount more than 20 percent by weight is not preferable either in terms of economy because not all the increased amount of the catalyst is accompanied with further enhancement of catalytic effects, such as saving the reaction time, thereby wasting some of the catalyst.

The conditions for the above reaction are not especially limited. However, note that both the raw material and product, namely, an acrylic ester and an acrylic ester derivative, contain vinyl groups or the like within their molecules, and therefore, they readily polymerize. Thus, when reacting an acrylic ester with a saccharide expressed by Formula (3) above and/or an alkylglycoside expressed by Formula (4) above, it is preferable to add a polymerization inhibitor (oxidation inhibitor) ormolecular oxygens to the reactant to curb the polymerization of the acrylic ester and acrylic ester derivative. Further, it is preferable to add a polymerization inhibitor when the resulting acrylic ester derivative is transported, stored, transferred, or subject to further reaction.

Examples of a preferable combination of polymerization inhibitors are: a first-order oxidation inhibitor alone; a first-order oxidation inhibitor and a second-order oxidation inhibitor; a first-order oxidation inhibitor and a chelating agent; and first-order and second-order oxidation inhibitors and a chelating agent; etc.

Examples of the first-order oxidation inhibitor are a quinone-based first-order oxidation inhibitor, an alkylphenol-based first-order oxidation inhibitor, an amine-based first-order oxidation inhibitor, a first-order oxidation inhibitor based on dithiocarbamate copper, etc. One or more than one of these first-order oxidation inhibitors are used.

More precisely, examples of the quinone-based first-order oxidation inhibitor are hydroquinone, hydroquinone monomethyl ether(methoxyhydroquinone), p-benzoquinone, p-t-butylcatechol, chloranil, 2-t-butylhydroquinone, 2,5-di-t-butylhydroquinone, 2-t-butylmethoxyhydroquinone, etc.

Examples of the alkylphenol-based first-order oxidation inhibitor are 2,6-di-t-butylphenol, 2,4-di-t-butylphenol, 2-t-butyl-4,6-dimethylphenol, 2,6-di-t-butyl-4-methyl phenol, tetrakis[methylene-3-(3',5'-di-t-butyl-4'-hydroxyphenyl)propionate]methane, etc.

Examples of the amine-based first-order oxidation inhibitor are alkylating diphenylamine, phenothiazine, etc.

Examples of the first-order oxidation inhibitor based on dithiocarbamate copper are dimethyldithiocarbamate copper, diethyldithiocarbamate copper, etc.

Of all these first-order oxidation inhibitors, the quinone-based first-order oxidation inhibitor and alkylphenol-based first-order oxidation inhibitor are preferred. In particular, hydroquinone, hydroquinone monomethyl ether, p-benzoquinone, p-t-butylcatechol; 2,6-di-t-butylphenol, 2,4-di-t-butylphenol, 2-t-butyl-4,6-dimethylphenol, 2, 6-di-t-butyl-4-hydroxymethylphenol, and tetrakis[methylene-3-(3',5'-di-t-butyl-4'-hydroxyphenyl) propionate ] methane are preferable.

Examples of the second-order oxidation inhibitor are sulfur-based second-order oxidation inhibitor, phosphorous-based second-order oxidation inhibitor, etc. One or more than one of these second-order oxidation inhibitors are used.

Examples of the sulfur-based second-order oxidation inhibitor are sulfur, dilauryl-3,3'-thiodipropionate, distearyl-3,3'-thiodipropionate, etc.

Examples of the phosphorous-based second-order oxidation inhibitor are tris(isodecyl)phosphite, tris (tridecyl) phosphite, etc.

Of all these second-order oxidation inhibitors, the sulfur-based second-order oxidation inhibitor is preferred.

The polymerization can be curbed more effectively when the first-order and second-order oxidation inhibitors are used together. In this case, an amount of the first-order oxidation inhibitor is reduced.

Examples of the chleating agent include, but are not limited to, ethylenediaminetetraacetic acid, hydroxyethyl-ethylenediaminetriacetic acid, nitrilotriacetic acid, sodium gluconate, 2,2'-oxamidobis[ethyl-3-(3,5-di-t-butyl-4-hydroxyphenyl)propionate], etc. One or more than one of these chleating agents are used.

Of all these chleating agents, ethylenediaminetetraacetic acid, nitrilotriacetic acid, 2,2'-oxamidobis[ethyl-3-(3,5-di-t-butyl-4-hydroxyphenyl) propionate] are preferred.

The polymerization can be curbed more effectively when the first-order oxidation inhibitor and chleating agent are used together. This is because the chleating agent absorbs some impurities, such as metals. Also, an amount of the first-order oxidation inhibitor is reduced.

An adding amount of the polymerization inhibitor, namely, a total amount of the first-order and second-order oxidation inhibitors, with respect to an amount of an acrylic ester varies depending on the kind of the acrylic ester. However, an adding amount in a range between 0.001 percent by weight and 5 percent by weight is preferable. An adding amount in a range between 0.005 percent by weight and 1 percent by weight is more preferable and an adding amount in a range between 0.01 percent by weight and 0.1 percent by weight is most preferable. An adding amount less than 0.001 percent by weight is not preferable because the polymerization can not be curbed in a satisfactory manner. An adding amount more than 5 percent by weight is not preferable either in terms of economy because not all the increased amount of the polymerization inhibitor is accompanied with further enhancement of the polymerization curbing effect, thereby wasting some of the polymerization inhibitor.

In case that the first-order oxidation inhibitor and second-order oxidation inhibitor are used together, an amount of the second-order oxidation inhibitor with respect to an amount of the first-order oxidation inhibitor is in a range between 1 percent by weight and 200 percent by weight.

In case that the polymerization inhibitor includes a chleating agent, a preferable adding amount of the chleating agent with respect to a total amount of the first-order and second-order oxidation inhibitors is in a range between 0.0005 percent by weight and 100 percent by weight. A range between 0.005 percent by weight and 25 percent by weight is more preferable and a range between 0.01 percent by weight and 10 percent by weight is most preferable. Adding a chleating agent can reduce a relative amount of the first-order and second-order oxidation inhibitors. Adding a chleating agent less than 0.0005 percent by weight is not effective, because it is insufficient to realize the expected effect. On the other hand, adding a chleating agent more than 100 percent by weight is not economical because not all the increased amount of the chleating agent is accompanied with further enhancement of the polymerization curbing effect, thereby wasting some of the chleating agent. In addition, adding a chleating agent more than 100 percent by weight does not further reduce an amount of the first-order and second-order oxidation inhibitors.

Air is used as the molecular oxygens.

The above reaction can take place in a solvent or in non-solvent if the acrylic ester is a liquid. Any solvent will do as long as it does not interfere the above reaction. Examples of such a solvent include, but are not limited to: ethers, such as diethylether and diisopropylether; aliphatic hydrocarbons, such as hexane, cyclohexane, and heptane; aromatic hydrocarbons, such as benzene, toluene, and xylene; halogenated hydrocarbons, such as chloroform and chlorobenzene; dimethyl sulfoxide, N,N-dimethylformamide, sulfolane; etc. An organic solvent used for extraction, which will be described below, is also applicable. One or more than one of these solvents are used. An amount of the solvent is not especially limited.

A reaction temperature is not especially limited, but preferably in a range between 0° C. and 200° C., more preferably in a range between 0° C. and 150° C., and most preferably in a range between 30° C. and 120° C. to curb the above polymerization. A reaction temperature below 0° C. is not preferable because the reaction takes too long and an acrylic ester derivative is not produced efficiently. A reaction temperature above 200° C. is not preferable either because the above polymerization can not be curbed. An adequate reaction time to complete the above reaction is determined based on a reaction temperature, the kinds of an acrylic ester, a saccharide expressed by Formula (3) above and/or an alkylglycoside expressed by Formula (4) above, and a catalyst, or a combination and an amount of these elements.

A reaction pressure is not especially limited, and a reaction can takes place under a normal(ambient), vacuumed, or pressurized pressure. When the reaction takes place under a vacuumed pressure, the reactant is heated up to a temperature where an alcohol can be removed.

To further promote the above reaction, it is preferable to remove water and/or a lower alcohol ($R_3OH$, referred to as an alcohol, hereinafter) produced as a result of the reaction from the reactant. A process of removing an alcohol is not especially limited, and an alcohol is removed by, for example, (1) letting the alcohol undergo a reaction under a vacuumed pressure; (2) letting the alcohol undergo azeotropy with an azeotropic solvent; and (3) letting the alcohol undergo a reaction in the presence of a drying agent or the like that absorbs or adsorbs the alcohol. The first and second example processes are preferred in terms of costs and handling facilities. One or more than one of these processes are used.

A preferable azeotropic solvent is an organic solvent that produces an azeotrope mixture with an alcohol in a temperature range between 0° C. and 150° C., more preferably in a range between 30° C. and 120° C. under a normal or vacuumed pressure. Any azeotropic solvent will do as long as it remains inactive to the reaction so as not to disturb the reaction. Examples of the azeotropic solvent are: ethers, such as diethylether and diisopropylether; aromatic hydrocarbons, such as benzene, toluene, and xylene; aliphatic hydrocarbons, such as pentane, hexane, cyclohexane, and heptane; halogenated hydrocarbons, such as chloroform, methylene chloride, 1,2-dichloroethane, and chlorobenzene; etc. One or more than one of these azeotropic solvents are used. An amount of the azeotropic solvent is not especially limited. Note that it is preferable to separate the azeotrope mixture into the azeotropic solvent and an alcohol by a predetermined process. By so doing, the separated and collected azeotropic solvent can be used repetitively in the above reaction.

In particular, it is preferable to remove an alcohol from the reactant in the presence of a polymerization inhibitor in the above reaction. This not only curbs the above polymerization more effectively, but also further promotes the above reaction.

Further, when removing an alcohol from the reactant in the presence of a polymerization inhibitor, it is preferable to carry out three following processes of:

1) adjusting the density of molecular oxygens ($O_2$) in a gaseous phase of the reactant to a predetermined level;

2) adding N-nitrosophenylhydroxylamine salt to the reactant; and 3) introducing molecular nitrogen monoxides (NO) and/or molecular nitrogen dioxides ($NO_2$) to the reactant.

These three processes, each of which can be performed with the others, will be described more in detail.

In the first process above, the density of molecular oxygens of the reactant, namely, the density of molecular oxygens in the gaseous phase of a reactor, is adjusted to a range between 0.1 percent by capacity and 10 percent by capacity. As a result, the polymerization can be curbed more efficiently, and the yield of the objective product, an acrylic ester derivative, can be further increased. If the density of molecular oxygens is below 0.1 percent by capacity, the polymerization of an acrylic ester and an acrylic ester derivative in the gaseous phase may not be curbed. If the density of molecular oxygens is above 10 percent by capacity, an explosive gas mixture may be formed with inflammable elements during the reaction and the safety is not ensured.

A process of adjusting the density of molecular oxygens is not especially limited, and the density of molecular oxygens is adjusted to the above range by, for example, introducing a mixed gas prepared by mixing molecular oxygens and an inert gas, such as a nitrogen gas and an argon gas, into the reactor; or by introducing the molecular oxygens into the reactor until the density of molecular oxygens reaches the above range. A process of introducing the mixed gas or molecular oxygens into the reactor is not especially limited, and it can be performed continuously or intermittently. The molecular oxygens referred herein are, for example, air.

In the second process above, N-nitrosophenylhydroxylamine salt expressed Formula (6) below is added to the reactant:

$$[Ph-N(NO)O]_nM \qquad (6)$$

where Ph represents a phenyl group, n represents a positive integer up to 3, and M represents a metallic atom or ammonium group.

Examples of the metallic atom, or a substitutional group represented by M, include, but are not limited to, alminium, copper iron(III), tin, zinc, magnesium, etc. Of all these metallic atoms, aluminium is particularly preferred. Note that N-nitrosophenylhydroxylamine salt, when decomposed, generates molecular nitrogen monoxides and/or molecular nitrogen dioxides.

Although it depends on the reaction conditions, a preferable adding amount of N-nitrosophenylhydroxylamine salt with respect to an amount of an acrylic ester is in a range between 0.001 percent by weight and 5 percent by weight, more preferably in a range between 0.005 percent by weight and 1 percent by weight, and most preferably in a range between 0.01 percent by weight and 0.5 percent by weight. Adding N-nitrosophenylhydroxylamine salt in the above ranges not only curbs the polymerization more effectively, but also further increases the yield of the objective product, an acrylic ester derivative.

In the third process above, the density of molecular nitrogen monoxides and/or molecular nitrogen dioxides (collectively referred to as nitrogen oxides, hereinafter) of the reactant, namely, the density of nitrogen oxides in the gaseous phase of the reactor, is adjusted to a range between 0.1 percent by capacity and 10 percent by capacity by introducing nitrogen oxides to the reactor. In other words, the above reaction is carried out under atmosphere of nitrogen oxides. Adjusting the density of nitrogen oxides to the above range not only curbs the polymerization more effectively, but also further increases the yield of the objective product, namely, an acrylic ester derivative. When the density of nitrogen oxides is below 0.1 percent by capacity, the polymerization of an acrylic ester and an acrylic ester derivative in the gaseous phase may not be curbed. When the density of nitrogen oxides is above 10 percent by capacity, not all the increased amount in density is accompanied with the further enhancement of the polymerization curbing effect, thereby wasting some of the nitrogen oxides. Thus, it is not economically advantageous.

A process of adjusting the density of nitrogen oxides is not especially limited, and, for example, the density of nitrogen oxides is adjusted to the above range by introducing a mixed gas prepared by mixing nitrogen oxides and an inert gas, such as a nitrogen gas and an argon gas, into the reactor; or nitrogen oxides are introduced to the reactor until the density of nitrogen oxides reaches the above range. A process of introducing the mixed gas or nitrogen oxides into the reactor is not especially limited, and it can be performed either continuously or intermittently.

When the reaction ends, the reactant solution may be neutralized using a neutralizer as occasion demands. Examples of the neutralizer include, but are not limited to, sodium hydroxide, potassium hydroxide, sodium carbonate, potassium carbonate, etc. The neutralizer is used in, for example, a solid state (powders or granules) or liquid state (solution).

The post-reaction reactant solution contains, for example, a catalyst and/or neutralized salts thereof, a slight amount of a by-product, or impurities contained in the raw materials (all of which are collectively referred to as impurities, hereinafter). The impurities generally include two types of compounds: compounds having more than one double bond within a single molecule (which are referred to as crosslinking impurities, hereinafter); and compounds that color an acrylic ester derivative or a polymer based on the same (which are referred to as coloring impurities, hereinafter). When a resulting acrylic ester derivative includes a great amount of crosslinking impurities, the acrylic ester derivative turns into gel during polymerization, thereby making it impossible to produce a desired acrylic-ester-based polymer. Also, when an acrylic ester derivative includes coloring impurities, the acrylic ester derivative and polymer based on the same show some color as well. Note that the crosslinking impurities can be identified, while the coloring impurities can be hardly identified. Examples of the crosslinking impurities are a dimer of an acrylic ester, a dimer generated as a result of a side reaction, a dimer produced as a result of a reaction of the impurities contained in the raw material, etc.

Therefore, to produce a desired acrylic ester derivative, namely, a highly pure new acrylic ester derivative of the present invention, it is preferable to purify the resulting acrylic ester derivative and remove the impurities when the reaction ends.

A purifying process of an acrylic ester derivative is not especially limited. However, the most preferable process is to remove the impurities through extraction by mixing water and an organic solvent immiscible with water with the neutralized and filtered reactant solution when the reaction ends. Since the acrylic ester derivative is soluble to water while the impurities are insoluble to water and soluble to an organic solvent, the acrylic ester derivative moves to the water layer and separated from the impurities contained in the organic solvent layer.

The organic solvent is not especially limited, but must be a compound that does not mix with water (renders immiscibility) and has a dipole moment in a range between 0 and 3, preferably in a range between 0.02 and 2.8, and most preferably in a range between 0.2 and 2.5. An organic solvent whose dipole moment exceeds 3 is not preferable. Because such an organic solvent dissolves a relatively large amount of an acrylic ester derivative and makes the separation from the impurities difficult, thereby reducing the yield of the acrylic ester derivative.

Examples of the organic solvent are aliphatic hydrocarbons, aromatic hydrocarbons, halogenated aliphatic hydrocarbons, halogenated aromatic hydrocarbons, ethers, aliphatic alcohols, aromatic alcohols, esters, acetals, ketones, etc.

Examples of the aliphatic hydrocarbons are pentane, cyclopentane, hexane, cyclohexane, heptane, methylcyclohexane, etc.

Examples of the aromatic hydrocarbons are benzene, toluene, ethylbenzene, xylene, etc.

Examples of the halogenated aliphatic hydrocarbons are dichloromethane, chloroform, carbon tetrachloride, 1,1-dichloroethane, 1,2-dichloroethane, etc.

Examples of the halogenated aromatic hydrocarbons are fluorobenzene, hexaflurorobenzene, fluorotoluene, chlorobenzene, etc.

Examples of the ethers are ethyl ether, n-propyl ether, isopropyl ether, butyl ether, 1,2-dimethoxyethane, tetrahydropyran, etc.

Examples of the aliphatic alcohols are n-butanol, 1-pentanol, 1-hexanol, cyclohexanol, 2-ethyl-l-hexanol, etc.

Examples of the aromatic alcohols are phenol, benzilalcohol, etc.

Examples of the esters are methyl formate, ethyl formate, propyl formate, isopropyl formate, ethyl acetate, propyl acetate, n-butyl acetate, isobutyl acetate, isopentyl acetate, phenyl acetate, ethyl propionate, etc.

Examples of the acetals are methylacetal, ethylacetal, dimethoxy methane, etc.

Examples of the ketones are 2-butanone and the like.

One or more than one of these organic solvents are used as occasion demands. Of all these organic solvents, aliphatic esters are preferred, and in particular, methyl formate, ethyl formate, propyl formate, isopropyl formate, ethyl acetate, propyl acetate, n-butyl acetate, isobutyl acetate, isopentyl acetate, etc. are preferred.

A process of extracting the acrylic ester derivative from the reactant solution by mixing water and organic solvent(s) is not especially limited, and following processes are applicable:

(a) water is added to the reactant solution and mixed together, then an organic solvent is added to the resulting reactant solution and mixed together;

(b) an organic solvent is added to the reactant solution and mixed together, then water is added to the resulting solution and mixed together;

(c) water and an organic solvent are added to the reactant solution at the same time and mixed together;

(d) the reactant solution is added to water and mixed together, and an organic solvent is added to the resulting reactant solution and mixed together;

(e) the reactant solution is added to an organic solvent and mixed together, and water is added to the resulting reactant solution and mixed together; and (f) the reactant solution is added to a mixture of water and an organic solvent and mixed together.

In addition, if an organic solvent is also used as a solvent in the reaction, the followings are applicable:

(g) water is added to the reactant solution and mixed together; and (h) the reactant solution is added to water and mixed together.

These processes can be performed repetitively or more than one of these processes can be performed together. In other words, after the water layer containing the acrylic ester derivative is obtained, an organic solvent is added to the water layer and mixed together to extract the acrylic ester derivative. In this way, the purification precess is performed repetitively.

An amount of water and an organic solvent used in the above purification or extraction process is not especially limited, but it must be sufficient to remove the impurities. To be more specific, as much water as to fully dissolve the acrylic ester derivative contained in the reactant, and as much organic solvent as to extract the impurities from the reactant solution in a satisfactory manner are necessary.

A post-purification acrylic ester derivative is in the form of a solution. Thus, to separate the acrylic ester derivative, water is removed from the resulting solution by vacuum distillation, drying, etc. As a result, the acrylic ester derivative of the present invention can be purified and readily separated from water in a solid or liquid (oil) state. Note that whether separating the acrylic ester derivative from water or not depends on the use thereof. In other words, the acrylic ester derivative is separated only when necessary. The purity, namely, purification degree, of the acrylic ester derivative is not especially limited, and it is also determined depending on the use thereof.

An amount of the crosslinking impurities in the acrylic ester derivative can be found by analyzing the purity of the acrylic ester derivative using, for example, a High-Performance Liquid Chromatography. To be more specific, an amount of the crosslinking impurities (percent by weight) is found by measuring the purity (percent by weight) of the acrylic ester derivative by a 8020-Model of High-Performance Liquid Chromatography (Tosoh Corporation) (referred to as HPLC hereinafter), and substituting the purity into the following equation: amount of crosslinking impurities $\leq$ 100-purity of acrylic ester derivative. For example, if the purity of an acrylic ester derivative is 98 percent by weight, then an amount of the crosslinking impurities is 2 or less percent by weight. However, a process of measuring an amount of the crosslinking impurities is not especially limited.

According to the above purification process, an amount of the crosslinking impurities can be readily reduced to 5 or less percent by weight, and preferably to a range between 0.005 percent by weight and 4 percent by weight, and most preferably to a range between 0.001 percent by weight and 3 percent by weight. Making an amount of the crosslinking impurities 5 or less percent by weight can prevent gelation of the acrylic ester derivative during (co)polymerization. Note that it is extremely difficult and complicated to determine or identify all the impurities in the acrylic ester derivative. Thus, an amount of the crosslinking impurities found by the above inequality is an approximate value.

An approximate amount of the coloring impurities in the acrylic ester derivative can be found by evaluating yellow index (YI) of a 50 wt% water solution of the acrylic ester derivative. The yellow index is evaluated by a method in compliance with JIS K 7103 using a $\Sigma$80-Model of a color-difference meter (Nippon Densyoku Kogyo, Co., Ltd). According to the above purification process, the yellow index can be reduced to 50 or less, and preferably 20 or less.

Since the acrylic ester derivative of the present invention is hardly colored and has satisfactory hue, it renders high commercial values and utilities. Thus, the acrylic ester derivative of the present invention is applicable to diversified fields. A producing process of a 50 wt % acrylic ester derivative water solution is not especially limited. For example, the post-purification acrylic ester derivative water solution may be concentrated, or the separated acrylic ester derivative may be dissolved into pure water.

Alternatively, a highly pure acrylic ester derivative may be produced by the following methods 1) removing the impurities contained in the raw material, namely, an acrylic ester expressed by Formula (2) above, in advance, and 2) separating the reactant solution, when the reaction ends, into the acrylic ester derivative and impurities by the Column Chromatography or the like using silica gel. However, the former is not practical and the latter costs too much and both are economically disadvantageous. Therefore, these two alternative methods are not commercially preferable.

The acrylic ester derivative produced by the above process is readily oxidized by oxygens in the air, which means the quality thereof readily deteriorates. Therefore, when the acrylic ester derivative is transported, stored, or transferred, it is preferable to add the above-mentioned polymerization inhibitor(s) to the acrylic ester derivative, and to adjust the density of molecular oxygens in the gaseous phase having contact with the acrylic ester derivative to a range between 0.1 percent by capacity and 10 percent by capacity, more preferably to a range between 1 percent by capacity and 8 percent by capacity, and most preferably to a range between 2 percent by capacity and 7 percent by capacity. As a result, the acrylic ester derivative is transported, stored, or transferred in a stable manner by curbing polymerization (gelation) or deterioration in quality due to oxidation. Also, the polymerization can be curbed, in other word, the quality of the acrylic ester derivative is secured, even when the acrylic ester derivative is transported, stored, or transferred under sever conditions.

"Being transported" referred herein means, for example, transportation of the acrylic ester derivative by a tank lorry or the like. "Being stored" referred herein means, for example, storage of the acrylic ester derivative in a tank of the like. "Being transferred" referred herein means, for example, transfer of the acrylic ester derivative through pipelines composed of pipes, valves, nozzles, etc. The pipelines referred herein means, for example, a delivery line for delivering the acrylic ester derivative from a storage bath to a polymerization bath or reaction bath. Therefore, "the gaseous phase having contact with the acrylic ester derivative" means a gaseous phase within the tank lorry, tank, pipelines, etc (referred simply as to the gaseous phase, hereinafter).

The state of the acrylic ester derivative at the time of transportation, storage, or transfer (referred collectively to as handling, hereinafter) is not especially limited. For example, the acrylic ester derivative may be a solid, liquid (oil), or water solution, or even the acrylic ester derivative may be dissolved into a solvent.

Any solvent will do as long as it is an inert liquid compound capable of dissolving the acrylic ester derivative, and examples of which include, but are not limited to: alcohols, such as methanol, ethanol, and propanol; ketones, such as acetone and 2-butanone; halogenated hydrocarbons, such as chloroform and methylene chloride; aromatic hydrocarbons, such as benzene, toluene, and xylene; polar solvents, such as dimethyl sulfoxide, N,N-dimethylformamide, and sulfolane; etc. One or more the one of these solvents are used.

A handling temperature of the acrylic ester derivative is not especially limited. When the acrylic ester derivative is a solid or liquid, a preferable handling temperature is in a range between 0° C. and 150° C., more preferably in a range between 0° C. and 100° C., further preferably in a range between 0° C. and 80° C., and most preferably in a range between 0° C. and 60° C. When the acrylic ester derivative is in the form of a water solution or solution, a preferable handling temperature is in a range between 0° C. and 80° C., more preferably in a range between 0° C and 60° C., and most preferably in a range between 0° C. and 40° C.

When the acrylic ester derivative is a water solution or solution, the density thereof is not especially limited, and a preferable density is in a range between 0.5 percent by weight and 99 percent by weight, more preferably in a range between 1 percent by weight and 80 percent by weight, further preferably in a range between 5 percent by weight and 60 percent by weight, and most preferably in a range between 10 percent by weight and 50 percent by weight. However, the density of the acrylic ester derivative can be determined depending on the handling and usage of the same.

Although, it depends on the kind of an acrylic ester, a preferable adding amount of a polymerization inhibitor, namely, a total amount of the first-order and second-order oxidation inhibitors, with respect to an amount of an acrylic ester is in a range between 0.001 percent by weight and 5 percent by weight, more preferably in a range between 0.005 percent by weight and 1 percent by weight, and most preferably in a range between 0.01 percent by weight and 0.1 percent by weight. An adding amount less than 0.001 percent by weight is not preferable because the polymerization is not curbed satisfactorily when the acrylic ester derivative is handled. An adding amount more than 5 percent by weight is not preferable either in terms of economy because not all the increased amount of the inhibitor is accompanied by further enhancement in the polymerization curbing effect, thereby wasting some of the polymerization inhibitor.

A process of adding a polymerization inhibitor to the acrylic ester derivative is not especially limited. When the acrylic ester derivative is either in a solid or liquid state, (1) powders of a polymerization inhibitor are added to the acrylic ester derivative, and (2) a water solution or solution of the acrylic ester derivative is prepared and a polymerization inhibitor is added to the resulting solution and water or a solvent is removed later, etc. Alternatively, a polymerization inhibitor may be added to the solution of the acrylic ester derivative obtained as a result of the above purification process, and water may be removed later. Further, when the acrylic ester derivative is in the form of a water solution or solution, a polymerization inhibitor is added to the water solution or solution.

When both the first-order and second-order oxidation inhibitors are used as a polymerization inhibitor, a preferable amount of the second-order oxidation inhibitor with respect to an amount of the first-order oxidation inhibitor is in a range between 1 percent by weight and 200 percent by weight. Using both the first-order and second-order oxidation inhibitors not only curbs the above polymerization more effectively, but also reduces an amount of the first-order oxidation inhibitor.

When a polymerization inhibitor includes a chleating agent, a preferable amount of the chelating agent with respect to a total amount of the first-order and second-order oxidation inhibitors is in a range between 0.0005 percent by weight and 100 percent by weight, more preferably in a range between 0.005 percent by weight and 25 percent by weight, and most preferably in a range between 0.01 percent by weight and 10 percent by weight. Adding a chleating agent not only curbs the above polymerization more effectively, but also reduces a relative amount of the first-order and second-order oxidation inhibitors. An adding amount less than 0.0005 percent by weight is not preferable because such an amount does not bring the effect of the chleating agent sufficiently. An adding amount of more than 100 percent by weight is not preferable either in terms of economy because not all the increased amount is accompanied with further enhancement in the polymerization curbing effect, thereby wasting some of the chleating agent. In addition, an amount of the first-order and second-order oxidation inhibitors is not reduced as was expected.

A process of adjusting a density of molecular oxygens in the gaseous phase is not especially limited. For example, the gaseous phase is substituted by introducing an inert gas, such as a nitrogen gas or argon gas, into the reactor in such a manner that the density of molecular oxygens will be in a range between 0.1 percent by capacity and 10 percent by capacity. A process of introducing an inert gas into the reactor is not especially limited. Adjusting the density of molecular oxygens to the above range curbs the polymerization more efficiently. When the density of molecular oxygens is below 0.1 percent by capacity, the polymerization of the acrylic ester derivative can not be curbed. When the density of molecular oxygens is above 10 percent by capacity, deterioration in quality due to oxidation or coloring of the acrylic ester derivative can not be curbed.

The acrylic-ester-based polymer of the present invention can be readily produced by letting an acrylic ester derivative undergo polymerization, or copolymerizing the acrylic ester derivative with a monomer that can copolymerize with the acrylic ester derivative (hereinafter, referred to as a monomer). Although it is described below, the water absorptive resin of the present invention is a crosslinked product of the above acrylic-ester-based polymer.

Examples of the monomer include, but are not limited to, hydrophobic olefin-based compounds including: alkylesters of (meta)acrylic acid, such as methyl(meta)acrylate, ethyl (meta)acrylate, butyl(meta)acrylate, amyl(meta)acrylate, hexyl(meta)acrylate, octyl(meta)acrylate, decyl(meta) acrylate, undecyl(meta)acrylate, lauryl(meta)acrylate, and stearyl(meta)acrylate; cycloalkylesters of (meta)acrylic acid, such as cyclopentyl(meta)acrylate and cyclohexyl (meta)acrylate;vinyl compounds, such as styrene, vinyl acetate, and vinyl propionate; nitriles, such as acrylonitrile;

hydrophilic olefin-based compounds including: 2-hydroxyethyl(meta)acrylate, 2-hydroxypropyl (meta) acrylate, 2-dimethylaminoethyl(meta)acrylate, 2-diethylaminoethyl(meta)acrylate, 3-dimethylaminopropyl(meta)acrylate, 3-diethylaminopropyl(meta)acrylate, polyethylene glycol mono(meta)acrylate, (meta)acrylamide, dimethyl (meta)acrylamide, (meta)acrylic acid, (meta)acrylic acid metallic salt, N-vinylpyrolidone, vinylcarbazole, acrylic esters expressed by Formula (2) above, etc;

multifunctional olefin-based compounds including: ethylene glycol di(meta)acrylate, diethylene glycol di(meta)acrylate, triethylene glycol di(meta)acrylate, triethylene glycol (meta)acrylate, vinyl(meta)acrylate, aryl(meta)acrylate, divinylbenzene, diarylphthalate, trimethylpropanetri(meta)acrylate, acrylic esters expressed by:

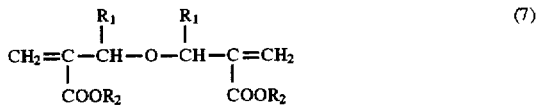

where $R_1$ represents a hydrogen atom or organic residue and $R_2$ represents a hydrogen atom, counter ion, or organic residue; etc. One or more than one of these monomers are used.

In other words, structure units of the acrylic-ester-based polymer of the present invention other than those expressed by Formula (5) above are not especially limited. An amount of the monomer, namely, a ratio of the monomer to the acrylic ester derivative is not especially limited.

A producing process of the acrylic-ester-based polymer is not especially limited. Known methods, for example, using a polymerization initiator including a radical polymerization initiator, irradiating UV rays and radial rays including as ionization radial rays and electronic rays, and heating are applicable.

Examples of the polymerization initiator include, but are not limited to, peroxides, such as benzoil peroxide, azo compounds, such as 2,2'-azobisisobutyronitrile, etc. An amount of the polymerization initiator and conditions of the polymerization reaction are not especially limited. An acrylic-ester-based polymer with a preferable polymerization degree has a number average molecular weight in a range between 1,000 and 2,000,000, and more preferably in a range between 5,000 and 1,500,000. It is preferable that the polymerization reaction takes place in an inert gas atmosphere, such as a nitrogen gas.

As has been explained, a new acrylic ester derivative of the present invention is of a structure expressed by Formula (1) above. The acrylic ester derivative is readily produced by reacting an acrylic ester expressed by Formula (2) above with a saccharide having a hemiacetal hydroxyl group expressed by Formula (3) above and/or an alkylglycoside expressed by Formula (4) above. A new acrylic-ester-based polymer of the present invention has a structure expressed unit by Formula (5) above, and the number average molecular weight of the same is in a range between 1,000 and 2,000,000.

Since saccharic resides are attached to side chains in the above acrylic ester derivative and acrylic-ester-based polymer without using the ester linkage, the linkage of the saccharic residues renders excellent resistance to hydrolysis.

In other words, the linkage is not hydrolyzed in the present of a base, and the saccharic residues are not released from the side chains. This means that the above acrylic-ester-based polymer can include the saccharic residues at the side chains in a stable manner. In addition, the saccharic residues are attached to the side chains in the same manner as seen in organisms or nature (glycoside linkage or the like). Hence, the above acrylic-ester-based polymer renders excellent biodegrability and bioadaptability.

Thus, the above acrylic-ester-based polymer renders excellent hydrophilic property, biodegrability, and bioadaptability, and can be used in various fields as a surface finishing agent, a medical material, a water absorptive resin, a surfactant, etc. A crosslinked product of the above acrylic-ester-based polymer renders excellent water absorption power, in particular, and therefore is preferably used as a water absorptive resin. Also, an acrylic ester derivative utilized for synthesizing the above acrylic-ester-based polymer can be readily produced by the above producing process.

The above acrylic-ester-based polymer preferably shows yellow index 50 or less, and more preferably 20 or less. The yellow index is evaluated by a method in compliance with JIS K 7103 using a Σ80-Model of a color-difference meter (Nippon Densyoku Kogyo Co., Ltd). Since the acrylic ester derivative of the present invention is hardly colored and has satisfactory hue, it renders high commercial values and utilities. Thus, the acrylic ester derivative of the present invention is preferably used for various purposes.

Next, a water absorptive resin of the present invention is described more in detail. The water absorptive resin referred herein is a crosslinked product of an acrylic-ester-based polymer.

The water absorptive resin has a structure unit expressed by Formula (5) above, and it is readily produced by letting a monomeric component including an acrylic ester derivative expressed by Formula (1) above undergo polymerization and crosslinking.

The water absorptive resin preferably includes, in addition to the one expressed by Formula (5) above, a structure unit expressed by:

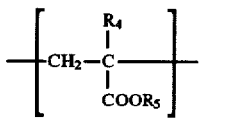
(8)

where $R_4$ represents a hydrogen atom or methyl group and $R_5$ represents a hydrogen atom, alkaline metal, or ammonium group. Including the above structure unit improves the water absorption power. Hereinafter, the structure unit represented by Formula (5) above and the structure unit represented by Formula (8) above are referred to as Structure Unit (5) and Structure Unit (8), respectively.

When the water absorptive resin also includes Structure Unit (8), a preferable amount of Structure Unit (8) with respect to a total amount of Structure Units (5) and (8) in the resin is less than 99.9 percent by mole. When an amount of Structure Unit (8) in the resin is 99.9 percent by mole or more, in other words, an amount of Structure Unit (5) in the resin is less than 0.1 percent by mole, the water absorptive resin may not be able to render satisfactory biodegrability.

The water absorptive resin may further include structure units other than Structure Units (5) and (8). In such a case, a total amount of the resin expressed by Structure Units (5) and (8) with respect to a total mount of the resin is preferably 90 or more percent by mole. Otherwise, the water absorptive resin may not be able to render satisfactory biodegrability and the water absorption power may be reduced.

The water absorptive resin including Structure Unit (8) is readily produced by copolymerizing a monomer based on (meta)aclryic acid expressed by Formula (9) below with a monomeric component including an acrylic ester derivative:

where $R_4$ represents a hydrogen atom or methyl group and $R_5$ represents a hydrogen atom, alkaline metal, or ammonium group. In other words, a water absorptive resin including Structure Units (5) and (8) is produced by copolymerizing an acrylic ester derivative that will form Structure Unit (5) with a monomeric component including (meta)acrylic acid that will form Structure Unit (8).

A preferred monomer based on (meta)acrylic acid is a product as a result by neutralizing (meta)acrylic acid partially, or so-called partial neutralized product. More precisely, the partial neutralized product is described as carboxyl groups in (meta)aclryic acid that are neutralized partially and form an alkaline metallic salt or ammonium salt, or it is also described as a mixture of a neutralized product and a non-neutralized product.

A neutralizing ratio of the above partial neutralized product of (meta)acrylic acid (hereinafter, referred to as a partial neutralized product), that is to say, a ratio of carboxyl groups forming alkaline metallic salt or ammonium salt to the entire carboxyl groups, is preferably in a range between 50 percent by mole and 95 percent by mole, and more preferably in a range between 60 percent by mole and 90 percent by mole. Therefore, a preferable partial neutralized product is a mixture composed of 5 mol %–50 mol % (meta)acrylic acid, 50 mol %–95 mol % alkaline (meta)acrylic acid metallic salt ($R_4$=alkaline metal) and/or 50 mol %–95 mol % (meta) acrylic acid ammonium salt ($R_4$ =ammonium group). The neutralizing ratio of the partial neutralized product is not limited to the above range; however, a neutralizing ratio below 50 percent by mole may degrade the water absorption power of the resulting water absorptive resin.

Examples of an alkaline metallic compound available to neutralize (meta)acrylic acid include, but are not limited to, hydroxides or hydrogen carbonates of alkaline metals, and the former is particularly preferred. Examples of the hydroxides of alkaline metals are sodium hydroxide, potassium hydroxide, lithium hydroxide, etc. Of all these compounds, sodium hydroxide and potassium hydroxide are particularly preferred in terms of water absorption power and cost.

The water absorptive resin of the present invention is produced by letting the above monomeric component undergo polymerization and crosslinking, and a process thereof is not especially limited. For example, while or after an acrylic-ester-based polymer, which is a water soluble resin, is produced by letting a monomeric component undergo polymerization, the acrylic-ester-based polymer is crosslinked by 1) adding a crosslinking agent, 2) adding a radical polymerization initiator, 3) irradiating radial rays, such as electronic rays.

Crosslinking the acrylic-ester-based polymer by adding a crosslinking agent can be performed in any of the followings: 1) a crosslinking agent is added to a monomeric component prior to polymerization; 2) a crosslinking agent is added after polymerization of a monomeric component has started but before it ends; 3) a crosslinking agent is added after the polymerization ends to let the polymerization continue; 4) the acrylic-ester-based polymer is placed when polymerization ends, and a cross linking agent is mixed with the acrylic-ester-based polymer; etc. Of all these adding methods, it is preferable to add a predetermined amount of crosslinking agent to a monomeric component prior to polymerization to let the monomeric component undergo crosslinking during or after the polymerization in efficiently producing the water absorptive resin with excellent water absorption power.

Examples of a crosslinking agent are a compound having more than one double bond capable of copolymerizing with an acrylic ester derivative included in a monomeric component, and a monomer based on (meta)acrlyic acid, and a compound having more than one functional group capable of reacting with a carboxyl group.

Examples of the compound having more than one double bond are ethylene glycol di(meta)acrylate, diethylene glycol di(meta)acrylate, polyethylene glycol di(meta)acrylate, propylene glycol di(meta)acryalte, polypropylene glycol di(meta)acrylate, grecerol tri(meta)acrylate, trimethylolpropane tri(meta)acrylate, N,N'-methylenebis(meta) acrylamide, diallyl phthalate, diallyl maleate, diallyl terephthalate, triallyl cyanurate, triallyl isocyanurate, triallyl phosphate, etc.

Examples of the compound having more than one functional group are:

polyatomic alcohol compounds, such as ethylene glycol, diethylene glycol, propylene glycol, triethylene glycol, tetraethylene glycol, polyethylene glycol, propylene glycol, 1,3-propanediol, dipropylene glycol, 2,2,4-trimethyl-1,3-pentanediol, polypropylene glycol, gylceline, polyglyceline, 2-butene-1,4-diol, 1,4-butanediol, 1,5-pentanediol, 1,6-hexanediol, 1,2-cyclohexane dimethanol, 1,2-cycylohexanediol, trimethylolpropane, diethanolamine, triethanolamine, polyoxypropylene, oxyethylene-oxypropylene block copolymer, pentaerythritol, and sorbitol;

epoxy compounds, such as ethylene glycol digylcidyl ether, polyethylene diglycidyl ether, glycerol polyglycidyl ether, diglycerol polygycidyl ether, polygycerol polyglycidyl ether, propylene glycol diglycidyl ether, polypropylene glycol diglycidyl ether, and glycidol;

polyatomic amine compounds, such as ethylenediammine, diethylenetriamine, triethylenetetramine, tetraethylenepentamine, pentaethylenehexamine, and polyamide polyamine polyetheyleneimine, and a condensation product of these polyatomic amine compounds and haloexpoxy compounds;

polyatomic isocyanurate compounds, such as 2,4-tolylene diisocyanurate and hexamethylene diisocyanurate;

polyatomic oxazoline compounds, such as 1,2-ethylenebisoxazoline;

silane coupling agents, such as γ-glycidoxypropyltrimethoxysilane and γ-aminopropyltrimethoxysilane;

alkylene carbonate compounds, such as 1,3-dioxolane-2-one, 4-methyl-1,3-dioxyolane-2-one, 4,5-dimethyl-1,3-dioxolane-2-one, 4,4-dimethyl-,1, 3-dioxolane-2-one, 4-ethyl-1, 3-dioxolane-2-one, 4-hydroxymethyl-1, 3-dioxolane-2-one, 1,3-dioxane-2-one, 4-methyl-1,3-dioxane-2-one, 4,6-dimethyl-1,3-dioxane-2-one, and 1,3-dioxopane-2-one;

haloepoxy compounds, such as epichlorohydrin, epibromhydrin and α-methylepichlorohydrin; and hydroxides or chlorides of polyatomic metals, such as zinc, calcium, magnesium, alminium, iron, and zirconium; etc. One or more than one of these crosslinking agents are used. An adding amount of the crossing agent is not especially limited, and it can be determined based on the kind or amount of the monomeric component, or the kind of the crosslinking agent.

The monomeric component may include monomeric ingredients other than acrylic ester derivatives and monomers based on (meta)acrylic acid. The monomeric ingredients referred herein are, for example, hydrophilic or hydrophobic monomers. However, the monomeric ingredients are not especially limited and any compound having a double bond capable of copolymerizing with the acrylic ester derivatives and monomers based on (meta)acrlyic acid will do.

Examples of the hydrophilic monomer are:

nonionic hydrophilic monomers, such as (meta) acrylamide, N-ethyl(meta)acrylamide, N-n-propyl (meta)acrylamide, N-isopropyl(meta)acrylamide, N,N-dimethyl (meta)acrylamide, 2-hydroxyethyl(meta) acrylate, 2-hydroxypropyl(meta)acrylate, methoxypolyethylene glycol(meta)acrylate, polyethylene glycol mono(meta)acrylate, vinylpyridine, N-vinylpyrolidone, N-acryloylpiperidine, and N-acryloylpyrolidine; and cationic hydrophilic monomer, such as N,N-dimethylaminoethyl(meta)acrylate, N,N-diethylaminoethyl(meta)acrylate, N,N-dimethylaminopropyl(meta)acrylate, and N,N-dimethylaminopropyl (meta )acrylamide, and quaternary salts thereof; etc. Of all these hydrophilic monomers, methoxypolyethlene glycol(meta)acrylate, N,N-dimethylaminoethyl(meta)acrylate and quaternary salt thereof, and (meta)acrylamide are preferred. One or more than one of these hydrophilic monomers are used. Components such that produce hydrophilic functional groups through post-polymerization hydrolysis, such as methyl(meta)acrylate, ethyl(meta)acrylate, and vinyl acetate, are also available as a hydrophilic monomer.

Examples of the hydrophobic monomers are styrene, vinyl chloride, butadiene, isobutene, ethylene, propylene, stearyl(meta)acrylate, lauryl(meta)acrylate, etc. One or more than one of these hydrophobic monomers are used.

Further, a soluble chain transferring agent or compound, such as hydrophilic polymer, may be present together in the reactant while a monomeric component undergoes polymerization in the producing process of a water absorptive resin of the present invention. Examples of the soluble chain transferring agent are hypophosphorous acid salt, thiols, thiolic acid, etc. Examples of hydrophilic polymer are celluose, amylose (starch), polyvinylalcohol, polyacrylic acid, crosslinked polyacrylate, etc.

The monomeric component may be polymerized by bulk or precipitation polymerization. However, it is preferable to polymerize the monomeric component in a liquid state by dissolving the same into a solvent in terms of water absorption power and readiness in control. The solvent referred herein is any inactive liquid compound capable of dissolving the monomeric component, and water or water solution is particularly preferable. Examples of the solvent include, but are not limited to, water, methanol, ethanol, acetone, dimethylsufoxide, N,N-dimethylformamide, etc. One or more than one of these solvents are used.

A density of the monomeric component in the solution may exceed saturation, but a preferable range is between 20 percent by weight and saturation, and more preferably between 25 percent by weight and 50 percent by weight. When the monomeric component is too dense, properties of a resulting water absorptive resin may be degraded.

A pH of the monomeric component solution is not especially limited, and pH 4 or above is preferable. If the monomeric component solution has a pH below 4, the biodegrability of a resulting water absorptive resin may be degraded.

A process of polymerizing the monomeric component is not especially limited, and any of the following known methods is available: radical polymerization using a radical polymerization initiator; irradiation of radial rays, such as ionization redial rays and electronic rays; irradiation of UV rays using a photointensifier; etc. Of all these methods, the radical polymerization is particularly preferred because a resulting water absorptive resin renders better water absorption power.

The radical polymerization includes casting polymerization performed in a mold form, thin layer polymerization performed on a belt conveyer, solution polymerization dividing a polymer of hydrous gel into pieces, negative phase suspension polymerization, negative phase emulsion polymerization, precipitation polymerization, bulk polymerization, etc. Of all these polymerizations, the negative phase suspension polymerization and solution polymerization are particularly preferred.

The monomeric component is polymerized by either continuous or batch method under a vacuumed, pressured, or normal pressure. Further, the monomeric component may be polymerized either with or without stirring the reactant. That is to say, stationary polymerization is also applicable. A polymerizing temperature is preferably maintained substantially in a range between 0° C. and 100° C. except for the initial peak of the polymerization.

Examples of the radical polymerization initiator are: persulfates, such as ammonium persulfate, sodium persulfate, and potassium persulfate; organic peroxides, such as t-butylhydro peroxide and cumenehydro peroxide; hydrogen peroxide; azo compounds, such as 2,2'-azobis(2-amdinopropane)dihydrochloride; chlorite, hypochlorite, seccerium salt, permanganate; etc. Of all these example compounds, persulfates, hydrogen peroxide, and azo compounds are preferred. One or more than one of these radical polymerization initiators are used.

When an acid radical polymerization initiator, such as persulfate, hydrogen peroxide, and an azo compound, is used, a reducing agent, such as sulfite, hydrogen salt sulfite, and L-ascorbic acid, may be used together. When an azo compound is used, the UV ray polymerization also may be triggered by irradiating UV rays.

The radical polymerization initiator is added to the reactant either in one portion or several portions. An amount of the radical polymerization initiator with respect to an amount of the monomeric component is not especially limited, and a preferable range is between 0.001 percent by mole and 2 percent by mole, and more preferably between 0.01 percent by mole and 1 percent by mole.

A polymer of hydrous gel, namely a polymer of the monomeric component, is produced by any of the above polymerization. The water absorptive resin, namely, a crosslinked product of an acrylic-ester-based polymer, is produced when the polymer of hydrous gel is dried. A process of drying the polymer of hydrous gel is not especially limited, and any known method is applicable. For example, driers, such as vacuum drier, chamber drier, aeration drier, aeration band drier, vertical aeration type drier, and rotary drier can be used.

A drying temperature is not especially limited, and a preferable range is between 50° C. and 250° C., and more preferably between 80° C. and 200° C. Drying at a temperature above 250° C. may cause degradation or decomposition of the water absorptive resin. Drying at a temperature below 50° C. prolongs the time for drying, thereby reducing productivity of the water absorptive resin.

When particles of water absorptive resin are produced, the polymer of hydrous gel, when dried, is ground. A grinding method is not especially limited, and any known method will do. For example, high-speed rotary grinders, such as a pin mill or a hammer mill; a screw mill (coffee mill), a roll mill, and a vibrating mill, are available.

As has been explained, the water absorptive resin of the present invention is a crosslinked product of an acrylic-ester-based polymer and has a structure unit expressed by Formula (5) above. The water absorptive resin is readily produced by letting a monomeric component including an acrylic ester derivative expressed by Formula (1) above undergo polymerization and crosslinking.

Thus, the water absorptive resin renders excellent water absorption power. Moreover, the saccharic residues link to the side chains in the same manner as seen in organisms or nature, thereby rendering excellent biodegrability to the water absorptive resin. Accordingly, the water absorptive resin is readily decomposed by bacteria and microbes in soil. Therefore, the water absorptive resin or water absorptive goods made out of the water absorptive resin can be buried in soil when disposed. This means the water absorptive resin can be disposed in a simple and secured manner without polluting environments. In short, the water absorptive resin is environmentally benign. In addition, the water absorptive resin can be produced readily and efficiently by the above process.

The use of the water absorptive resin is not limited to sanitary materials, such as paper diapers and sanitary items, and the water absorptive resin is now used in many ways in various fields: a body fluid absorber in the medical industry; a sealing material (water stopping material) or dewing inhibitor in the civil engineering and construction industry; a freshness preserver in the food industry; a dehydrating material for removing water from a solvent in the manufacturing industry; a planting material in the agricultural and gardening industry. For instance, the water absorptive resin is used as a water-oil separator, a waste solution absorber, a vibration-proof material, a noise-proof material, sundries, toys, artificial snow, etc.

The following description will describe the present invention more in detail, but the present invention is not limited to the disclosure below. COMPARATIVE EXAMPLES 1 and 2 are performed in comparison to EXAMPLES 24 through 27, and COMPARATIVE EXAMPLES 3 through 5 are performed in comparison to EXAMPLES 40 through 50. COMPARATIVE EXAMPLES 6 and 7 are performed in comparison to EXAMPLES 51 through 56, and COMPARATIVE EXAMPLES 8 and 9 are performed in comparison to EXAMPLES 57 through 62.

EXAMPLE 1

To begin with, 65.0 g of ethyl-α-hydroxymethylacrylate serving as an acrylic ester and 1.30 g of p-t-butylcatechol serving as a polymerization inhibitor (first-order oxidation inhibitor) are stirred in a reactor having a capacity of 300ml and equipped with a thermometer and a stirring device. Next, 18.0 g of glucose serving as a saccharide containing a hemiacetal hydroxyl group and 0.7 g of paratoluenesulfonic acid monohydrate serving as a catalyst are added, and the reactant solution is heated slowly with stirring. Further, the reactant solution is subject to stirring for two hours at 100° C. under a normal pressure.

When the reaction ends, the reactant solution is neutralized with a 2N-sodium hydroxide water solution serving as a neutralizer, and subject to vacuum concentration by a predetermined method. The resulting concentrate solution is separated and purified by the Column Chromatography. A solution made of chloroform and methanol in the ratio of 9:1 is used as a developing solvent, and silica gel is used as an absorbent.

Figure 2:
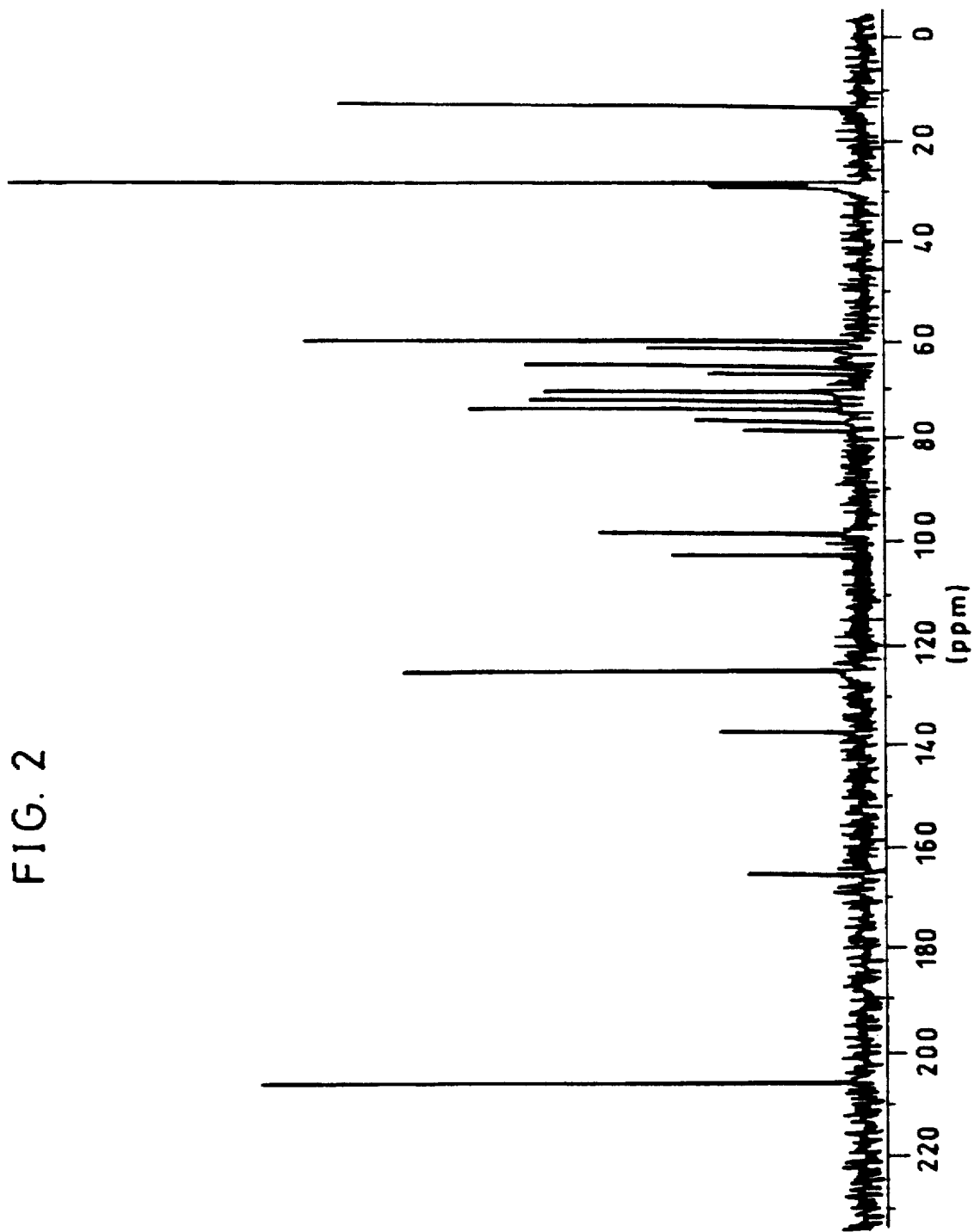
FIG. 2 is a $^{13}$C-NMR chart of the above reaction product.
Figure 3:
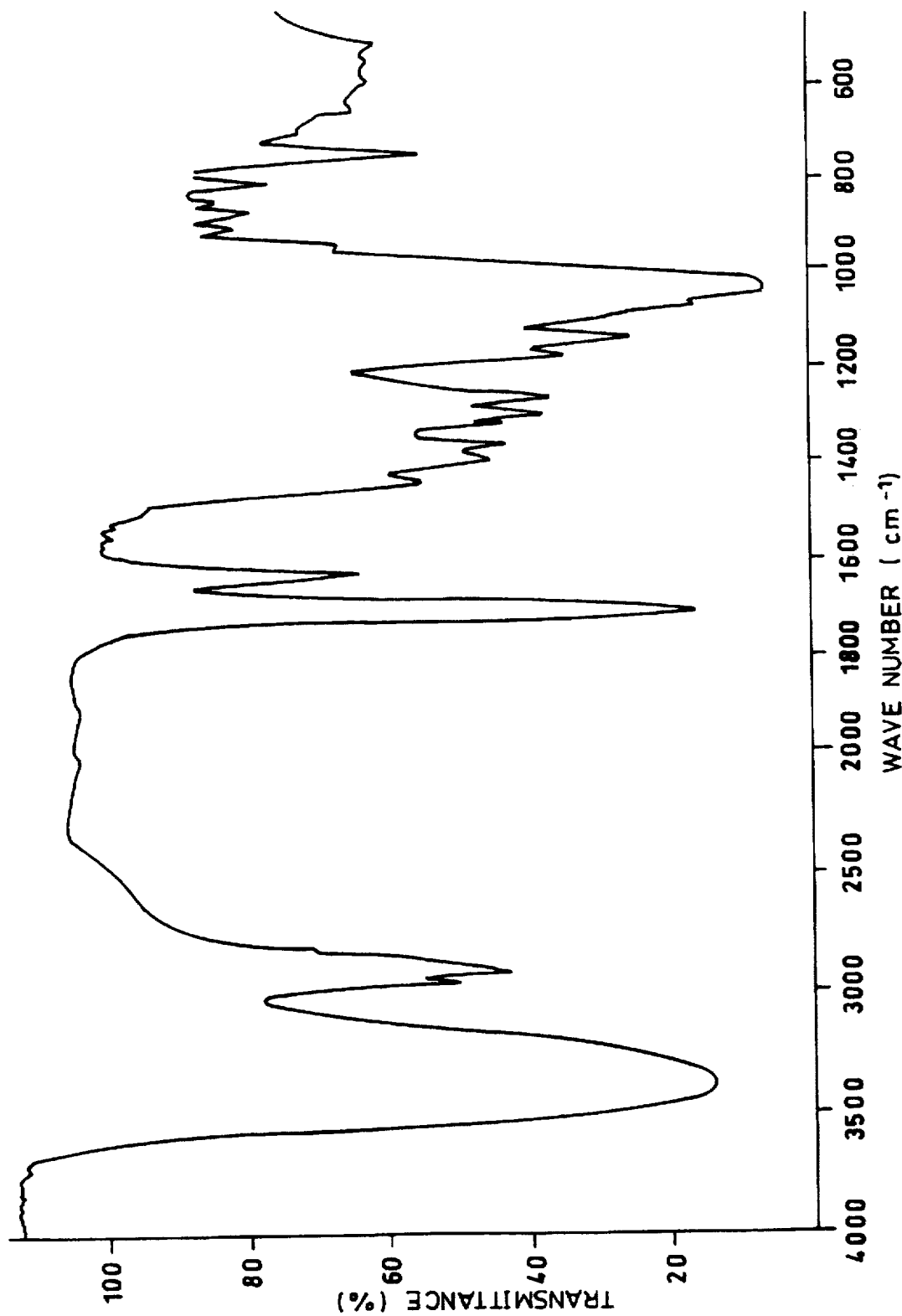
FIG. 3 is a view showing an infrared absorption spectrum of the above reaction product.

To identify the resulting product, $^1$H-NMR, $^{13}$C-NMR, and infrared absorption spectrum (IR) of the product are evaluated and an elemental analysis is performed. As a result, the product is identified as a new acrylic ester derivative of the present invention, namely, ethyl-α-(glucosidemethyl) acrylate. The $^1$H-NMR chart, $^{13}$C-NMR chart, and infrared absorption spectrum (IR) of the reactant product are shown in FIGS. 1, 2, and 3, respectively. The yield of ethyl-α-(glucosidemethyl)acrylate evaluated by a predetermined method is 63 percent by mole.

The conditions and result of the above reaction are set forth in TABLEs 1-1 and 2-1 below. The absorption wave number of the infrared absorption spectrum and the result of the elemental analysis of ethyl-α-(glucosidemethyl)acrylate are set forth in TABLE 3-1 below.

EXAMPLE 2

Herein, 65.0 g of ethyl-α-hydroxymethylacrylate, 0.07 g of hydroquinone serving as a polymerization inhibitor (first-order oxidation inhibitor), and 80 g of toluene serving as an azeotropic solvent are stirred in a reactor of the same type used in EXAMPLE 1. Then, 9.0 g of glucose and 1.0 g of hydrochloric acid serving as a catalyst are added, and the reactant solution is heated slowly with stirring. Next, the reactor is vacuumed when the reactant solution is heated up to 75° C. Then, the reactant solution is subject to stirring for two hours at 90° C. under 350 mmHg. Water (alcohol) produced as a result of the reaction is removed from the reactant by azeotropy using toluene, which is known as the Dean and Stark method.

When the reaction ends, the reactant solution is neutralized with a sodium carbonate anhydride ($Na_2CO_3$) serving as a neutralizer, and the resulting neutralized solution is separated and purified in the same manner as EXAMPLE 1.

The resulting product is identified, in the same manner as EXAMPLE 1, as the same product obtained in EXAMPLE 1, namely, ethyl-α-(glucosidemethyl)acrylte. The yield of ethyl-α-(glucosidemethyl)acrylate evaluated by a predetermined method is 68 percent by mole. The conditions and result of the above reaction are set forth in TABLEs 1-1 and 2-1.

EXAMPLE 3

Herein, 65.0 g of ethyl-α-hydroxymethylacrylate, 0.65 g of hydroquinone monomethyl ether serving as a polymerization inhibitor (first-order oxidation inhibitor), and 100 g of chlorobenzene serving as a solvent are stirred in a reactor of the same type used in EXAMPLE 1. Then, 19.4 g of methylglucoside serving as an alkylglycoside and 1.0 g of tungstophosphoric acid serving as a catalyst are added, and the reactant solution is heated slowly with stirring. Further, the reactant solution is subject to stirring for two hours under a normal pressure with chlorobenzene being refluxed.

When the reaction ends, the reactant solution is neutralized with a 2N-sodium hydroxide water solution. The resulting neutralized solution is concentrated, separated, and purified in the same manner as EXAMPLE 1.

The resulting product is identified, in the same manner as EXAMPLE 1, as the same product obtained in EXAMPLE 1, namely, ethyl-α-(glucosidemethyl)acrylate. The yield of ethyl-α-(glucosidemethyl)acrylate evaluated by a predetermined method is 60 percent by mole. The reaction conditions and result of the above reaction are set forth in TABLEs 1-1 and 2-1.

EXAMPLE 4

Herein, 65.0 g of ethyl-α-hydroxymethylacrylate, 0.10 g of p-t-butylcatechol, and 10 g of cyclohexane serving as an azeotropic solvent are stirred in a reactor of the same type used in EXAMPLE 1. Next, 12.0 g of galactose serving as a saccharide containing a hemiacetal hydroxyl group and 2.6 g of boron trifluoride ethyl ether complex serving as a catalyst are added, and the reactant solution is heated slowly with stirring. Further, the reactant solution is subject to stirring for two hours at 95° C. under a normal pressure. Water produced as a result of the reaction is removed from the reactant by azeotropy using cyclohexane, or the Dean and Stark method.

When the reaction ends, the reactant solution is neutralized with a 2N-potassium hydroxide water solution serving as a neutralizer. The resulting neutralized solution is concentrated, separated, and purified in the same manner as EXAMPLE 1.

The resulting product is identified, in the same manner as EXAMPLE 1, as a new acrylic ester derivative of the present invention, namely, ethyl-α-(galactosidemethyl)acrylate. The yield of ethyl-α-(galactosidemethyl)acrylate evaluated by a predetermined method is 68 percent by mole.

The conditions and result of the above reaction are set forth in TABLEs 1-1 and 2-1 below. The absorption wave number of the infrared absorption spectrum and the result of the elemental analysis of ethyl-α-(galactosidemethyl) acrylate are set forth in TABLE 3-1 below.

EXAMPLE 5

Herein, 65 g of ethyl-α-hydroxymethylacrylate and 0.03 g of phenothiazine serving as a polymerization inhibitor (first-order oxidation inhibitor) are stirred in a reactor of the same type used in EXAMPLE 1. Then, 20.8 g of ethylgalactoside serving as an alkylglycoside and 1.6 g of molybdophosphoric acid serving as a catalyst are added, and the reactant solution is heated slowly with stirring. Further, the reactant solution is subject to stirring for two and a half hours at 80° C. under a normal pressure.

When the reaction ends, the reactant solution is neutralized with a 1N-potassium hydroxide water solution serving as a neutralizer. The resulting neutralized solution is concentrated, separated, and purified in the same manner as EXAMPLE 1.

The resulting product is identified, in the same manner as EXAMPLE 1, as the same product obtained in EXAMPLE 4, namely, ethyl-α-(galactosidemethyl)acryalte. The yield of ethyl-α-(galactosidemethyl)acrylate evaluated by a predetermined method is 62 percent by mole. The conditions and result of the above reaction are set forth in TABLEs 1-1 and 2-1.

EXAMPLE 6

Herein, 65.0 g of ethyl-α-hydroxymethylacrylate, 0.02 g of hydroquinone monomethyl ether, and 15 g of cyclohexane are stirred in a reactor of the same type used in EXAMPLE 1. Then, 22.1 g of N-acetylglucosamine serving as a saccharide containing a hemiacetal hydroxyl group, and 3.0 g of paratoluenesulfonic acid monohydrate are added, and the reactant solution is heated slowly with stirring. Further, the reactant solution is subject to stirring for two hours at 90° C. under a normal pressure. Water produced as a result of the reaction is removed from the reactant by azeotropy using cyclohexane, or the Dean and Stark method.

When the reaction ends, the reactant solution is neutralized with a 1N-sodium hydroxide water solution serving as a neutralizer. The resulting neutralized solution is concentrated, separated, and purified in the same manner as EXAMPLE 1.

The resulting product is identified, in the same manner as EXAMPLE 1, as a new acrylic ester derivative of the present invention, namely, ethyl-α-(2-acetamide-2-deoxyglucosidemethyl)acrylate. The yield of ethyl-α-(2-acetamide-2-deoxyglucosidemethyl)acrylate evaluated by a predetermined method is 59 percent by mole.

The conditions and result of the above reaction are set forth in TABLEs 1-1 and 2-1 below. The absorption wave number of the infrared absorption spectrum and the result of the elemental analysis of ethyl-α-(2-acetamide-2-deoxyglucosidemethyl)acrylate are set forth in TABLE 3-1 below.

EXAMPLE 7

Herein, 65.0 g of ethyl-α-hydroxymethylacrylate and 0.65 g of hydroquinone are stirred in a reactor of the same type used in EXAMPLE 1. Then, 22.5 g of xylose serving as a saccharide containing a hemiacetal hydroxyl group, 12.0 g of ion exchange resin (Dowex-50 W of the Dow Chemical Co.) serving as a catalyst are added, and the reactant solution is heated slowly with stirring. Further, the reactant solution is subject to stirring for five hours at 100° C. under a normal pressure.

When the reaction ends, the ion exchange resin is removed from the reactant solution through filtration. The resulting filtrate is separated and purified in the same manner as EXAMPLE 1.

The resulting product is identified, in the same manner as EXAMPLE 1, as a new acrylic ester derivative of the present invention, namely, ethyl-α-(xylosidemethyl)acrylate. The yield of ethyl-α-(xylosidemethyl)acrylate evaluated by a predetermined method is 52 percent by mole.

The conditions and result of the above reaction are set forth in TABLEs 1-1 and 2-1 below. The absorption wave number of the infrared absorption spectrum and the result of the elemental analysis of ethyl-α-(xylosidemethyl)acrylate are set forth in TABLE 3-1 below.

EXAMPLE 8

Herein, 65.0 g of ethyl-α-hydroxymethylacrylate and 0.04 g of p-benzoquinone serving as a polymerization inhibitor (first-order oxidation inhibitor) are stirred in a reactor of the same type used in EXAMPLE 1. Then, 8.2 g of methylxyloside serving as an alkylglycoside and 0.8 g of molybdosilicic acid serving as a catalyst are added, and the reactant solution is heated slowly with stirring. The reactor is vacuumed when the reactant solution is heated up to 75° C. Further, the reactant solution is subject to stirring for two hours at 90° C. under 600 mmHg. Methylalcohol (alcohol) produced as a result of the reaction is removed from the reactant.

When the reaction ends, the reactant solution is neutralized with a sodium carbonate anhydride. The resulting neutralized solution is separated and purified in the same manner as EXAMPLE 1.

The resulting product is identified, in the same manner as EXAMPLE 1, as the same product obtained in EXAMPLE 7, namely, ethyl-α-(xylosidemethyl)acrylate. The yield of ethyl-α-(xylosidemethyl)acrylate evaluated by a predetermined method is 58 percent by mole. The conditions and result of the above reaction are set forth in TABLEs 1-1 and 2-1 below.

EXAMPLE 9

Herein, 65.0 g of ethyl-α-hydroxymethylacrylate, 0.08 g of p-t-butylcatechol, and 10 g of heptane serving as an azeotropic solvent are stirred in a reactor of the same type used in EXAMPLE 1. Then, 18.0 g of maltose serving as a saccharide containing a hemiacetal hydroxyl group and 0.5g of sulfuric acid serving as a catalyst are added, and the reactant solution is heated slowly with stirring. Further, the reactant solution is subject to stirring for three hours at 100° C. under a normal pressure. Water produced as a result of the reaction is removed from the reactant by azeotropy using heptane, or the Dean and Stark method.

When the reaction ends, the reactant solution is neutralized with a 2N-sodium hydroxide solution. The resulting neutralized solution is concentrated, separated, and purified in the same manner as EXAMPLE 1.

The resulting product is identified, in the same manner as EXAMPLE 1, as a new acrylic ester derivative of the present invention, namely, ethyl-α-(maltosidemethyl)acrylate. The yield of ethyl-α-(maltosidemethyl)acrylate evaluated by a predetermined method is 50 percent by mole.

The conditions and result of the above reaction are set forth in TABLEs 1-1 and 2-1 below. The absorption wave number of the infrared absorption spectrum and the result of the elemental analysis of ethyl-α-(maltosidemethyl)acrylate are set forth in TABLE 3-1 below.

EXAMPLE 10

Herein, 65.0 g of ethyl-α-hydroxymethylacrylate, 0.30 g of hydroquinone monomethyl ether, and 75 g of o-xylene serving as an azeotropic solvent are stirred in a reactor of the same type used in EXAMPLE 1. Then, 17.1 g of lactose serving as a saccharide containing a hemiacetal hydroxyl group and 13.0 g of ion exchange resin (Diaion SK of Mitsubishi Chemical Corporation) serving as a catalyst are added, and the reaction solution is heated slowly with stirring. The reactor is vacuumed when the reaction solution is heated up to 70° C. Then, the reaction solution is subject to stirring for six hours at 95° C. under 160 mmHg. Water produced as a result of the reaction is removed from the reactant by azeotropy using o-xylene, or the Dean and Stark method.

When the reaction ends, the ion exchange resin is removed from the reactant solution through filtration. The resulting filtrate is separated and purified in the same manner as EXAMPLE 1.

The resulting product is identified, in the same manner as EXAMPLE 1, as a new acrylic ester derivative of the present invention, namely, ethyl-α-(lactosidemethyl)acrylate. The yield of ethyl-α-(lactosidemethyl)acrylate evaluated by a predetermined method is 48 percent by mole.

The conditions and result of the above reaction are set forth in TABLEs 1-2 and 2-2 below. The absorption wave number of the infrared absorption spectrum and the result of the elemental analysis of ethyl-α-(lactosidemethyl)acrylate are set forth in TABLE 3-1 below.

EXAMPLE 11

Herein, 65.0 g of ethyl-α-hydroxymethylacrylate and 0.25 g of phenothiazine are stirred in a reactor of the same type used in EXAMPLE 1. Then, 41.4 g of maltopentaose serving as a saccharide containing a hemiacetal hydroxyl group and 1.0 g of hydrochloric acid are added, and the reactant solution is heated slowly with stirring. Further, the reactant solution is subject to stirring for three hours at 85° C. under a normal pressure.

When the reaction ends, the reactant solution is neutralized with a sodium carbonate anhydride. The resulting neutralized solution is separated and purified in the same manner as EXAMPLE 1.

The resulting product is identified, in the same manner as EXAMPLE 1, as a new acrylic ester derivative of the present invention, namely, ethyl-α-(maltopentaosidemethyl) acrylate. The yield of ethyl-α-(maltopentaosidemethyl) acrylate evaluated by a predetermined method is 42 percent by mole.

The conditions and result of the above reaction are set forth in TABLEs 1-2 and 2-2 below. The absorption wave number of the infrared absorption spectrum and the result of the elemental analysis of ethyl-α-(maltopentaosidemethyl) acrylate are set forth in TABLE 3-1 below.

EXAMPLE 12

Herein, 79.0 g of n-butyl-α-hydroxymethylacrylate serving as an acrylic ester and 0.39 g of hydroquinone monomethyl ether are stirred in a reactor of the same type used in EXAMPLE 1. Then, 13.5 g of glucose and 15.0 g of ion exchange resin (Dowex-50 W) are added, and the reactant solution is heated slowly with stirring. Further, the reactant solution is subject to stirring for five hours at 95° C. under a normal pressure.

When the reaction ends, the ion exchange resin is removed from the reaction solution through filtration. The resulting filtrate is separated and purified in the same manner as EXAMPLE 1.

The resulting product is identified, in the same manner as EXAMPLE 1, as a new acrylic ester derivative of the present invention, namely, n-butyl-α-(glucosidemethyl)acrylate. The yield of n-butyl-α-(glucosidemethyl)acrylate evaluated by a predetermined method is 60 percent by mole.

The conditions and result of the above reaction are set forth in TABLEs 1-2 and 2-2 below. The absorption wave number of the infrared absorption spectrum and the result of the elemental analysis of n-butyl-α-(glucosidemethyl) acrylate are set forth in TABLE 3-2 below.

EXAMPLE 13

Herein, 79.0 g of n-butyl-α-hydroxymethylacryalte, 0.79 g of hydroquinone, and 85 g of chlorobenzene are stirred in a reactor of the same type used in EXAMPLE 1. Then, 18.0 g of galactose and 1.0 g of paratoluenenesulfonic acid monohydrate are added, and the reactant solution is heated slowly with stirring. Further, the reactant solution is subject to stirring for two hours under a normal pressure with chlorobenzene being refluxed.

When the reaction ends, the reactant solution is neutralized with a sodium carbonate anhydride. The resulting neutralized solution is separated and purified in the same manner as EXAMPLE 1.

The resulting product is identified, in the same manner as EXAMPLE 1, as a new acrylic ester derivative of the present invention, namely, n-butyl-α-(galactosidemethyl)acrylate. The yield of n-butyl-α-(galactosidemethyl)acrylate evaluated by a predetermined method is 61 percent by mole.

The conditions and result of the above reaction are set forth in TABLEs 1-2 and 2-2 below. The absorption wave number of the infrared absorption spectrum and the result of the elemental analysis of n-butyl-α-(galactosidemethyl) acrylate are set forth in TABLE 3-2 below.

EXAMPLE 14

Herein, 79.0 g of n-butyl-α-hydroxymethylacrylate, 0.06 g of p-benzoquinone, and 110 g of toluene are stirred in a reactor of the same type used in EXAMPLE 1. Then, 16.6 g of N-acetylglucosamine and 0.5 g of hydrochloric acid are added, and the reactant solution is heated slowly with stirring. Then, the reactor is vacuumed when the reactant solution is heated up to 75° C. Further, the reactant solution is subject to stirring for one and a half hour at 100° C. under 550 mmHg. Water produced as a result of the reaction is removed from the reactant by azeotropy using toluene, or the Dean and Stark method.

When the reaction ends, the reactant solution is neutralized with a 2N-sodium hydroxide solution. The resulting neutralized solution is concentrated, separated, and purified in the same manner as EXAMPLE 1.

The resulting product is identified, in the same manner as EXAMPLE 1, as a new acrylic ester derivative of the present invention, namely, n-butyl-α-(2-acetamide-2-deoxyglucosidemethyl)acrylate. The yield of n-butyl-α-(2-acetamide-2-deoxyglucosidemethyl) acrylate evaluated by a predetermined method is 60 percent by mole.

The conditions and result of the above reaction are set forth in TABLEs 1-2 and 2-2 below. The absorption wave number of the infrared absorption spectrum and the result of the elemental analysis of n-butyl-α-(2-acetamide-2-deoxyglucosidemethyl)acrylate are set forth in TABLE 3-2 below.

EXAMPLE 15

Herein, 79.0 g of n-butyl-α-hydroxymethylacrylate, 0.08 g of phenothiazine, and 70 g of benzene are stirred in a reactor of the same type used in EXAMPLE 1. Then, 15.0 g of xylose and 2.0 g of boron trifluoride ethyl ether complex are added, and the reactant solution is heated slowly with stirring. Further, the reactant solution is subject to stirring for two hours under a normal pressure with benzene being refluxed.

When the reaction ends, the reactant solution is neutralized with a 1N-potassium hydroxide water solution. The resulting neutralized solution is concentrated, separated, purified in the same manner as EXAMPLE 1.

The resulting product is identified, in the same manner as EXAMPLE 1, as a new acrylic ester derivative of the present invention, namely, n-butyl-α-(xylosidemethyl)acrylate. The yield of n-butyl-α-(xylosidemethyl)acrylate evaluated by a predetermined method is 53 percent by mole.

The conditions and result of the above reaction are set forth in TABLEs 1-2 and 2-2 below. The absorption wave number of the infrared absorption spectrum and the result of the elemental analysis of n-butyl-α-(xylosidemethyl) acrylate are set forth in TABLE 3-2 below.

EXAMPLE 16

Herein, 79.0 g of n-butyl-α-hydroxymethylacrylate and 0.10 g of hydroquinone monomethyl ether are stirred in a reactor of the same type used in EXAMPLE 1. Then, 22.5 g of maltose and 15.0 g of ion exchange resin (Dowex-50 W) are added, and the reactant solution is heated slowly with stirring. Further, the reactant solution is subject to stirring for six hours at 100° C. under a normal pressure.

When the reaction ends, the ion exchange resin is removed from the reactant solution through filtration. The resulting filtrate is separated and purified in the same manner as EXAMPLE 1.

The resulting product is identified, in the same manner as EXAMPLE 1, as a new acrylic ester derivative of the present invention, namely, n-butyl-α-(maltosidemethyl)acrylate. The yield of n-butyl-α-(maltosidemethyl)acrylate evaluated by a predetermined method is 42 percent by mole.

The conditions and result of the above reaction are set forth in TABLEs 1-2 and 2-2 below. The absorption wave number of the infrared absorption spectrum and the result of the elemental analysis of n-butyl-α-(maltosidemethyl) acrylate are set forth in TABLE 3-2 below.

EXAMPLE 17

Herein, 58.0 g of methyl-α-hydroxymethylacrylate serving as an acrylic ester, 0.06 g of phenothiazine, and 8 g of cyclohexane are stirred in a reactor of the same type used in EXAMPLE 1. Then, 12.0 g of glucose and 0.6 g of paratoluenesulfonic acid monohydrate are added, and the reactant solution is heated slowly with stirring. Further, the reactant solution is subject to stirring for two hours at 100° C. under a normal pressure. Water produced as a result of the reaction is removed from the reactant by azeotropy using cyclohexane, or the Dean and Stark method.

When the reaction ends, the reaction solution is neutralized with a sodium carbonate anhydride. The resulting neutralized solution is separated and purified in the same manner as EXAMPLE 1.

The resulting product is identified, in the same manner as EXAMPLE 1, as a new acrylic ester derivative of the present invention, namely, methyl-α-(glucosidemethyl)acrylate. The yield of methyl-α-(glucosidemethyl)acrylate evaluated by a predetermined method is 67 percent by mole.

The conditions and result of the above reaction are set forth in TABLEs 1-3 and 2-3 below. The absorption wave number of the infrared absorption spectrum and the result of the elemental analysis of methyl-α-(glucosidemethyl) acrylate are set forth in TABLE 3-2 below.

EXAMPLE 18

Herein, 58.0 g of methyl-α-hydroxymethylacrylate, 0.58 g of hydroquinone monomethyl ether, and 100 g of toluene are stirred in a reactor of the same type used in EXAMPLE 1. Then, 13.5 g of galactose and 11.0 g of ion exchange resin (Dowex-50 W) are added, and the reactant solution is heated slowly with stirring. Then, the reactor is vacuumed when the reactant solution is heated up to 75° C. Further, the reactant solution is subject to stirring for five hours at 100° C. under 550 mmHg. Water produced as a result of the reaction is removed from the reactant by azeotropy using toluene, or the Dean and Stark method.

When the reaction ends, the ion exchange resin is removed from the reactant solution through filtration. The resulting filtrate is separated and purified in the same manner as EXAMPLE 1.

The resulting product is identified, in the same manner as EXAMPLE 1, as a new acrylic ester derivative of the present invention, namely, methyl-α-(galactosidemethyl)acrylate. The yield of methyl-α-(galactosidemethyl)acrylate evaluated by a predetermined method is 60 percent by mole.

The conditions and result of the above reaction are set forth in TABLEs 1-3 and 2-3 below. The absorption wave number of the infrared absorption spectrum and the result of the elemental analysis of methyl-α-(galactosidemethyl) acrylate are set forth in TABLE 3-2 below.

EXAMPLE 19

Herein, 58.0 g of methyl-α-hydroxymethylacrylate, 0.10 g of hydroquinone, and 20 g of toluene are stirred in a reactor of the same type used in EXAMPLE 1. Then, 17.7 g of N-acetylglucosamine and 2.0 g of boron trifluoride ethyl ether complex are added, and the reactant solution is heated slowly with stirring. Further, the reactant solution is subject to stirring for one hour at 115° C. under a normal pressure. Water produced as a result of the reaction is removed from the reactant by azeotropy using toluene, or the Dean and Stark method.

When the reaction ends, the reactant solution is neutralized with a potassium carbonate anhydride. The resulting neutralized solution is separated and purified in the same manner as EXAMPLE 1.

The resulting product is identified, in the same manner as EXAMPLE 1, as a new acrylic ester derivative of the present invention, namely, methyl-α-(2-acetamide-2-deoxyglucosidemethyl)acrylate. The yield of methyl-α-(2-acetamide-2-deoxyglucosidemethyl)acrylate evaluated by a predetermined method is 62 percent by mole.

The conditions and result of the above reaction are set forth in TABLEs 1-3 and 2-3 below. The absorption wave number of the infrared absorption spectrum and the result of the elemental analysis of methyl-α-(2-acetamide-2-deoxyglucosidemethyl)acrylate are set forth in TABLE 3-3 below.

EXAMPLE 20

Herein, 58.0 g of methyl-α-hydroxymethylacrylate and 0.02 g of p-benzoquinone are stirred in a reactor of the same type used in EXAMPLE 1. Then, 12.8 g of lactose and 10.0 g of ion exchange resin (Diaion SK) are added, and the reactant solution is heated slowly with stirring. Further, the reactant solution is subject to stirring for six hours at 90° C. under a normal pressure.

When the reaction ends, the ion exchange resin is removed from the reaction solution through filtration. The resulting filtrate is separated and purified in the same manner as EXAMPLE 1.

The resulting product is identified, in the same manner as EXAMPLE 1, as a new acrylic ester derivative of the present invention, namely, methyl-α-(lactosidemethyl)acrylate. The yield of methyl-α-(lactosidemethyl)acrylate evaluated by a predetermined method is 44 percent by mole.

The conditions and result of the above reaction are set forth in TABLEs 1-3 and 2-3 below. The absorption wave number of the infrared absorption spectrum and the result of the elemental analysis of methyl-α-(lactosidemethyl) acrylate are set forth in TABLE 3-3 below.

EXAMPLE 21

Herein, 51.0 g of α-hydroxymethylacrylate serving as an acrylic ester, 0.10 g of p-benzoquinone, and 100 g of N,N-dimethylformamide serving as a solvent are stirred in a reactor of the same type used in EXAMPLE 1. Then, 9.0 g of glucose and 1.5 g of paratoluenesulfonic acid monohydrate are added, and the reactant solution is heated slowly with stirring. Further, the reactant solution is subject to stirring for three hours at 100° C. under a normal pressure.

When the reaction ends, the reactant solution is neutralized with a 2N-sodium hydroxide solution. The resulting neutralized solution is concentrated, separated, and purified in the same manner as EXAMPLE 1.

The resulting product is identified, in the same manner as EXAMPLE 1, as a new acrylic ester derivative of the present invention, namely, α-(glucosidemethyl)acrylate. The yield of α-(glucosidemethyl)acrylate evaluated by a predetermined method is 38 percent by mole.

The conditions and result of the above reaction are set forth in TABLEs 1-3 and 2-3 below. The absorption wave

EXAMPLE 22

Herein, 62.0 g of sodium-α-hydroxymethylacrylate serving as an acrylic ester, 0.06 g of hydroquinone monomethyl ether, and 100 g of N,N-dimethylformamide are stirred in a reactor of the same type used in EXAMPLE 1. Then, 12.0 g of glucose and 12.4 g of sulfuric acid are added, and the reactant solution is heated slowly with stirring. Further, the reactant solution is subject to stirring for three hours at 95° C. under a normal pressure.

When the reaction ends, the reactant solution is neutralized with a 2N-sodium hydroxide water solution. The resulting neutralized solution is concentrated, separated, and purified in the same manner as EXAMPLE 1.

The resulting product is identified, in the same manner as EXAMPLE 1, as a new acrylic ester derivative of the present invention, namely, sodium-α-(glucosidemethyl)acrylate. The yield of sodium-α-(glucosidemethyl)acrylate evaluated by a predetermined method is 40 percent by mole.

The conditions and result of the above reaction are set forth in TABLEs 1-3 and 2-3 below. The absorption wave number of the infrared absorption spectrum and the result of the elemental analysis of sodium-α-(glucosidemethyl) acrylate are set forth in TABLE 3-3 below.

TABLE 1-1

| EMBODIMENT | ACRYLIC ESTER (g) | SACCHARIDE/ ALKYL-GLYCOSIDE (g) | | POLYMERIZATION INHIBITOR (g) | |
|---|---|---|---|---|---|
| 1 | ETHYL-α-HYDROXYMETHYL-ACRYLATE | 65.0 | GLUCOSE | 18.0 | p-t-BUTYL-CATECHOL | 1.30 |
| 2 | | | GLUCOSE | 9.0 | HYDROQUINONE | 0.07 |
| 3 | | | METHYL-GLUCOSIDE | 19.4 | HYDROQUINONE MONOMETHYL ETHER | 0.65 |
| 4 | | | GALACTOSE | 12.0 | p-t-BUTYL-CATECHOL | 0.10 |
| 5 | | | ETHYL GALACTOSIDE | 20.8 | PHENOTHIAZINE | 0.03 |
| 6 | | | N-ACETYL-GLUCOSAMINE | 22.1 | HYDROQUINONE MONOMETHYL ETHER | 0.02 |
| 7 | | | XYLOSE | 22.5 | HYDROQUINONE | 0.65 |
| 8 | | | METHYLXYLOSIDE | 8.2 | p-BENZOQUINONE | 0.04 |
| 9 | | | MALTOSE | 18.0 | p-t-BUTYL-CATECHOL | 0.08 |

| EMBODIMENT | CATALYST | (g) | SOLVENT/ AZEOTROPIC SOLVENT (g) | |
|---|---|---|---|---|
| 1 | PTS | 0.7 | — | |
| 2 | HYDROCHLORIC ACID | 1.0 | TOLUENE | 80 |
| 3 | TUNGSTO-PHOSPHORIC ACID | 1.0 | CHLORO-BENZENE | 100 |
| 4 | BF₃ | 2.6 | CYCLO-HEXANE | 10 |
| 5 | MOLYBDO-PHOSPHORIC ACID | 1.6 | — | |
| 6 | PTS | 3.0 | CYCLO-HEXANE | 15 |
| 7 | ION EXCHANGE RESIN* | 12.0 | — | |
| 8 | MOLYBDO-SILICIC ACID | 0.8 | — | |
| 9 | SULFURIC ACID | 0.5 | HEPTANE | 10 |

PTS: PARATOLUENESULFONIC ACID MONOHYDRATE
BF₃: BORON TRIFLUORIDE ETHYL ETHER COMPLEX
*: DOWEX-50W OF THE DOW CHEMICAL CO.

TABLE 1-2

| EMBODIMENT | ACRYLIC ESTER (g) | | SACCHARIDE/ ALKYL-GLYCOSIDE (g) | | POLYMERIZATION INHIBITOR (g) | |
|---|---|---|---|---|---|---|
| 10 | ETHYL-α-HYDROXYMETHYL-ACRYLATE | 65.0 | LACTOSE | 17.1 | HYDROQUINONEMO NOMETHYL ETHER | 0.30 |
| 11 | | | MALTOPETAOSE | 41.4 | PHENOTHIAZINE | 0.25 |
| 12 | n-BUTYL-α-HYDROXYMETHYL-ACRYLATE | 79.0 | GLUCOSE | 13.5 | HYDROQUINONE MONOMETHYL ETHER | 0.39 |
| 13 | | | GALACTOSE | 18.0 | HYDROQUINONE | 0.79 |
| 14 | | | N-ACETYL-GLUCOSAMINE | 16.6 | p-BENZOQUINONE | 0.06 |
| 15 | | | XYLOSE | 15.0 | PHENOTHIAZINE | 0.08 |
| 16 | | | MALTOSE | 22.5 | HYDROQUINONE MONOMETHYL ETHER | 0.10 |

| EMBODIMENT | CATALYST | (g) | SOLVENT/ AZEOTROPIC SOLVENT (g) | |
|---|---|---|---|---|
| 10 | ION EXCHANGE RESIN** | 13.0 | o-XYLENE | 75 |
| 11 | HYDROCHLORIC ACID | 1.0 | — | |
| 12 | ION EXCHANGE RESIN* | 15.0 | — | |
| 13 | PTS | 1.0 | CHLOROBENZENE | 85 |
| 14 | HYDROCHLORIC ACID | 0.5 | TOLUENE | 110 |
| 15 | BF₃ | 2.0 | BENZENE | 70 |
| 16 | ION EXCHANGE RESIN* | 15.0 | — | |

PTS: PARATOLUENESULFONIC ACID MONOHYDRATE
*: DOWEX-50W OF THE DOW CHEMICAL CO.
BF₃: BORON TRIFLUORIDE ETHYL ETHER COMPLEX
**: DIAION SK OF MITSUBISHI CHEMICAL CORPORATION

TABLE 1-3

| EMBODIMENT | ACRYLIC ESTER (g) | | SACCHARIDE/ ALKYL-GLYCOSIDE (g) | | POLYMERIZATION INHIBITOR (g) | |
|---|---|---|---|---|---|---|
| 17 | METHYL-α-HYDROXYMETHYL-ACRYLATE | 58.0 | GLUCOSE | 12.0 | PHENOTHIAZINE | 0.06 |
| 18 | | | GALACTOSE | 13.5 | HYDROQUINONE MONOMETHYL ETHER | 0.58 |
| 19 | | | N-ACETYL-GLUCOSAMINE | 17.7 | HYDROQUINONE | 0.10 |
| 20 | | | LACTOSE | 12.8 | p-BENZOQUINONE | 0.02 |
| 21 | α-HYDROXY-METHYLACRYLATE | 51.0 | GLUCOSE | 9.0 | p-BENZOQUINONE | 0.10 |
| 22 | SODIUM-α-HYDROXYMETHYL-ACRYLATE | 62.0 | GLUCOSE | 12.0 | HYDROQUINONE MONOMETHYL ETHER | 0.06 |

| EMBODIMENT | CATALYST | (g) | SOLVENT/ AZEOTROPIC SOLVENT (g) | |
|---|---|---|---|---|
| 17 | PTS | 0.6 | CYCLOHEXANE | 8 |
| 18 | ION EXCHANGE RESIN* | 11.0 | TOLUENE | 100 |
| 19 | BF₃ | 2.0 | TOLUENE | 20 |
| 20 | ION EXCHANGE RESIN** | 10.0 | — | |
| 21 | PTS | 1.5 | N,N-DIMETHYL-FORMAMIDE | 100 |
| 22 | SULFURIC ACID | 12.4 | | |

TABLE 1-3-continued

PTS: PARATOLUENESULFONIC ACID MONOHYDRATE
*: DOWEX-50W OF THE DOW CHEMICAL CO.
$BF_3$: BORON TRIFLUORIDE ETHYL ETHER COMPLEX
**: DIAION SK OF MITSUBISHI CHEMICAL CORPORATION

TABLE 2-1

| EMBODIMENT | TEMPERATURE (°C.) | PRESSURE (mmHg) | TIME (hr) | NEUTRALIZER | REMOVAL OF ALCOHOL | ACRYLIC ESTER DERIVATIVE | YIELD (MOLE %) |
|---|---|---|---|---|---|---|---|
| 1 | 100 | 760 | 2 | 2N-SODIUM HYDROXIDE W. SOLUTION | — | ETHYL-α-(GLUCOSIDE-METHYL)-ACRYLATE | 63 |
| 2 | 90 | 350 | 2 | SODIUM CARBONATE ANHYDRIDE | VACUUM AZEOTROPY | | 68 |
| 3 | REFLUX | 760 | 2 | 2N-SODIUM HYDROXIDE W. SOLUTION | — | | 60 |
| 4 | 95 | 760 | 2 | 2N-POTASSIUM HYDROXIDE W. SOLUTION | AZEOTROPY | ETHYL-α-(GALACTOSIDE-METHYL)-ACRYLATE | 68 |
| 5 | 80 | 760 | 2.5 | 1N-POTASSIUM HYDROXIDE W. SOLUTION | — | | 62 |
| 6 | 90 | 760 | 2 | 1N-SODIUM HYDROXIDE W. SOLUTION | AZEOTROPHY | ETHYL-α-(2-ACETAMIDE-2-DEOXY-GLUCOSIDE-METHYL)-ACRYLATE | 59 |
| 7 | 100 | 760 | 5 | — | — | ETHYL-α-(XYLOSIDE-METHYL)-ACRYLATE | 52 |
| 8 | 90 | 600 | 2 | SODIUM CARBONATE ANHYDRIDE | VACUUM | | 58 |
| 9 | 100 | 760 | 3 | 2N-SODIUM HYDROXIDE W. SOLUTION | AZEOTROPHY | ETHYL-α-(MALTOSIDE-METHYL)-ACRYLATE | 50 |

W. SOLUTION: WATER SOLUTION

TABLE 2-2

| EMBODIMENT | TEMPERATURE (°C.) | PRESSURE (mmHg) | TIME (hr) | NEUTRALIZER | REMOVAL OF ALCOHOL | ACRYLIC ESTER DERIVATIVE | YIELD (MOLE %) |
|---|---|---|---|---|---|---|---|
| 10 | 95 | 160 | 6 | — | VACUUM AZEOTROPY | ETHYL-α-(LACTOSIDE-METHYL)-ACRYLATE | 48 |
| 11 | 85 | 760 | 3 | SODIUM CARBONATE ANHYDRIDE | — | ETHYL-α-(MALTOPENTA-OSIDEMETHYL)-ACRYLATE | 42 |
| 12 | 95 | 760 | 5 | — | — | n-BUTYL-α-(GLUCOSIDE-METHYL)-ACRYLATE | 60 |
| 13 | REFLUX | 760 | 2 | SODIUM CARBONATE ANHYDRIDE | — | n-BUTYL-α-(GALACTOSIDE-METHYL)-ACRYLATE | 61 |
| 14 | 100 | 550 | 1.5 | 2N-SODIUM HYDROXIDE W.SOLUTION | VACUUM AZEOTROPY | n-BUTYL-α-(2-ACETAMIDE-2-DEOXY-GLUCOSIDE-METHYL)-ACRYLATE | 60 |
| 15 | REFLUX | 760 | 2 | 1N-POTASSIUM HYDROXIDE | — | n-BUTYL-α-(XYLOSIDE-METHYL)- | 53 |

TABLE 2-2-continued

| EMBODIMENT | TEMPERATURE (°C.) | PRESSURE (mmHg) | TIME (hr) | NEUTRALIZER | REMOVAL OF ALCOHOL | ACRYLIC ESTER DERIVATIVE | YIELD (MOLE %) |
|---|---|---|---|---|---|---|---|
| 16 | 100 | 760 | 6 | W.SOLUTION — | — | ACRYLATE n-BUTYL-α-(MALTOSIDE-METHYL)-ACRYLATE | 42 |

W.SOLTUION: WATER SOLTUION

TABLE 2-3

| EMBODIMENT | TEMPERATURE (°C.) | PRESSURE (mmHg) | TIME (hr) | NEUTRALIZER | REMOVAL OF ALCOHOL | ACRYLIC ESTER DERIVATIVE | YIELD (MOLE %) |
|---|---|---|---|---|---|---|---|
| 17 | 100 | 760 | 2 | SODIUM CARBONATE ANHYDRIDE | AZEOTROPY | METHYL-α-(GLUCOSIDE-METHYL)-ACRYLATE | 67 |
| 18 | 100 | 550 | 5 | — | VACUUM AZEOTROPY | METHYL-α-(GALACTOSIDE-METHYL)-ACRYLATE | 60 |
| 19 | 115 | 760 | 1 | POTASSIUM CARBONATE ANHYDRIDE | AZEOTROPY | METHYL-α-(2-ACETAMIDE-2-DEOXYGLUCOSIDE-METHYL)-ACRYLATE | 62 |
| 20 | 90 | 760 | 6 | — | — | METHYL-α-(LACTOSIDE-METHYL)-ACRYLATE | 44 |
| 21 | 100 | 760 | 3 | 2N-SODIUM HYDROXIDE W. SOLUTION | — | α-(GLUCOSIDE-METHYL)-ACRYLATE | 38 |
| 22 | 95 | 760 | 3 | 2N-SODIUM HYDROXIDE W. SOLUTION | — | SODIUM-α-(GLUCOSIDE-METHYL)ACRYLATE | 40 |

W. SOLUTION: WATER SOLUTION

TABLE 3-1

| ACRYLIC ESTER DERIVATIVE | ABSORPTION WAVE NUMBER OF INFRARED ABSORPTION SPECTRUM (cm$^{-1}$) | ELEMENTAL ANALYSIS (WT %) | MEASURED VALUE | CALCULATED VALUE |
|---|---|---|---|---|
| ETHYL-α-(GLUCOSIDEMETHYL)-ACRYLATE | 3600–3000, 2950, 1710, 1640, 1450, 1050 | C; H; | 49.35 6.84 | 49.32 6.85 |
| ETHYL-α-(GALACTOSIDEMETHYL)-ACRYLATE | 3600–3000, 2950, 1710, 1640, 1450, 1050 | C; H; | 49.40 6.88 | 49.32 6.85 |
| ETHYL-α-(2-ACETAMIDE-2-DEOXY-GLUCOSIDEMETHYL)ACRYLATE | 3600–3000, 3200, 2950, 1710, 1640, 1620, 1450, 1050 | C; H; N; | 50.40 6.85 4.11 | 50.45 6.91 4.20 |
| ETHYL-α-(XYLOSIDEMETHYL)-ACRYLATE | 3600—3000, 2950, 1710, 1640, 1450, 1050 | C; H; | 50.22 6.99 | 50.38 6.87 |
| ETHYL-α-(MALTOSIDEMETHYL)-ACRYLATE | 3600–3000, 2950, 1710, 1640, 1450, 1050 | C; H; | 47.39 6.66 | 47.58 6.61 |
| ETHYL-α-(LACTOSIDEMETHYL)-ACRYLATE | 3600–3000, 2950, 1710, 1640, 1450, 1050 | C; H; | 47.35 6.72 | 47.58 6.61 |
| ETHYL-α-(MALTOPENTAOSIDE-METHYL)ACRYLATE | 3600–3000, 2950, 1710, 1640, 1450, 1050 | C; H; | 45.37 6.80 | 45.76 6.78 |

TABLE 3-2

| ACRYLIC ESTER DERIVATIVE | ABSORPTION WAVE NUMBER OF INFRARED ABSOPTION SPECTRUM (cm$^{-1}$) | ELEMENTAL ANALYSIS (WT %) | MEASURED VALUE | CALCULATED VALUE |
|---|---|---|---|---|
| n-BUTYL-α-(GLUCOSIDEMETHYL)-ACRYLATE | 3600–3000, 2950, 1710, 1640, 1450, 1050 | C; H; | 51.20 7.33 | 50.98 7.19 |

TABLE 3-2-continued

| ACRYLIC ESTER DERIVATIVE | ABSORPTION WAVE NUMBER OF INFRARED ABSOPTION SPECTRUM (cm$^{-1}$) | ELEMENTAL ANALYSIS (WT %) | | |
|---|---|---|---|---|
| | | | MEASURED VALUE | CALCULATED VALUE |
| n-BUTYL-α-(GALACTOSIDEMETHYL)-ACRYLATE | 3600–3000, 2950, 1710, 1640, 1450, 1050 | C; H; | 51.00 7.25 | 50.98 7.19 |
| n-BUTYL-α-(2-ACETAMIDE-2-DEOXYGLUCOSIDEMETHYL)-ACRYLATE | 3600–3000, 3200, 2950, 1710, 1640, 1620, 1450, 1050 | C; H; N; | 51.85 7.26 4.11 | 51.87 7.20 4.03 |
| n-BUTYL-α-(XYLOSIDEMETHYL)-ACRYLATE | 3600–3000, 2950, 1710, 1640, 1450, 1050 | C; H; | 51.99 7.21 | 52.17 7.25 |
| n-BUTYL-α-(MALTOSIDEMETHYL)-ACRYLATE | 3600–3000, 2950, 1710, 1640, 1450, 1050 | C; H; | 49.12 6.88 | 48.72 6.84 |
| METHYL-α-(GLUCOSIDEMETHYL)-ACRYLATE | 3600–3000, 2950, 1710, 1640, 1450, 1050 | C; H; | 47.47 6.50 | 47.48 6.47 |
| METHYL-α-(GALACTOSIDEMETHYL)-ACRYLATE | 3600–3000, 2950, 1710, 1640, 1450, 1050 | C; H; | 47.55 6.54 | 47.48 6.47 |

TABLE 3-3

| ACRYLIC ESTER DERIVATIVE | ABSORPTION WAVE NUMBER OF INFRARED ABSORPTION SPECTRUM (cm$^{-1}$) | ELEMENTAL ANALYSIS (WT %) | |
|---|---|---|---|
| | | MEASURED VALUE | CALCULATED VALUE |
| METHYL-α-(2-ACETAMIDE-2-DEOXYGLUCOSIDEMETHYL)-ACRYLATE | 3600–3000, 3200, 2950, 1710, 1640, 1620, 1450, 1050 | C; 49.12 H; 6.47 N; 4.42 | 48.90 6.58 4.39 |
| METHYL-α-(LACTOSIDEMETHYL)-ACRYLATE | 3600–3000, 2950, 1710, 1640, 1450, 1050 | C; 46.62 H; 6.22 | 46.36 6.36 |
| α-(GLUCOSIDEMETHYL)-ACRYLATE | 3600–3000, 2950, 1690, 1450, 1050 | C; 45.33 H; 5.71 | 45.45 6.06 |
| SODIUM-α-(GLUCOSIDEMETHYL)-ACRYLATE | 3600–3000, 2950, 1640, 1600, 1450, 1050 | C; 41.58 H; 5.52 | 41.96 5.24 |

EXAMPLE 23

Herein, 65.0 g of ethyl-α-hydroxymethylacrylate, 0.50 g of hydroquinone monomethyl ether, and 10 g of cyclohexane are stirred in a reactor of the same type used in EXAMPLE 1. Then, 50.0 g of soluble starch serving as a saccharide containing a hemiacetal hydroxyl group, and 1.0 g of paratoluenesulfonic acid monohydrate are added, and the reactant solution is heated slowly with stirring. Further, the reactant solution is subject to stirring for four hours at 95° C. under a normal pressure. Water produced as a result of the reaction is removed from the reactant by azeotropy using cyclohexane, or the Dean and Stark method.

When the reaction ends, the reactant solution is neutralized with a 2N-sodium hydroxide water solution. The resulting neutralized solution is analyzed using HPLC under predetermined conditions.

Then, the peak of the raw material, ethyl-α-hydroxymethylacrylate, is lowered, and in turn, the peak of a new acrylic ester derivative of the present invention, namely, ethyl-α-(amilosidemethyl)acrylate is acknowledged. The iodine number of the reactant solution is evaluated before and after the reaction and no variance is acknowledged.

EXAMPLE 24

Herein, 65.0 g of ethyl-α-hydroxymethylacrylate, 0.03 g of hydroquinone, 0.3 mg of 2,2'-oxamidobis[ethyl-3-(3,5-di-t-butyl-4-hydroxyphenyl)propionate] serving as a polymerization inhibitor (chelating agent), and 20 g of cyclohexane are stirred in a reactor of the same type used in EXAMPLE 1. Then, 18.0 g of glucose and 0.7 g of paratoluenesufonic acid monohydrate are added, and the reactant solution is mixed with stirring. On the other hand, a mixed gas is prepared by mixing an oxygen gas and a nitrogen gas in a capacity ratio of 7:93.

The mixed gas is blown into the reactor to adjust the density of the molecular oxygens in the gaseous phase in the reactor to 5 percent by capacity while the reactant solution is slowly heated. Further, the reactant solution is subject to stirring for two hours at 95° C. Water produced as a result of the reaction is removed from the reactant by azeotropy using cyclohexane, or the Dean and Stark method. During the above reaction, neither increase in viscosity of the reactant solution nor production of a polymer is acknowledged.

When the reaction ends, the reactant solution is neutralized with a 2N-sodium hydroxide water solution, and the resulting neutralized solution is vacuum concentrated. Then, the yield of ethyl-α-(glucosidemethyl)acrylate in the resulting concentrated solution evaluated using HPLC under predetermined conditions is 77 percent by mole.

EXAMPLE 25

Herein, 65.0 g of ethyl-α-hydroxymethylacrylate, 0.02 g of tetrakis[methylene-3-(3',5'-di-t-butyl-4'-hydroxyphenyl) propionate)]methane serving as a polymerization inhibitor (first-order oxidation inhibitor), and 0.02 g of distearyl-3, 3'-thiodipropionate serving as a polymerization inhibitor (second-order oxidation inhibitor) are stirred in a reactor of the same type used in EXAMPLE 1. Then, 18.0 g of glucose and 0.7 g of paratoluenesufonic acid monohydrate are added, and the reactant solution is mixed with stirring. On the other hand, a mixed gas is prepared by mixing an oxygen gas and a nitrogen gas in a capacity ratio of 7:93.

The mixed gas is blown into the reactor to adjust the density of the molecular oxygens in the gaseous phase in the reactor to 5 percent by capacity while the reactant solution is slowly heated. Further, the reactant solution is subject to stirring for two hours at 90° C. under 600 mmHg. Water produced as a result of the reaction is removed from the reactant. During the above reaction, neither increase in viscosity of the reactant solution nor production of a polymer is acknowledged.

When the reaction ends, the reactant solution is neutralized with a 2N-sodium hydroxide water solution, and the resulting neutralized solution is vacuum concentrated. Then, the yield of ethyl-α-(glucosidemethyl)acrylate in the resulting concentrated solution is evaluated, in the same manner as EXAMPLE 24, as 75 percent by mole.

EXAMPLE 26

Herein, 65.0 g of ethyl-α-hydroxymethylacrylate, 0.03 g of p-t-butylcatechol serving as a polymerization inhibitor (first-order oxidation inhibitor), 0.0 g of 2,2'-oxamidobis [ethyl-3-(3,5-di-t-butyl-4-hydroxyphenyl)propionate], 0.01 g of N-nitrosophenylhydroxyamine aluminium, and 80 g of toluene are stirred in a reactor of the same type used in EXAMPLE 1. Then, 18.0 g of glucose and 0.7 g of paratoluenesufonic acid monohydrate are added, and the reactant solution is heated slowly with stirring. When the reactant solution is heated up to 75° C., the reactor is vacuumed and the reactant solution is subject to stirring for two hours at 90° C. under 350 mmHg. Water produced as a result of the reaction is removed from the reactant by azeotropy using toluene, or the Dean and Stark method. During the above reaction, neither increase in viscosity of the reactant solution nor production of a polymer is acknowledged.

When the reaction ends, the reactant solution is neutralized with a 2N-sodium hydroxide water solution, and the resulting neutralized solution is vacuum concentrated. Then, the yield of ethyl-α-(glucosidemethyl)acrylate in the resulting concentrated solution is evaluated, in the same manner as EXAMPLE 24, as 78 percent by mole.

EXAMPLE 27

Herein, 65.0 g of ethyl-α-hydroxymethylacrylate, 0.03 g of hydroquinone, 0.02 g of nitrilotriacetic acid serving as a polymerization inhibitor (chleating agent), and 20 g of cyclohexane are stirred in a reactor of the same type used in EXAMPLE 1. Then, 18.0 g of glucose and 0.7 g of paratoluenesufonic acid monohydrate are added, and the reactant solution is mixed with stirring. On the other hand, a mixed gas is prepared by mixing a nitrogen monoxide gas and a nitrogen gas in a capacity ratio of 5:95.

The mixed gas is blown into the reactor to adjust the density of the molecular nitrogen monoxides in the gaseous phase in the reactor to 5 percent by capacity while the reactant solution is slowly heated. Further, the reactant solution is subject to stirring for two hours at 80° C. Water produced as a result of the reaction is removed from the reactant by azeotropy using cyclohexane, or the Dean and Stark method. During the above reaction, neither increase in viscosity of the reactant solution nor production of a polymer is acknowledged.

When the reaction ends, the reactant solution is neutralized with a 2N-sodium hydroxide solution, and the resulting neutralized solution is vacuum concentrated. Then, the yield of ethyl-α-(glucosidemethyl)acrylate in the resulting concentrated solution is evaluated, in the same manner as EXAMPLE 24, as 74 percent by mole.

COMPARATIVE EXAMPLE 1

A reaction is carried out in the same manner as EXAMPLE 24 except that neither hydroquinon serving as a polymerization inhibitor (first-order oxidation inhibitor) nor 2,2'-oxamidobis[ethyl-3-(3,5-di-t-butyl-4-hydroxyphenyl) propionate] serving as a polymerization inhibitor (chleating agent) is used. Then, the reactant solution turns into gel as the reaction proceeds, and can no longer be stirred. This indicates that when no polymerization inhibitor is used, the reactant solution produces a polymer.

COMPARATIVE EXAMPLE 2

Herein, 65.0 g of ethyl-α-hydroxymethylacrylate and 0.5 mg of hydroquinone are stirred in a reactor of the same type used in EXAMPLE 1. Then, 18.0 g of glucose and 0.7 g of paratoluenesufonic acid monohydrate are added, and the reactant solution is heated slowly with stirring. Further, the reactant solution is subject to stirring for two hours at 100° C. During the above reaction, increase in viscosity of the reactant solution and production of a polymer are acknowledged.

When the reaction ends, the reactant solution is neutralized with a 2N-sodium hydroxide solution, and the resulting neutralized solution is vacuum concentrated. Then, the yield of ethyl-α-(glucosidemethyl)acrylate in the resulting concentrated solution is evaluated, in the same manner as EXAMPLE 24, as 23 percent by mole. This indicates that polymerization of the reactant solution can not be curbed in a satisfactory manner if a polymerization inhibitor is added insufficiently.

EXAMPLE 28

Herein, 5.8 g of ethyl-α-(glucosidemethyl)acrylate, the acrylic ester derivative produced in EXAMPLE 1, and 0.002 g of benzoyl peroxide serving as a polymerization initiator are placed in a test tube and test tube is sealed airtight after nitrogen substitution. Then, the content is subject to heating at 80° C. to let the same undergo polymerization, and a polymer of ethyl-α-(glucosidemethyl)acrylate is produced as a result.

Figure 4:
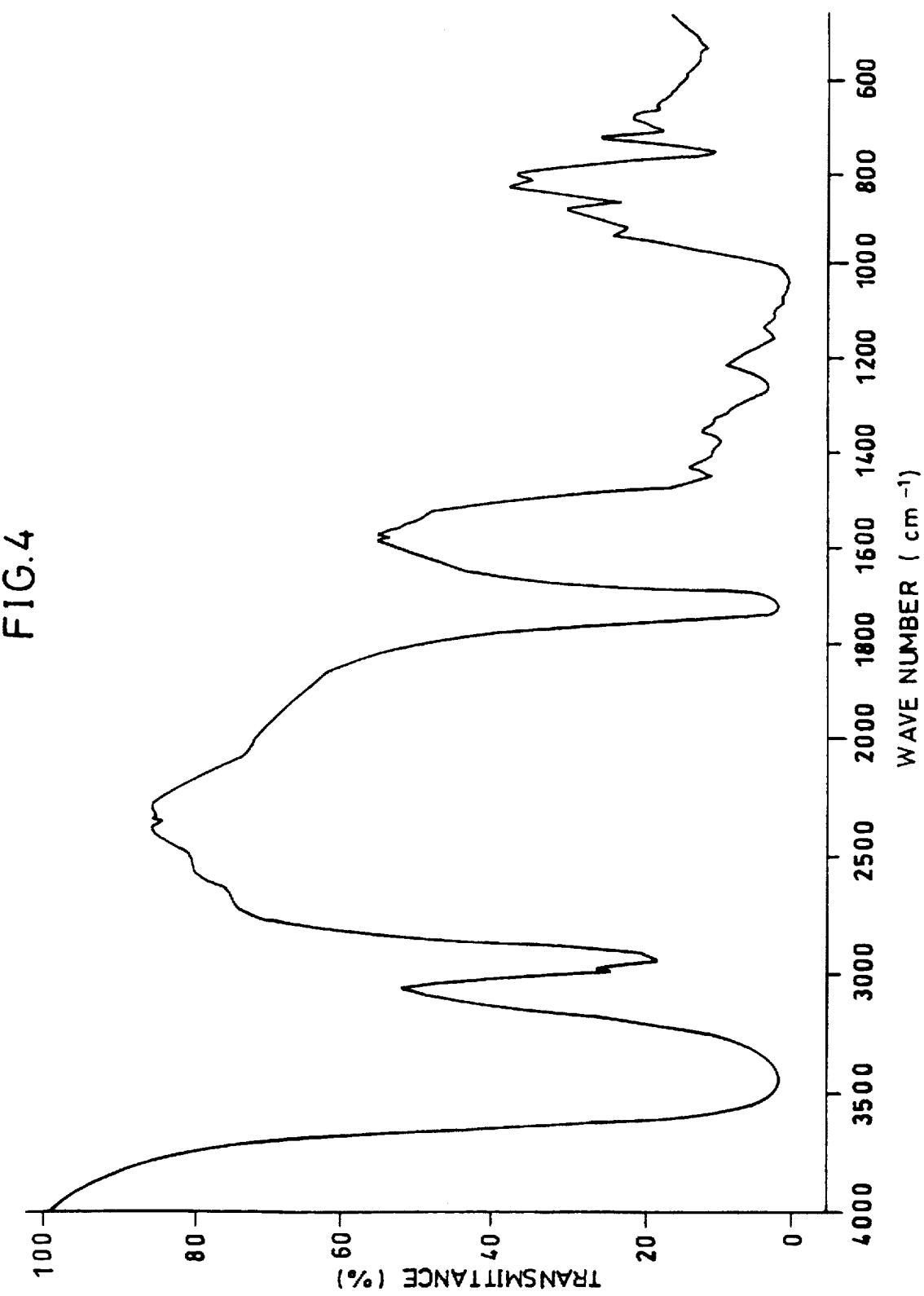
FIG. 4 is a view showing an infrared absorption spectrum of a polymer produced in EXAMPLE 28 by letting the above reaction product undergo polymerization.

The resulting polymer is identified by measuring $^1$H-NMR, $^{13}$C-NMR, and the absorption wave number of the infrared absorption spectrum of the same. Then, the polymer is identified as a new acrylic-ester-based polymer of the present invention. The number average molecular amount (Mn) of the acrylic-ester-based polymer evaluated by the Gel Permeation Chromatography (GPC) is 1,240,000. The infrared absorption spectrum of the above polymer is set forth in FIG. 4.

EXAMPLE 29

Herein, 5.8 g of ethyl-α-(glucosidemethyl)acrylate produced in EXAMPLE 2, 2.0 g of methylmethacrylate serving as a monomer, and 0.004 g of 2,2'-azobisisobutyronitrile serving as a polymerization initiator are placed in a test tube and the test tube is sealed airtight after nitrogen substitution. Then, a copolymer is produced through a copolymerization in a similar manner to the polymerization of EXAMPLE 28.

Figure 5:
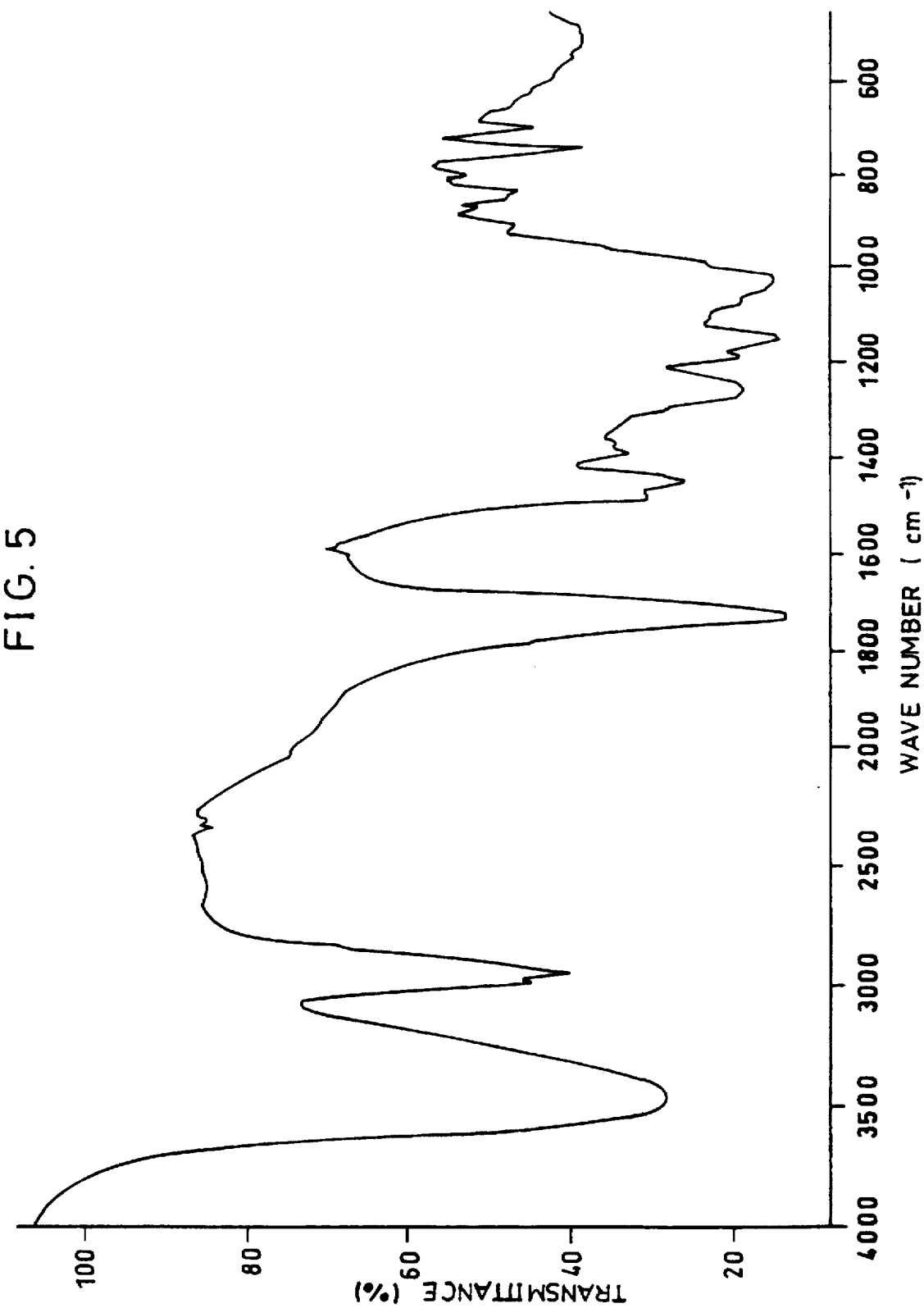
FIG. 5 is a view showing an infrared absorption spectrum of a copolymer produced in EXAMPLE 29.

The resulting copolymer is identified, in the same manner as EXAMPLE 28, as a new acrylic-ester-based polymer of the present invention. The number average molecular amount of the acrylic-ester-based polymer evaluated by the Gel Permeation Chromatography is 1,087,000. The infrared absorption spectrum of the above copolymer is set forth in FIG. 5.

EXAMPLE 30

Herein, 5.8 g of ethyl-α-(glucosidemethyl)acrylate produced in EXAMPLE 3, 2.1 g of styrene serving as a monomer, and 0.004 g of 2,2'-azobisisobutyronitrile are placed in a test tube and the test tube is sealed airtight after nitrogen substitution. Then, a copolymer is produced through a copolymerization in a similar manner to the polymerization of EXAMPLE 28.

Figure 6:
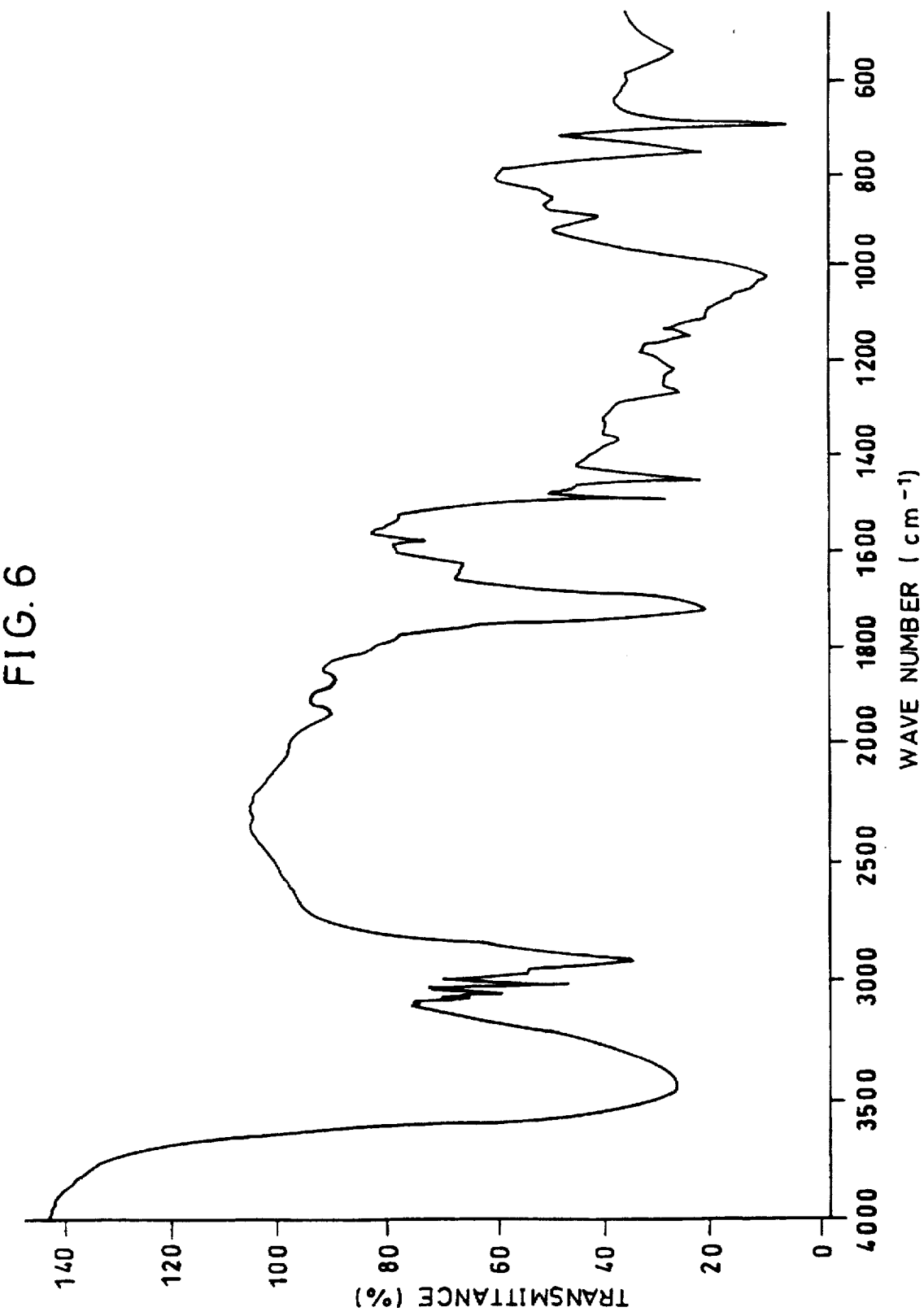
FIG. 6 is a view showing an infrared absorption spectrum of a copolymer produced in EXAMPLE 30.

The resulting copolymer is identified, in the same manner as EXAMPLE 28, as a new acrylic-ester-based polymer of the present invention. The number average molecular amount of the acrylic-ester-based polymer evaluated by the Gel Permeation Chromatography is 1,115,000. The infrared absorption spectrum of the above copolymer is set forth in FIG. 6.

EXAMPLE 31

Herein, 5.8 g of ethyl-α-(galactosidemethyl)acrylate, the acrylic ester derivative produced in EXAMPLE 4, and 0.002 g of benzoyl peroxide are placed in a test tube and the test tube is sealed airtight after nitrogen substitution. Then, a polymer is produced in the same manner as EXAMPLE 28.

Figure 7:
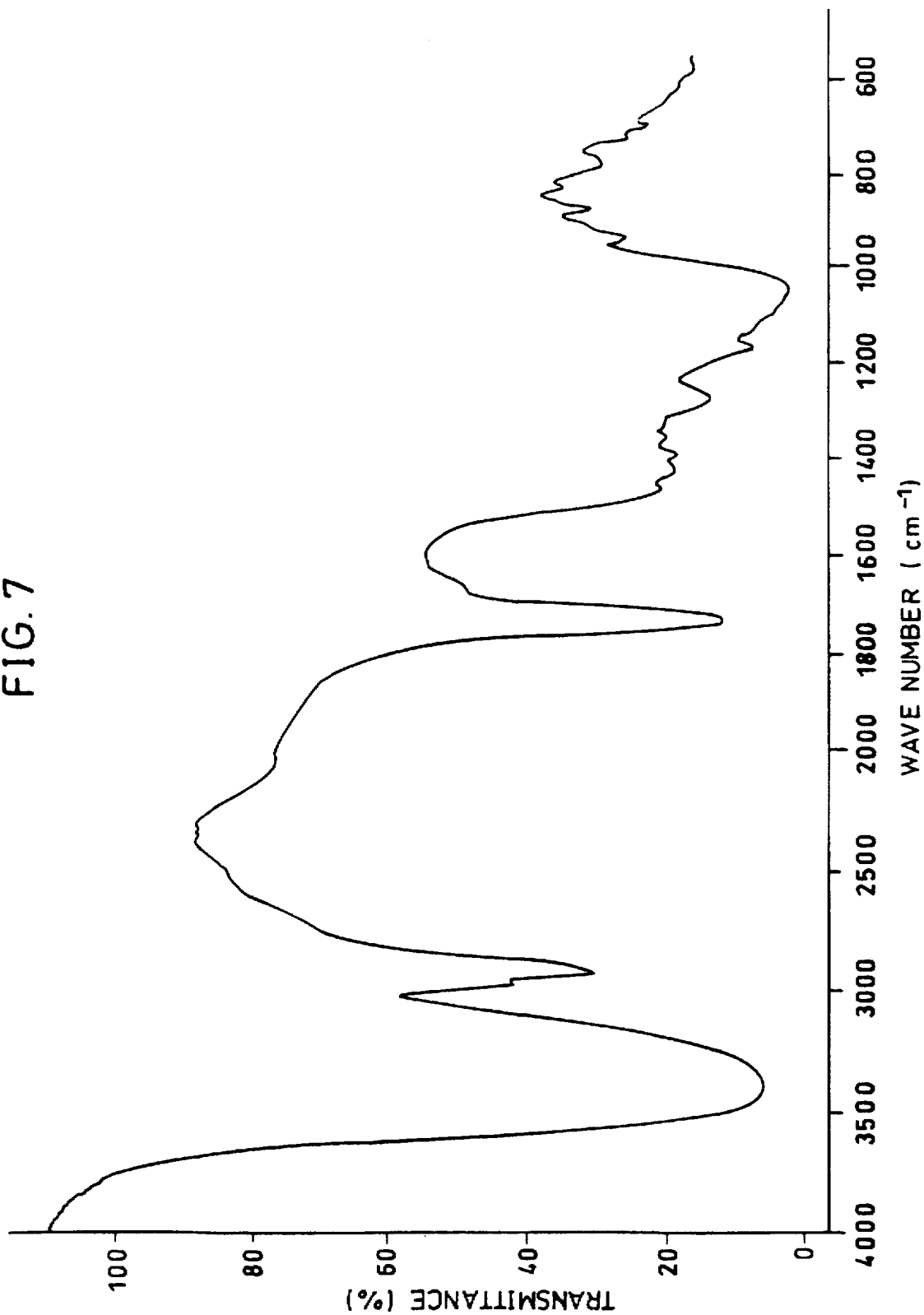
FIG. 7 is a view showing an infrared absorption spectrum of a polymer produced in EXAMPLE 31.

The resulting polymer is identified, in the same manner as EXAMPLE 28, as a new acrylic-ester-based polymer of the present invention. The number average molecular amount of the acrylic-ester-based polymer evaluated by the Gel Permeation Chromatography is 39,000. The infrared absorption spectrum of the above polymer is set forth in FIG. 7.

EXAMPLE 32

Herein, 4.0 g of ethyl-α-(glucosidemethyl)acrylate produced in EXAMPLE 2, 1.0 g of acrylic acid and 3.0 g of sodium acrylate both serving as a monomer, and 0.004 g of 2,2'-azobisisobutyronitrile are placed in a test tube and the test tube is sealed airtight after nitrogen substitution. Then, a copolymer is produced through a copolymerization in a similar manner to the polymerization of EXAMPLE 28.

Figure 8:
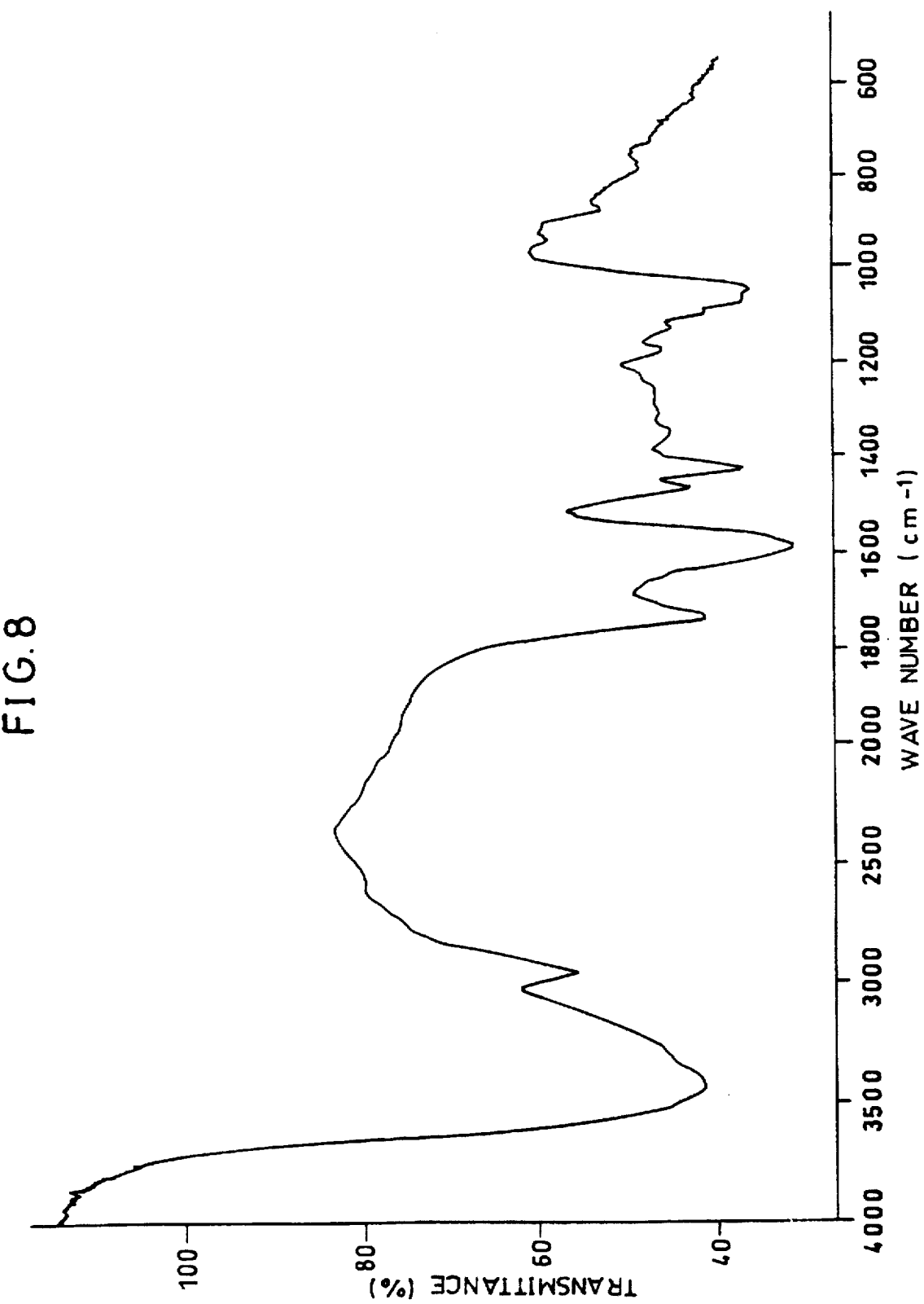
FIG. 8 is a view showing an infrared absorption spectrum of a copolymer produced in EXAMPLE 32.

The resulting copolymer is identified, in the same manner as EXAMPLE 28, as a new acrylic-ester-based polymer of the present invention. The number average molecular amount of the acrylic-ester-based polymer evaluated by the Gel Permeation Chromatography is 210,000. The infrared absorption spectrum of the above copolymer is set forth in FIG. 8.

EXAMPLE 33

Herein, 2.0 g of ethyl-α-(glucosidemethyl)acrylate produced in EXAMPLE 3, 1.0 g of sodium-α-(glucosidemethyl)acrylate, the acrylic ester derivative produced in EXAMPLE 22, 2.0 g of acrylic acid, 5.0 g of sodium acrylate, and 0.004 g of 2,2'-azobisisobutyronitrile are placed in a test tube and the test tube is sealed airtight after nitrogen substitution. Then, a copolymer is produced through a copolymerization in a similar manner to the polymerization of EXAMPLE 28.

Figure 9:
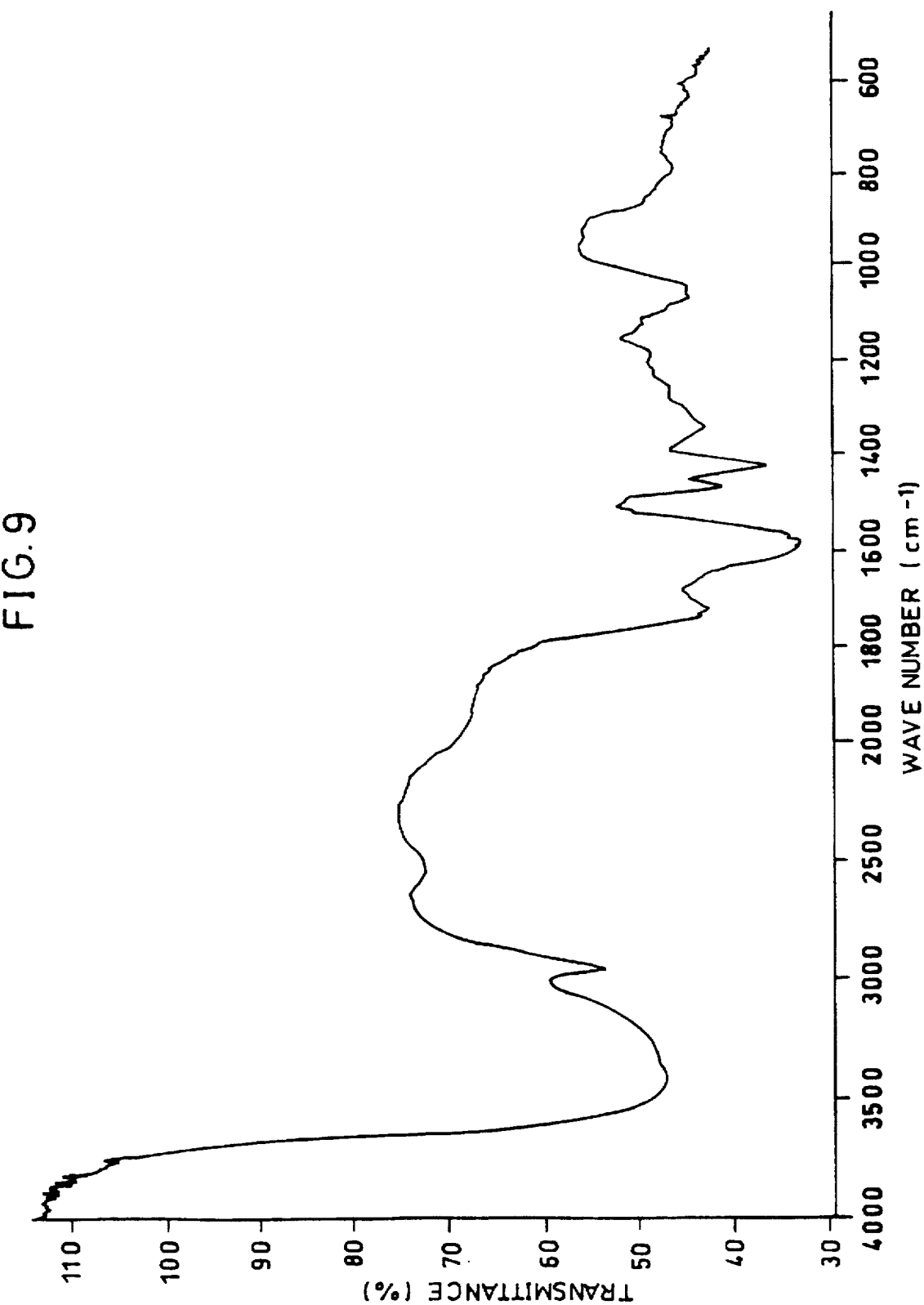
FIG. 9 is a view showing an infrared absorption spectrum of a copolymer produced in EXAMPLE 33.

The resulting copolymer is identified, in the same manner as EXAMPLE 28, as a new acrylic-ester-based polymer of the present invention. The number average molecular amount of the acrylic-ester-based polymer evaluated by the Gel Permeation Chromatography is 240,000. The infrared absorption spectrum of the above copolymer is set forth in FIG. 9.

EXAMPLE 34

Herein, 1.5 g of methyl-α-(glucosidemethyl)acrylate, the acrylic ester derivative produced in EXAMPLE 17, 1.5 g of acrylic acid, 4.0 g of sodium acrylate, and 0.004 g of benzoyl peroxide are placed in a test tube and the test tube is sealed airtight after nitrogen substitution. Then, a copolymer is produced through a copolymerization in a similar manner to the polymerization of EXAMPLE 28.

Figure 10:
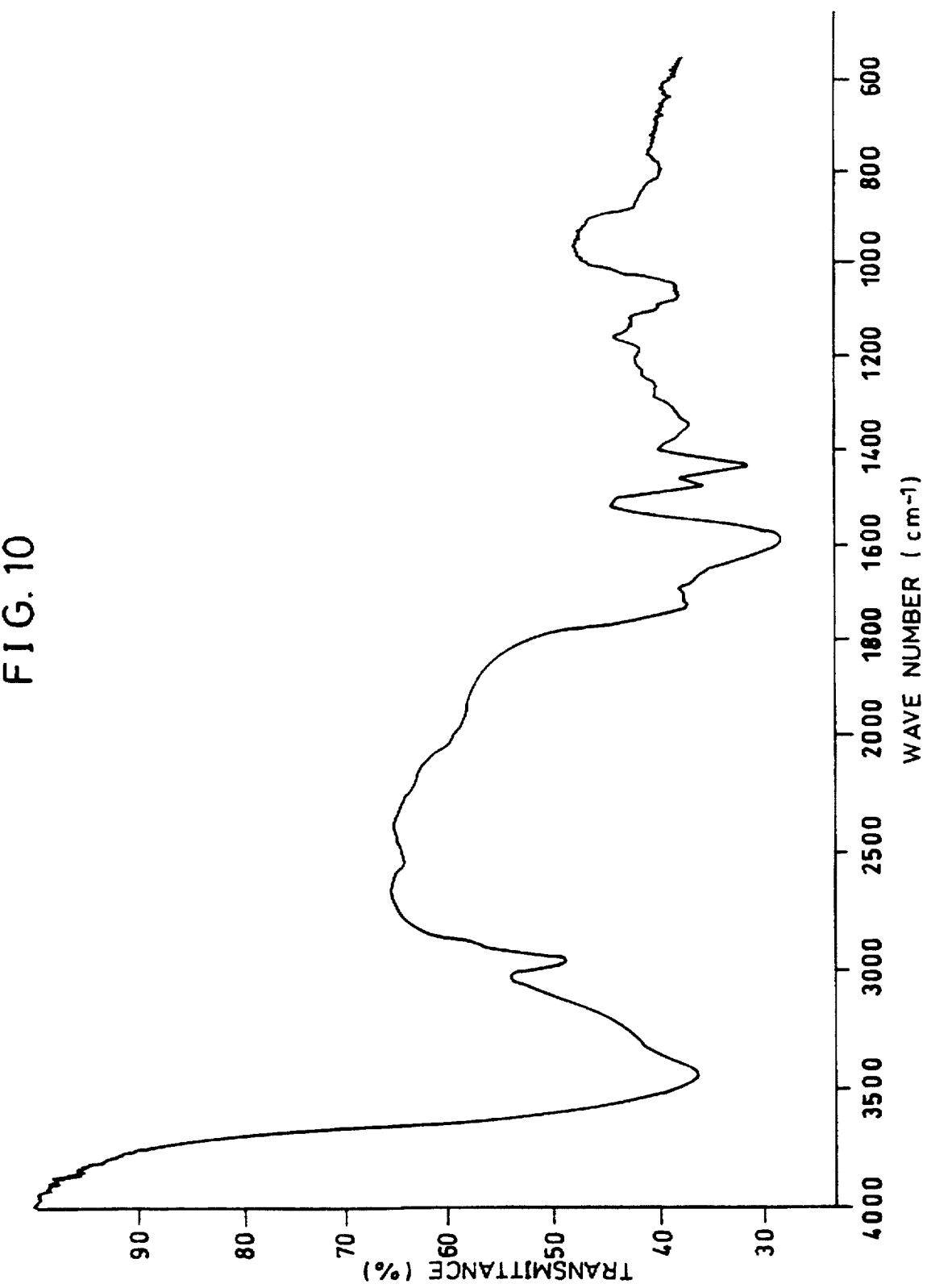
FIG. 10 is a view showing an infrared absorption spectrum of a copolymer produced in EXAMPLE 34.

The resulting copolymer is identified, in the same manner as EXAMPLE 28, as a new acrylic-ester-based polymer of the present invention. The number average molecular amount of the acrylic-ester-based polymer evaluated by the Gel Permeation Chromatography is 290,000. The infrared absorption spectrum of the above copolymer is set forth in FIG. 10.

EXAMPLE 35

Herein, 1.0 g of α-(glucosidemethyl)acrylate, the acrylic ester derivative produced in EXAMPLE 21, 1.0 g of ethylacrylate serving as a monomer, 1.0 g of acrylic acid, 3.5 g of sodium acrylate, and 0.007 g of 2,2'-azobisisobutyronitrile are placed in a test tube and the test tube is sealed airtight after nitrogen substitution. Then, a copolymer is produced through a copolymerization in a similar manner to the polymerization of EXAMPLE 28.

Figure 11:
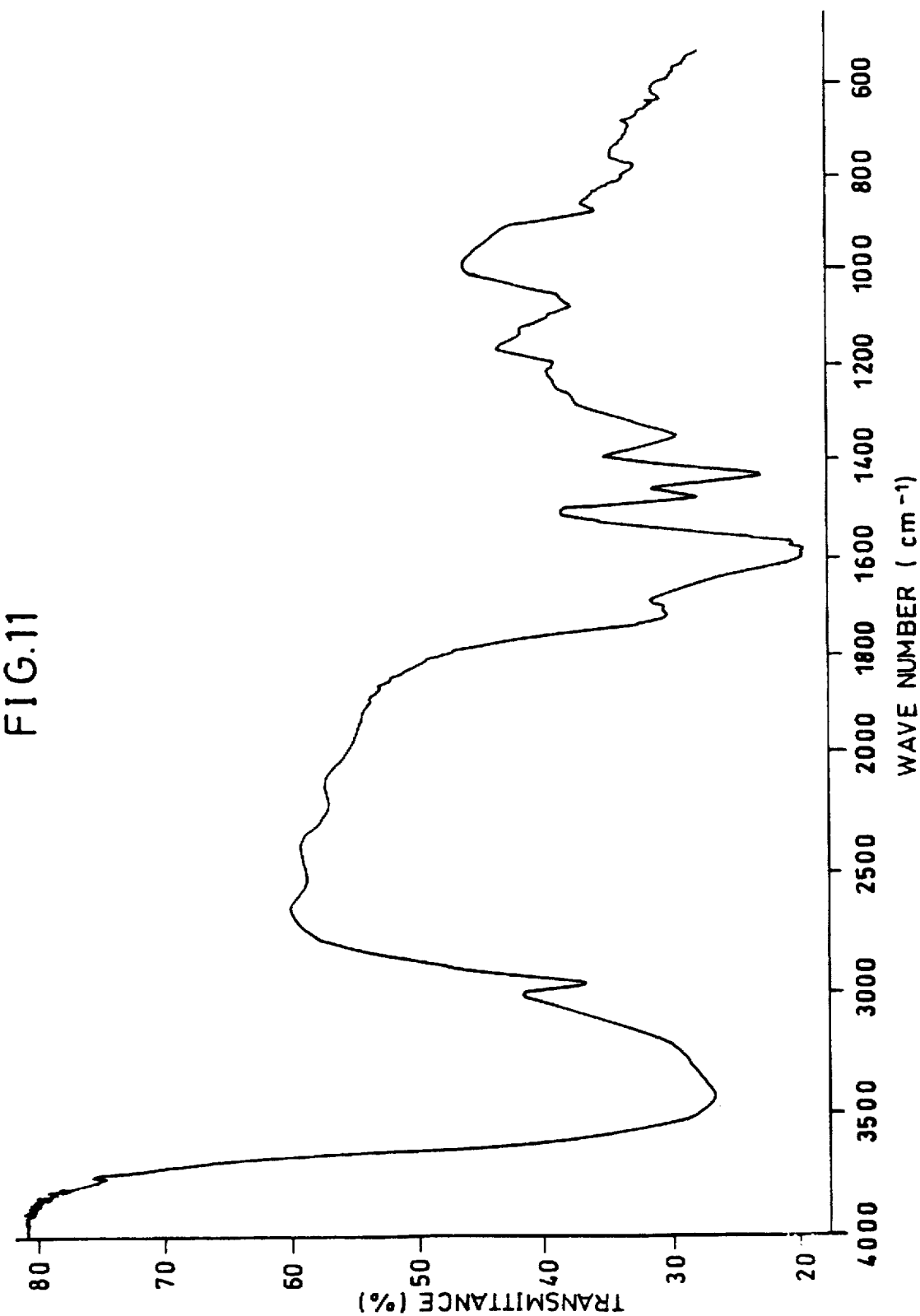
FIG. 11 is a view showing an infrared absorption spectrum of a copolymer produced in EXAMPLE 35.

The resulting copolymer is identified, in the same manner as EXAMPLE 28, as a new acrylic-ester-based polymer of the present invention. The number average molecular amount of the acrylic-ester-based polymer evaluated by the Gel Permeation Chromatography is 253,000. The infrared absorption spectrum of the above copolymer is set forth in FIG. 11.

EXAMPLE 36

Herein, 0.8 g of sodium-α-(glucosidemethyl)acrylate produced in EXAMPLE 22, 1.3 g of ethylacrylate, 6.2 g of sodium acrylate, and 0.0 g of 2,2'-azobisisobutyronitrile are placed in a test tube and the test tube is sealed airtight after nitrogen substitution. Then, a copolymer is produced through a copolymerization in a similar manner to the polymerization of EXAMPLE 28.

Figure 12:
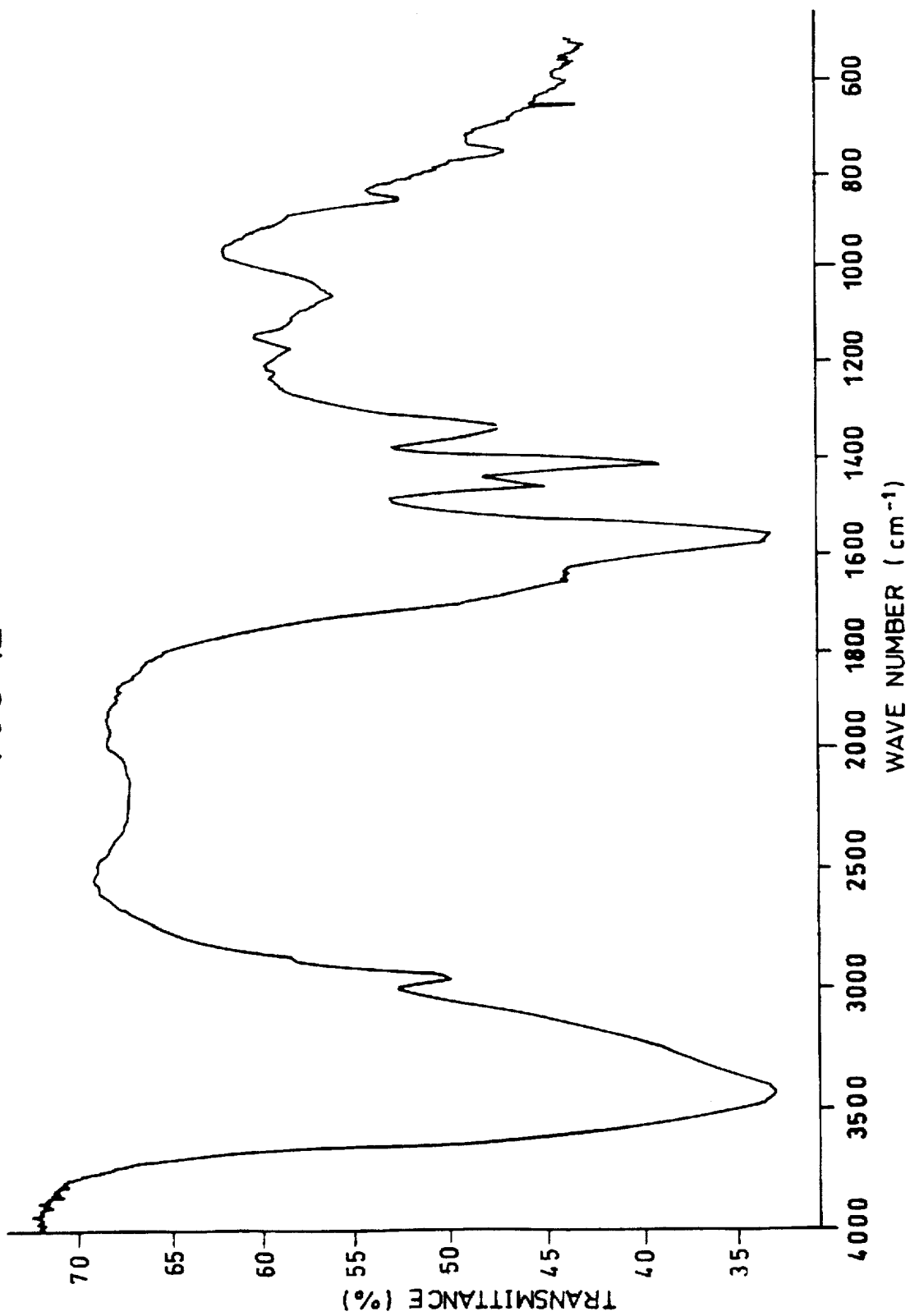
FIG. 12 is a view showing an infrared absorption spectrum of a copolymer produced in EXAMPLE 36.

The resulting copolymer is identified, in the same manner as EXAMPLE 28, as a new acrylic-ester-based polymer of the present invention. The number average molecular amount of the acrylic-ester-based polymer evaluated by the Gel Permeation Chromatography is 197,000. The infrared absorption spectrum of the above copolymer is set forth in FIG. 12.

EXAMPLE 37

Herein, 5.8 g of ethyl-α-(glucosidemethyl)acrylate produced in EXAMPLE 1 and 0.002 g of benzoyl peroxide are placed in a test tube and the test tube is sealed airtight after nitrogen substitution. Then, a polymer is produced in the same manner as EXAMPLE 28.

Figure 13:
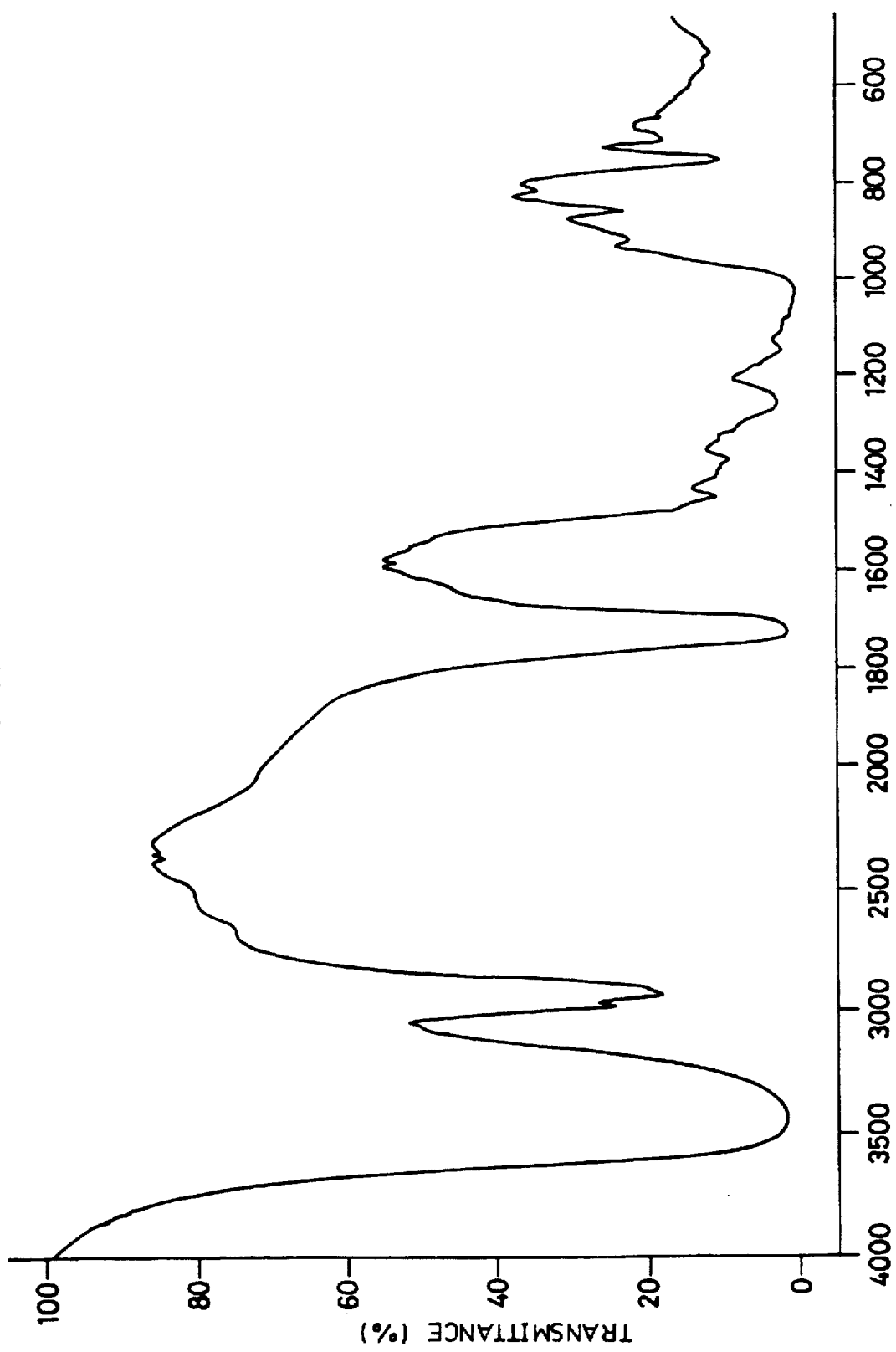
FIG. 13 is a view showing an infrared absorption spectrum of a copolymer produced in EXAMPLE 37.

The resulting polymer is identified, in the same manner as EXAMPLE 28, as a new acrylic-ester-based polymer of the present invention. The number average molecular amount of the acrylic-ester-based polymer evaluated by the Gel Permeation Chromatography is 42,000. The infrared absorption spectrum of the above polymer is set forth in FIG. 13.

EXAMPLE 38

Herein, 5.8 g of ethyl-α-(glucosidemethyl)acryalte produced in EXAMPLE 2, 2.0 g of methylmethacrylate, and 0.004 g of 2,2'-azobisisobutyronitrile are placed in a test tube and the test tube is sealed airtight after nitrogen substitution. Then, a copolymer is produced through a copolymerization in a similar manner to the polymerization of EXAMPLE 28.

Figure 14:
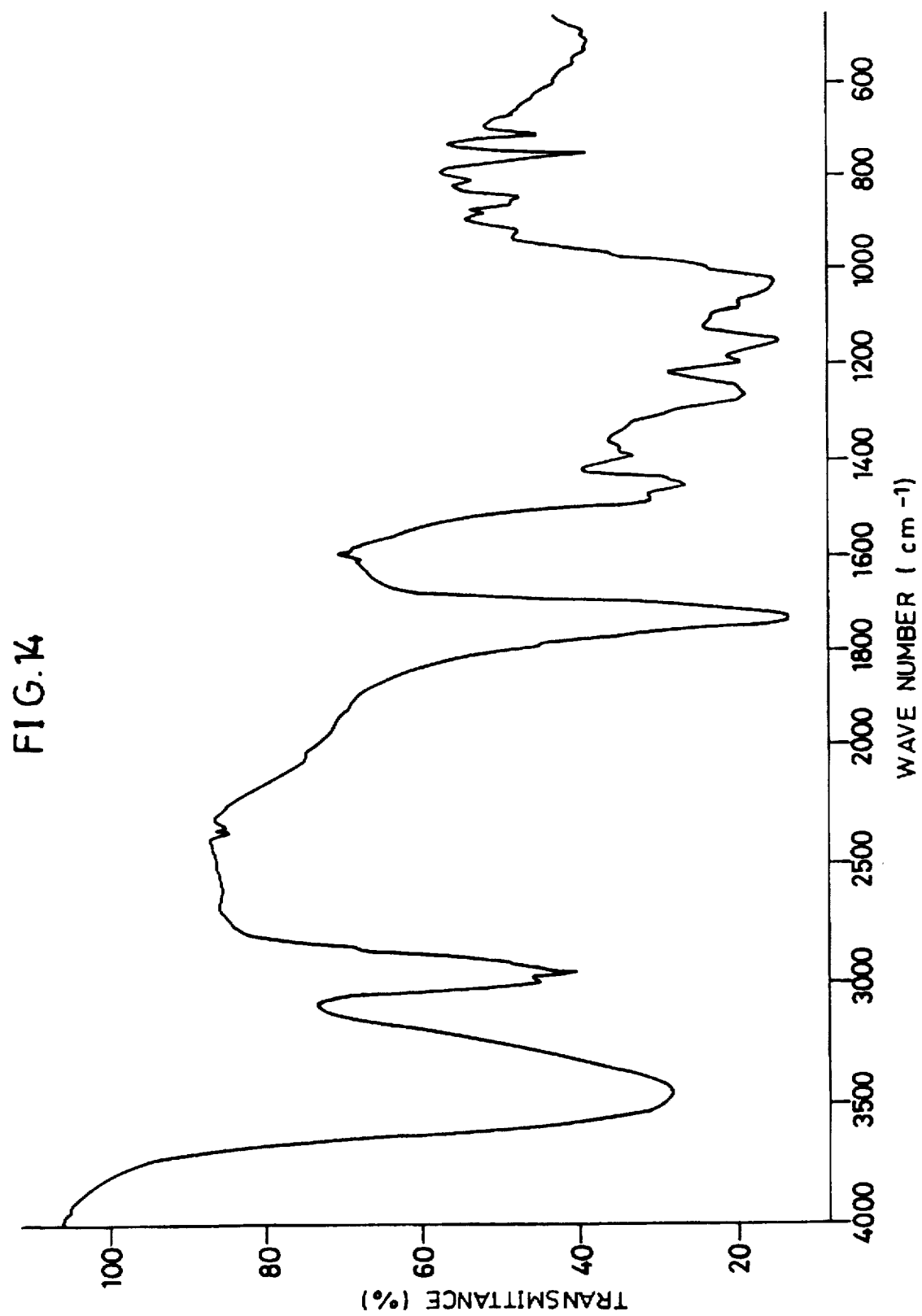
FIG. 14 is a view showing an infrared absorption spectrum of a copolymer produced in EXAMPLE 38.

The resulting copolymer is identified, in the same manner as EXAMPLE 28, as a new acrylic-ester-based polymer of the present invention. The number average molecular amount of the acrylic-ester-based polymer evaluated by the Gel Permeation Chromatography is 56,000. The infrared absorption spectrum of the above copolymer is set forth in FIG. 14.

EXAMPLE 39

Herein, 5.8 g of ethyl-α-(glucosidemethyl)acryalte produced in EXAMPLE 3, 2.1 g of styrene, 0.004 g of 2,2'-azobisisobutyronitrile are placed in a test tube and the test tube is sealed airtight after nitrogen substitution. Then, a copolymer is produced through a copolymerization in a similar manner to the polymerization of EXAMPLE 28.

Figure 15:
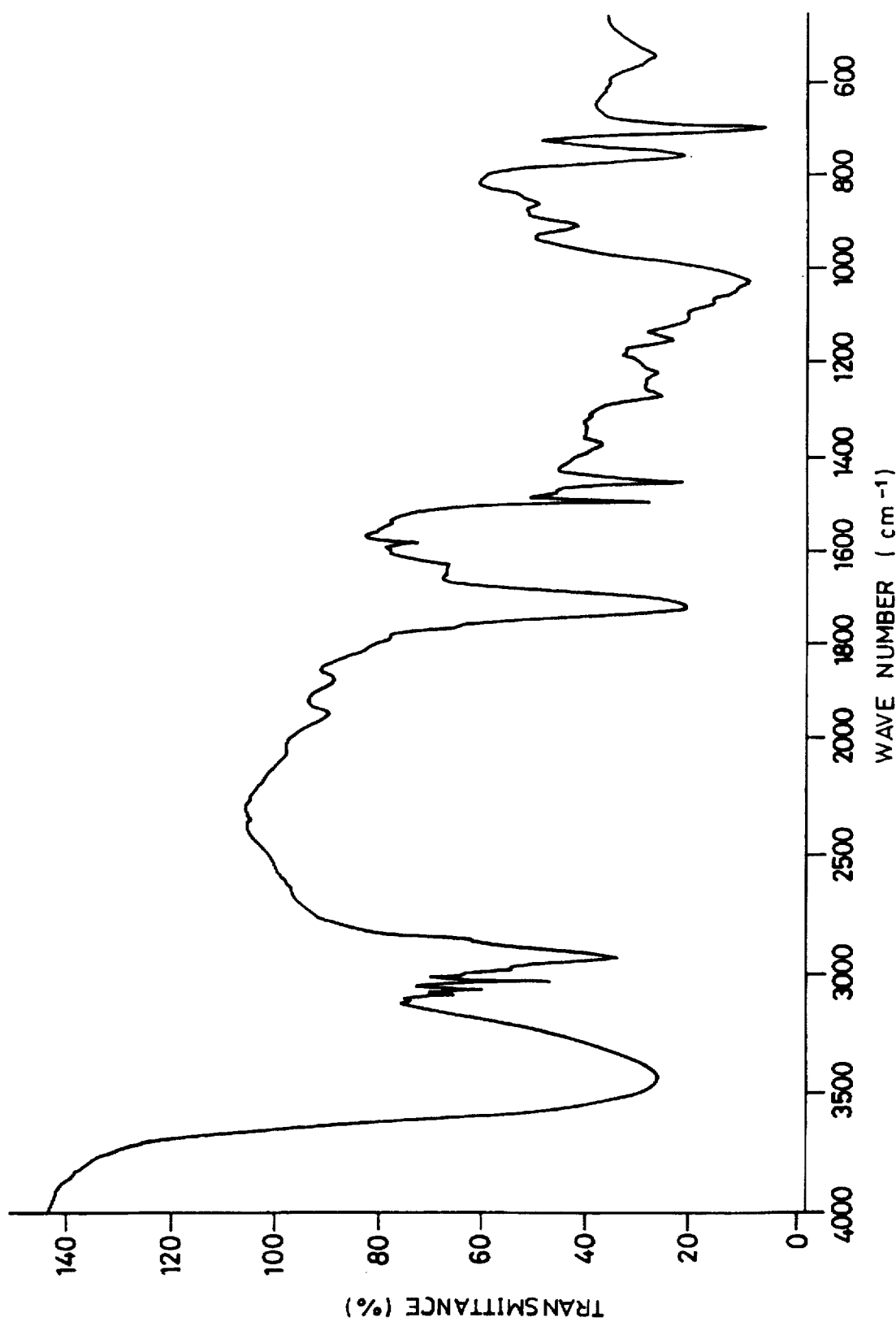
FIG. 15 is a view showing an infrared absorption spectrum of a copolymer produced in EXAMPLE 39.

The resulting copolymer is identified, in the same manner as EXAMPLE 28, as a new acrylic-ester-based polymer of the present invention. The number average molecular amount of the acrylic-ester-based polymer evaluated by the Gel Permeation Chromatography is 58,000. The infrared absorption spectrum of the above copolymer is set forth in FIG. 15.

EXAMPLE 40

Herein, 130 g of ethyl-α-hydroxymethylacrylate, 0.065 g of hydroquinone monomethyl ether serving as a polymerization inhibitor (first-order oxidation inhibitor), and 0.030 g of 2,2'-oxamidobis [ethyl-3-(3, 5-di-t-butyl-4-hydroxyphenyl)propionate] serving as a polymerization inhibitor (chleating agent) are stirred in a reactor of the same type used in EXAMPLE 1. Then, 36 g of glucose and 1.9 g of paratoluenesulfonic acid monohydrate are added, and the reactant solution is heated slowly with stirring. Further, the reactant solution is subject to stirring for one and a half hour at 100° C. under a normal pressure.

When the reaction ends, the reactant solution is cooled to 60° C. and neutralized with a sodium carbonate anhydride. The resulting neutralized solution is filtered and 60 g of water is added. Then, 120 g of ethyl acetate serving as an organic solvent is added slowly to the filtrate with stirring. The resulting mixed solution is stirred for half an hour at room temperature and let stand to separate the same into two layers: a water layer and an ethyl acetate layer. Then, the water layer alone is placed and 120 g of ethyl acetate is added, and the reactant is let stand after having been stirred for half an hour at room temperature. The above extraction process (purification process) is performed repetitively, and a purified ethyl-α-(glucosidemethyl)acrylate water solution is produced as a result.

The purity of ethyl-α-(glucosidemethyl)acryalte in the resulting water solution is evaluated using HPLC under predetermined conditions. Then, the purity of ethyl-α-(glucosidemethyl)acrylate is 99 percent by weight. This means that the resulting solution contains the crosslinking impurities of 1 or less percent by weight.

Further, the above solution is vacuum concentrated by a predetermined method to produce 50 wt % ethyl-α-(glucosidemethyl)acrylate water solution. The yellow index of the resulting concentrated water solution evaluated in the above-described manner is 3.

EXAMPLE 41

A neutralized solution is produced by performing the reaction and process in the same manner as EXAMPLE 40. The resulting neutralized solution is filtered and 60 g of water is added. Then, 200 g of ethyl acetate is added slowly to the filtrate with stirring. The resulting mixed solution is stirred for half an hour at room temperature and let stand to separate the same into two layers: a water layer and an ethyl acetate layer. As a result, a purified ethyl-α-(glucosidemethyl)acrylate water solution is produced.

The purity of ethyl-α-(glucosidemethyl)acryalte in the resulting water solution is evaluated, in the same manner as EXAMPLE 40, as 97 percent by weight. This means that the resulting solution contains the crosslinking impurities of 3 or less percent by weight. Further, the above solution is vacuum concentrated in the same manner as EXAMPLE 40 and the yellow index of the resulting concentrated water solution is evaluated as 7.

EXAMPLE 42

Herein, 130 g of ethyl-α-hydroxymethylacrylate, 0.013 g of hydroquinone serving as a polymerization inhibitor (first-order oxidation inhibitor), and 0.005 g of dilauryl-3,3'-thiodipropionate serving as a polymerization inhibitor (second-order oxidation inhibitor) are stirred in a reactor of the same type used in EXAMPLE 1. Then, 27 g of glucose and 0.4 g of hydrochloric acid are added, and the reactant solution is heated slowly with stirring. Further, the reactant solution is subject to stirring for 45 minutes at 120° C. under a normal pressure.

When the reaction ends, the reactant solution is cooled to 50° C. and neutralized with a 2N-sodium hydroxide water solution. Further, 80 g of n-butanol serving as an organic solvent is added to the resulting neutralized solution. Then, 80 g of water is added slowly to the resulting neutralized solution with stirring. The resulting mixed solution is stirred for 50 minutes at room temperature and let stand to separate the same into two layers: a water layer and an n-butanol layer. Then, the water layer alone is placed and 80 g of n-butanol is added and the reactant is let stand after having been stirred for 50 minutes at room temperature. The above extraction process (purification process) is performed repetitively and a purified ethyl-α-(glucosidemethyl)acrylate water solution is produced as a result.

The purity of ethyl-α-(glucosidemethyl)acrylate in the resulting water solution is evaluated, in the same manner as EXAMPLE 40, as 97 percent by weight. This means that the resulting solution contains the crosslinking impurities of 3 or less percent by weight. Further, the above solution is vacuum concentrated in the same manner as EXAMPLE 40, and the yellow index of the resulting concentrated water solution is evaluated as 5.

EXAMPLE 43

Herein, 130 g of ethyl-α-hydroxymethylacrylate, 0.10 g of p-benzoquinone serving as a polymerization inhibitor (first-order oxidation inhibitor), and 0.03 g of distearyl-3, 3'-thiodipropionate are stirred in a reactor of the same type used in EXAMPLE 1. Then, 18 g of glucose and 0.5 g of hydrochloric acid are added, and the reactant solution is heated slowly with stirring. Further, the reactant solution is subject to stirring for an hour at 80° C. under a normal pressure.

When the reaction ends, the reactant solution is cooled to 30° C. and neutralized with a 2N-potassium hydroxide water solution. Then, 90 g of water and 100 g of toluene serving as an organic solvent are added together to the resulting neutralized solution. The resulting mixed solution is stirred for 40 minutes at room temperature and let stand to separate the same into two layers: a water layer and a toluene layer.

Then, the water layer alone is placed and 100 g of toluene is added, and the reactant is let stand after having been stirred for 40 minutes at room temperature. The above extraction process (purification process) is performed repetitively, and a purified ethyl-α-(glucosidemethyl) acrylate water solution is produced as a result.

The purity of ethyl-α-(glucosidemethyl)acryalte in the resulting water solution is evaluated, in the same manner as EXAMPLE 40, as 98 percent by weight. This means that the resulting solution contains the crosslinking impurities of 2 or less percent by weight. Further, the above solution is vacuum concentrated in the same manner as EXAMPLE 40, and the yellow index of the resulting concentrated water solution is evaluated as 5.

EXAMPLE 44

A neutralized solution is produced by performing a reaction and a process in the same manner as EXAMPLE 43, and 90 g of water and 180 g of toluene are added together to the resulting neutralized solution. The resulting mixed solution is stirred for 40 minutes at room temperature and let stand to separate the same into two layers: a water layer and a toluene layer. As a result, a purified ethyl-α-(glucosidemethyl)acrylate water solution is produced.

The purity of ethyl-α-(glucosidemethyl)acryalte in the resulting water solution is evaluated, in the same manner as EXAMPLE 40, as 95 percent by weight. This means that the resulting solution contains the crosslinking impurities of 5 or less percent by weight. Further, the above solution is vacuum concentrated in the same manner as EXAMPLE 40, and the yellow index of the resulting concentrated water solution is evaluated as 12.

EXAMPLE 45

Herein, 130 g of ethyl-α-hydroxymethylacryalte, 0.02 g of chloranil serving as a polymerization inhibitor (first-order oxidation inhibitor), and 0.02 g of ethylenediaminetetraacetic acid serving as a polymerization inhibitor (chleating agent) are stirred in a reactor of the same type used in EXAMPLE 1. Then, 45 g of glucose and 1.9 g of paratoluenesulfonic acid monohydrate are added, and the reactant solution is heated slowly with stirring. Further, the reactant solution is subject to stirring for two hours at 70° C. under a normal pressure.

When the reaction ends, the reactant solution is cooled to 40° C. and neutralized with a potassium carbonate anhydride. The resulting neutralized solution is filtered and 250 g of 2-butanone is added. Then, 90 g of water is added slowly to the resulting solution with stirring. The resulting mixed solution is stirred for 45 minutes at room temperature and let stand to separate the same into two layers: a water layer and a 2-butanone layer. As a result, a purified ethyl-α-(glucosidemethyl)acrylate water solution is produced.

The purity of ethyl-α-(glucosidemethyl)acryalte in the resulting water solution is evaluated, in the same manner as EXAMPLE 40, as 95 percent by weight. This means that the resulting solution contains the crosslinking impurities of 5 or less percent by weight. Further, the above solution is vacuum concentrated in the same manner as EXAMPLE 40, and the yellow index of the resulting concentrated water solution is evaluated as 13.

EXAMPLE 46

Herein, 130 g of ethyl-α-hydroxymethylacryalte and 0.13 g of 2,5-di-t-butylhydroquinone serving as a polymerization inhibitor (first-order oxidation inhibitor) are stirred in a reactor of the same type used in EXAMPLE 1. Then, 36 g of glucose and 1.0 g of tungstophosphoric acid are added, and the reactant solution is heated slowly with stirring. Further, the reactant solution is subject to stirring for one and a half hour at 75° C. under a normal pressure.

When the reaction ends, the reactant solution is cooled to 35° C. and neutralized with a 2N-sodium hydroxide water solution. On the other hand, a mixed solution is prepared by mixing 100 g of water and 160 g of cyclohexane serving as an organic solvent. The resulting neutralized solution is added slowly to the mixed solution with stirring. The resulting mixed solution is stirred for 50 minutes at room temperature and let stand to separate the same into two layers: a water layer and a cyclohexane layer. The water layer alone is placed and 160 g of cyclohexane is added and the reactant is let stand after having been stirred for 50 minutes at room temperature. The above extraction process (purification process) is performed repetitively, and a purified ethyl-α-(glucosidemethyl)acryalte water solution is produced as a result.

The purity of ethyl-α-(glucosidemethyl)acryalte in the resulting water solution is evaluated, in the same manner as EXAMPLE 40, as 98 percent by weight. This means that the resulting solution contains the crosslinking impurities of 2 or less percent by weight. Further, the above solution is vacuum concentrated in the same manner as EXAMPLE 40, and the yellow index of the resulting concentrated water solution is evaluated as 4.

EXAMPLE 47

Herein, 130 g of ethyl-α-hydroxymethylacrylate and 0.10 g of hydroquinone monomethyl ether are stirred in a reactor of the same type used in EXAMPLE 1. Then, 36 g of glucose, 2.0 g of paratoluenesulfonic acid monohydrate, and 100 g of toluene serving as a solvent are added, and the reactant solution is heated slowly with stirring. Further, the reactant solution is subject to stirring for two hours at 95° C. under a normal pressure.

When the reaction ends, the reactant solution is cooled to 35° C. and neutralized with a 2N-sodium hydroxide water solution. Then, 100 g of water is added slowly to the resulting neutralized solution with stirring. The resulting mixed solution is stirred for 45 minutes at room temperature and let stand to separate the same into two layers: a water layer and a toluene layer. The water layer alone is placed and 130 g of toluene is added, and the reactant is let stand after having been stirred for 45 minutes at room temperature. The above extraction process (purification process) is performed repetitively, and a purified ethyl-α-(glucosidemethyl) acrylate water solution is produced as a result.

The purity of ethyl-α-(glucosidemethyl)acryalte in the resulting water solution is evaluated, in the same manner as EXAMPLE 40, as 98 percent by weight. This means that the resulting solution contains the crosslinking impurities of 2 or less percent by weight. Further, the above solution is vacuum concentrated in the same manner as EXAMPLE 40, and the yellow index of the resulting concentrated water solution is evaluated as 5.

EXAMPLE 48

Herein, 25 g of an ethyl-α-(glucosidemethyl)acrylate solution, the acrylic ester derivative produced in EXAMPLE 40, and 0.01 g of benzoil peroxide are placed in a test tube. Then, the content is subject to stirring for five hours at 60° C. under nitrogen gaseous atmosphere, letting ethyl-α-

(glucosidemethyl)acrylate undergo a polymerization. As a result, a polymer of ethyl-α-(glucosidemethyl)acrylate is generated and no gelation is acknowledged during the polymerization.

The resulting polymer is identified by evaluating $^1$H-NMR, $^{13}$C-NMR, and the absorption wave number of the infrared absorption spectrum of the same. Then, the polymer is identified as a new acrylic-ester-based polymer of the present invention. The number average molecular amount (Mn) of the acrylic-ester-based polymer evaluated by the Gel Permeation Chromatography (GPC) is 51,000.

EXAMPLE 49

Herein, 25 g of an ethyl-α-(glucosidemethyl)acrylate solution produced in EXAMPLE 41 and 0.01 g of benzoil peroxide are placed in a test tube. Then, a polymer is produced through polymerization in the same manner as EXAMPLE 48. No gelation is acknowledged during the polymerization.

Figure 16:
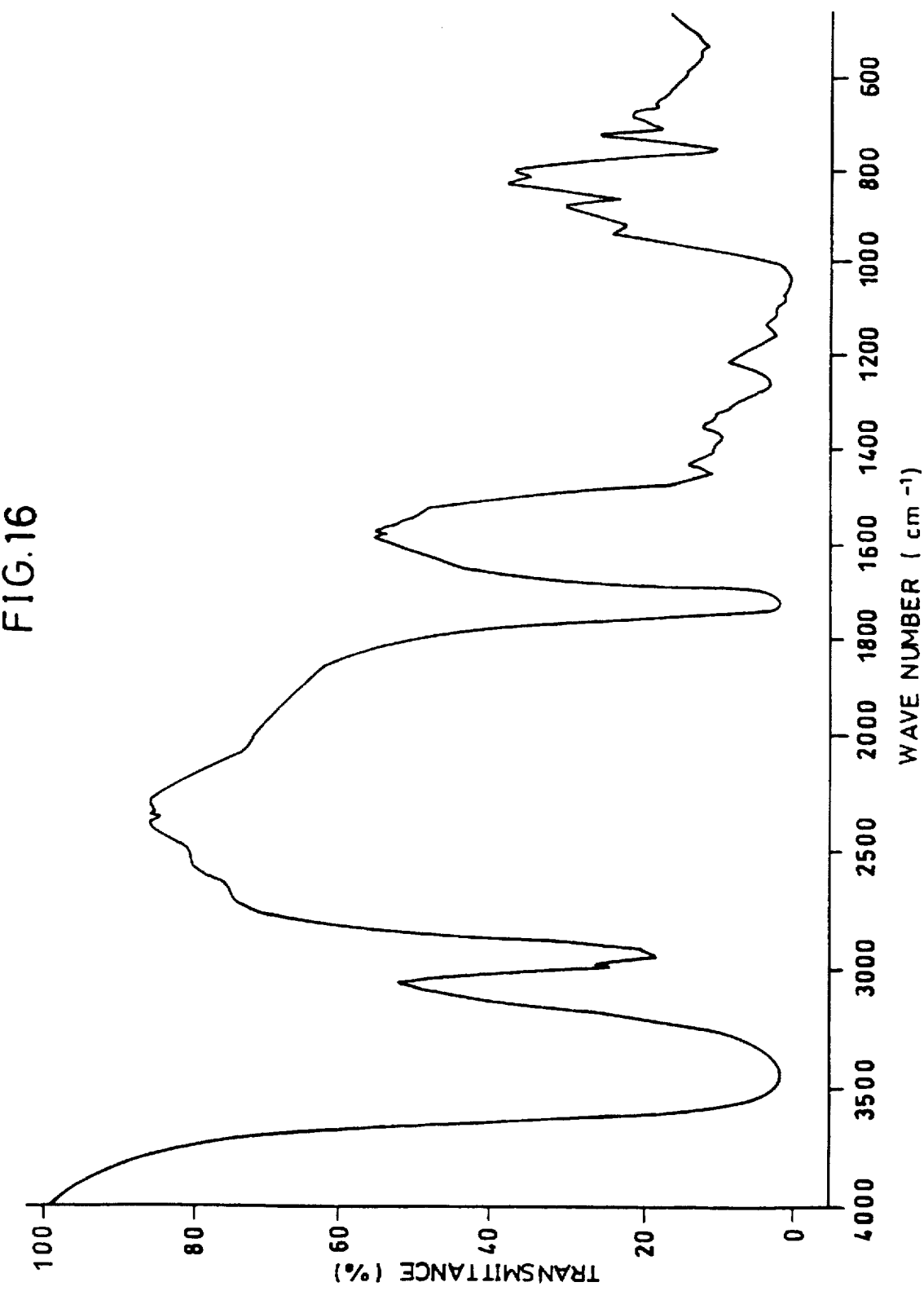
FIG. 16 is a view showing an infrared absorption spectrum of a polymer produced in EXAMPLE 49.

The resulting polymer is identified, in the same manner as EXAMPLE 48, as a new acrylic-ester-based polymer of the present invention. The number average molecular amount of the acrylic-ester-based polymer evaluated by the Gel Permeation Chromatography is 51,000. The yellow index of the resulting polymer is evaluated as 14 in the same manner as above. The infrared absorption spectrum of the above polymer is set forth in FIG. 16.

EXAMPLE 50

A polymers is produced in the same manner as EXAMPLE 48 using solutions of the acrylic ester derivative produced in EXAMPLES 42 through 47. No gelation is acknowledged during the polymerization.

The resulting polymer is identified, in the same manner as EXAMPLE 48, as a new acrylic-ester-based polymer of the present invention.

COMPARATIVE EXAMPLE 3

A neutralized solution is produced by performing a reaction and a process in the same manner as EXAMPLE 40, and the resulting neutralized solution is filtered. The resulting filtrate is subject to vacuum evaporation under the condition: 73° C./5 mmHg–76° C./5 mmHg. As a result, the raw material, ethyl-α-hydroxymethylacryate is removed and ethyl-α-(glucosidemethyl)acrylate is produced.

The purity of ethyl-α-(glucosidemethyl)acrylate thus produced is evaluated, in the same manner as EXAMPLE 40, as 86 percent by weight. This means that the resulting solution contains the crosslinking impurities of 14 or less percent by weight. The main structure of the crosslinking impurities are analyzed and the amount thereof is evaluated under predetermined conditions using HPLC. Then, it is acknowledged that the resulting solution contains 3 percent by weight of crosslinking impurities expressed by a chemical formula:

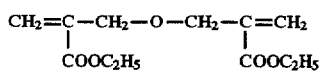

5 percent by weight of crosslinking impurities expressed by a chemical formula:

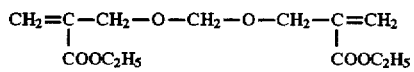

4 percent by weight of crosslinking impurities expressed by a chemical formula:

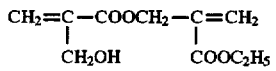

COMPARATIVE EXAMPLE 4

Herein, 86 wt % ethyl-α-(glucosidemethyl)acrylate produced in COMPARATIVE EXAMPLE 3 is let undergo a polymerization in the same manner as EXAMPLE 48. Then, the resulting product turns into gel and no polymer is produced.

COMPARATIVE EXAMPLE 5

A neutralized solution is produced by performing a reaction and a process in the same manner as EXAMPLE 41, and the resulting neutralized solution is filtered. Then, the resulting filtrate is subject to vacuum evaporation under the condition: 73° C./5 mmHg–75° C./5 mmHg. As a result, the raw material, ethyl-α-hydroxymethylacrylate is removed and ethyl-α-(glucosidemethyl ) acrylate is produced.

The yield and purity of ethyl-α-(glucosidemethyl)acrylate are evaluated in the same manner as EXAMPLE 40. Then, the yield is 70 percent by mole and the purity is 86 percent by weight. This means that the resulting solution contains the crosslinking impurities of 14 or less percent by weight. Further, the above solution is diluted with pure water to produce a 50 wt % ethyl-α-(glucosidemethyl)acrylate water solution, and the yellow index of the resulting solution is evaluated as 52.

EXAMPLE 51

Herein, 13 0 g of ethyl-α-hydroxymethylacrylate and 0.03 g of tetrakis[methylene-3-(3',5'-di-t-butyl-4'-hydroxyphenyl)propionate]methane are stirred in a reactor of the same type used in EXAMPLE 1. Then, 36 g of glucose and 1.9 g of paratoluenesufonic acid monohydrate are added, and the reactant solution is heated slowly with stirring. Further, the reactant solution is subject to heating for one and a half hour at 100° C. under normal pressure.

When the reaction ends, the reactant solution is cooled to 60° C. and neutralized with a sodium carbonate anhydride. The resulting neutralized solution is filtered and 60 g of water is added. Then, 120 g of ethyl acetate is added slowly to the resulting filtrate with stirring. The resulting mixed solution is let stand after it has been stirred for half an hour at room temperature to separate the same into two layers: a water layer and an ethyl acetate layer. Then, the water layer alone is placed and 120 g of ethyl acetate is added, and the reactant is let stand after it has been stirred for half an hour at room temperature. The above extraction process (purification process) is performed repetitively, and a purified ethyl-α-(glucosidemethyl)acrylate water solution is produced as a result.

The purity of ethyl-α-(glucosidemethyl)acrylate in the resulting water solution is evaluated, in the same manner as EXAMPLE 40, as 99 percent by weight. Note that the above water solution includes no tetrakis [methylene-3-(3',5'-di-t-butyl-4'-hydroxyphenyl )propionate]methane.

The above water solution is vacuum concentrated by a predetermined method, and ethyl-α-(glucosidemethyl) acrylate is separated by removing water. On the other hand, a mixed gas is prepared by mixing an oxygen gas and a nitrogen gas in a capacity ratio of 7:93.

Then, 20 g of ethyl-α-(glucosidemethyl)acrylate, 4.0 mg of hydroquinone monomethyl ether serving as a polymerization inhibitor (first-order oxidation inhibitor) are placed in a test tube and the test tube is sealed airtight after the gaseous phase thereof is substituted with the above mixed gas. The density of molecular oxygens in the gaseous phase in the test tube is 7 percent by capacity. Then, the test tube is placed in an oil bath of 50° C. and shaken for 24 hours.

Then, the content is taken out from the test tube, and analyzed using HPLC and an HLC 8120 model of Gel Permeation Chromatography (herein after referred to as GPC) of Tosoh Corporation under predetermined conditions. Then, neither impurities nor production of a polymer is acknowledged. In addition, no coloring is acknowledged. That is to say, the quality of ethyl-α-(glucosidemethyl) acrylate is maintained.

EXAMPLE 52

A reaction, a process, and an analysis are performed in the same manner as EXAMPLE 51 except that 20 g of 50 wt % ethyl-α-(glucosidemethyl)acrylate water solution is used instead of 20 g of ethyl-α-(glucosidemethyl)acrylate and 2.0 mg of hydroquinone is used as a polymerization inhibitor (first-order oxidation inhibitor) instead of 4.0 mg of hydroquinone monomethyl ether. Then, neither impurities nor production of a polymer is acknowledged. In addition, no coloring is acknowledged. That is to say, the quality of ethyl-α-(glucosidemethyl)acrylate is maintained.

EXAMPLE 53

A reaction, a process, and an analysis are performed in the same manner as EXAMPLE 51 except that 1.0 mg of tetrakis[methylene-3-(3',5'-di-t-butyl-4'-hydroxyphenyl) propionate]methane serving as a polymerization inhibitor (first-order oxidation inhibitor) and 1.0 mg of 2,2'-oxamidobis [ethyl-3-(3,5-di-t-butyl-4-hydroxyphenyl) propionate serving as a polymerization inhibitor (chleating agent) are used instead of 4.0 mg of hydroquinone monoethyl ether. Then, neither impurities nor production of a polymer is acknowledged. In addition, no coloring is acknowledged. That is to say, the quality of ethyl-α-(glucosidemethyl)acrylate is maintained.

EXAMPLE 54

A reaction, a process, and an analysis are performed in the same manner as EXAMPLE 51 except that 20 g of 50 wt % ethyl-α-(glucosidemethyl)acrylate water solution is used instead of 20 g of ethyl-α-(glucosidemethyl)acrylate, and 1.0 mg of p-t-buthylcatecohl serving as a polymerization inhibitor (first-order oxidation inhibitor) and 1.0 mg of ethylenediaminetetraacetic acid serving as a polymerization inhibitor (chleating agent) are used instead of 4.0 mg of hydroquinone monomethyl ether. Then, neither impurities nor production of a polymer is acknowledged. In addition, no coloring is acknowledged. That is to say, the quality of ethyl-α-(glucosidemethyl)acrylate is maintained.

EXAMPLE 55

A reaction, a process, and an analysis are performed in the same manner as EXAMPLE 51 except that 1.0 mg of hydroquinone monomethyl ether and 1.0 mg of dilauryl-3,3'-thiodipropionate serving as a polymerization inhibitor (second-order oxidation inhibitor) are used instead of 4.0 mg of hydroquinone monomethyl ether. Then, neither impurities nor production of a polymer is acknowledged. In addition, no coloring is acknowledged. That is to say, the quality of ethyl-α-(glucosidemethyl)acrylate is maintained.

EXAMPLE 56

A reaction, a process, and an analysis are performed in the same manner as EXAMPLE 51 except that 20 g of 50 wt % ethyl-α-(glucosidemethyl)acrylate water solution is used instead of 20 g of ethyl-α-(glucosidemethyl)acrylate, and 1.0 mg of tetrakis[methylene-3-(3',5'-di-t-butyl-4'-hydroxyphenyl)propionate]methane and 1.0 mg of distearyl-3,3'-thiodipropionate serving as a polymerization inhibitor (second-order oxidation inhibitor) are used instead of 4.0 mg of hydroquinone monomethyl ether. Then, neither impurities nor production of a polymer is acknowledged. In addition, no coloring is acknowledged. That is to say, the quality of ethyl-α-(glucosidemethyl)acrylate is maintained.

COMPARATIVE EXAMPLE 6

A reaction and a process are performed in the same manner as EXAMPLE 51 except that no hydroquinone monomethyl ether serving as a polymerization inhibitor (first-order oxidation inhibitor) is used. Then, the content in the test tube starts to polymerize after the test tube has been placed in the oil bath of 50° C. and shaken for two hours. This indicates that if no polymerization inhibitor is used, the quality of ethyl-α-(glucosidemethyl)acrylate is not secured.

COMPARATIVE EXAMPLE 7

A reaction and a process are performed in the same manner as EXAMPLE 51 except that the gaseous phase in the test tube is substituted with a nitrogen gas instead of the mixed gas. The density of molecular oxygens in the gaseous phase is 0 percent by capacity. Then, the content in the test tube starts to polymerize after the test tube has been placed in the oil bath of 50° C. for two hours. This indicates that if the density of molecular oxygens is out of the above-specified range, the quality of ethyl-α-(glucosidemethyl) acrylate is not secured.

EXAMPLE 57

Herein, 146 parts by weight of distilled water serving as a solvent, 186 parts by weight of 50 wt % ethyl-α-(glucosidemethyl)acrylate water solution serving as an acrylic ester derivative (monomeric component), and 0.01 part by weight of polyethylene glycol diacrylate serving as a crosslinking agent are stirred in a reactor equipped with a thermometer and a stirring device to produce 332 parts by weight of monomeric component water solution. The density of the monomeric component in the resulting water solution is 28 percent by weight.

Then, 2.3 parts by weight of 10 wt % sodium persulfate water solution serving as a radical polymerization initiator and 2.3 parts by weight of 1 wt % L-ascorbic acid water solution serving as a reducing agent are added, and the reactant solution is let stand for a predetermined time at 30° C. under nitrogen atmosphere to undergo standing polymerization. As a result, a polymer of hydrous gel is produced.

The polymer of hydrous gel is taken out and heated for dryness for five hours at 50° C. under a vacuumed pressure of 30 mmHg using a vacuum drier. Then, the dried polymer of hydrous gel is ground using a vibrating mill. As a result, a crosslinked acrylic-ester-based polymer, namely, an water absorptive resin, is produced. The water absorption factor and biodegrability of the resulting water absorptive resin are evaluated in the following manner.

(a) WATER ABSORPTION FACTOR

To begin with, 0.2 g of water absorptive resin is put evenly into a tea-bagwise bag (40 mm×150 mm) made of non-woven fabric, and the bag is soaked in a 0.9 wt % sodium chloride solution (physiological salt solution) for an hour. Then, the bag is drained for a predetermined time and a weight $W_1$ (g) thereof is evaluated. The same is performed using a bag containing no water absorptive resin, and a weight $W_0$ (g) of the empty bag is also evaluated. Then, a water absorption factor (g/g) is calculated using a following equation:

$$\text{water absorption factor (g/g)} = \frac{(\text{weight } W_1 \text{ (g)} - \text{weight } W_0 \text{ (g)})}{\text{weight of water absorptive resin (g)}}$$

(b) BIODEGRABILITY

A test on biodegrability is performed in accordance with a revised MITI (Ministry of International Trade and Industry) test. More precisely, a testing material, namely, the water absorptive resin, is added to 300ml of basic culture solution, or a composite solution stipulated under an article of JIS K 0102 as to an amount of biochemical oxygen consumption, in such a way that the solution contains 100 ppm of water absorptive resin. In addition, standard sludge of Chemicals Inspection & Testing Institute, Japan, is added in such a way that the solution contains 30 ppm of the standard sludge. Then, the basic culture solution is cultivated for 28 days at 25° C. in a dark place with stirring. During the cultivation, an amount of oxygens consumed by the active sludge is evaluated periodically, and a BOD (Biochemical Oxygen Demand) curve is found. The biodegrability (%) is calculated using a following equation:

biodegrability (%)={(A-B)/C}×100 where A is a biochemical oxygen demand (mg) of the testing material (water absorptive resin) on the BOD curve, B is a blank on the BOD curve, that is to say, an amount of oxygen consumption (mg) of the basic culture solution, and C is a TOD (Total Oxygen Demand) (mg) demanded to completely oxidize the testing material.

The water absorption factor and biodegrability of the water absorptive resin thus found are 3.6 g/g and 30%, respectively. The result of evaluation is set forth in TABLE 4 below.

EXAMPLE 58

A water absorptive resin is produced by performing a reaction and a process in the same manner as EXAMPLE 57 except that 50 wt % sodium-α-(glucosidemethyl)acrylate water solution serving as an acrylic ester derivative (monomeric component) is used instead of 50 wt % ethyl-α-(glucosidemethyl)acrylate water solution. The water absorption factor and biodegrability of the resulting water absorptive resin are evaluated, in the same manner as EXAMPLE 57, as 31 g/g and 27%, respectively. The result of evaluation is set forth in TABLE 4 below.

EXAMPLE 59

Herein, 618 parts by weight of distilled water, 16 parts by weight of 50 wt % ethyl-α-(gluocsidemethyl)acrylate water solution serving as an acrylic ester derivative (monomeric component), 15 parts by weight of acrylic acid and 160 parts by weight of 37 wt % sodium acrylate water solution both serving as a monomer based on (meta)acrylic acid (monomeric component), and 0.03 part by weight of polyethylene glycol diacrylate are stirred in a reactor of the same type used in EXAMPLE 57. As a result, 809 parts by weight of monomeric component water solution is produced. The density of the monomeric component in the resulting water solution is 10 percent by weight.

Then, 1.7 part by weight of 10 wt % 2,2'-azobis(2-amidinopropane)dihydrochloride (V-50 of the Wako Pure Chemical Industries, Ltd.) water solution is added, and the resulting solution is let stand for a predetermined time at 30° C. under nitrogen atmosphere to undergo standing polymerization. As a result, a polymer of hydrous gel is produced.

The polymer of hydrous gel is taken out and heated to dryness for five hours at 50° C. under a vacuumed pressure of 30 mmHg using a vacuum drier. Then, the dried polymer of hydrous gel is ground using a vibrating mill. As a result, a crosslinked acrylic-ester-based polymer, namely, an water absorptive resin, is produced.

The water absorption factor and biodegrability of the resulting water absorptive resin are evaluated, in the same manner as EXAMPLE 57, as 41 g/g and 5%, respectively. The result of evaluation is set forth in TABLE 4 below.

EXAMPLE 60

A water absorptive resin is produced by performing a reaction and a process in the same manner as EXAMPLE 59 except that an amount of distilled water is reduced to 264 parts by weight from 618 parts by weight, and an amount of 50 wt % ethyl-α-(glucosidemethyl)acrylate water solution is increased to 37 parts by weight from 16 parts by weight. The water absorption factor and biodegrability of the resulting water absorptive resin are evaluated, in the same manner as EXAMPLE 57, as 50 g/g and 4%, respectively. The result of evaluation is set forth in TABLE 4 below.

EXAMPLE 61

A water absorptive resin is produced by performing a reaction and a process in the same manner as EXAMPLE 59 except that 50 wt % α-(glucosidemethyl)sodium acrylate solution is used instead of 50 wt % ethyl-α-(glucosidemethyl)acrylate solution in equal volume. The water absorption factor and biodegrability of the resulting water absorptive resin are evaluated, in the same manner as EXAMPLE 57, as 23 g/g and 7%, respectively. The result of evaluation is set forth in TABLE 4 below.

EXAMPLE 62

A water absorptive resin is produced in the same manner as EXAMPLE 59 except that an amount of distilled water is reduced to 264 parts by weight from 618 parts by weight, and 50 wt % α-(glucosidemethyl)sodium acrylate solution is used instead of 50 wt % ethyl-α-(glucosidemethyl)acrylate solution in equal volume. The water absorption factor and biodegrability of the water absorptive resin are evaluated, in the same manner as EXAMPLE 57, as 32 g/g and 5%, respectively. The result of evaluation is set forth in TABLE 4 below.

COMPARATIVE EXAMPLE 8

Herein, a 2-L type four-neck round bottom flask equipped with a thermometer, a reflux cooler, a dropping funnel, a nitrogen gas blowing pipe, and a stirring device is used as a reactor. Accordingly, 1,150 ml of cyclohexane and 9.0 g of ethyl cellulose (Ethyl Cellulose N-200 of Hercules Co., Ltd.) are placed in the reactor. Then, after a nitrogen gas is blown into the resulting solution to eliminate dissolved oxygens, the solution is heated up to 75° C.

On the other hand, a sodium hydroxide water solution is prepared in another reactor by dissolving 65.8 g of 98 wt % sodium hydroxide in 200 g of ion exchange water. Then, 150 g of acrylic acid is poured into a flask, and the above sodium hydroxide water solution is poured into the flask while the flask is cooled to neturalize the acrylic acid. As a result, a sodium acrylate water solution is produced. The density of sodium acrylate in the resulting water solution is 45 percent by weight.

Then, 0.5 g of potassium persulfate serving as a radical polymerization initiator, and 0.25 g of N,N'-methylenebisacrylamide serving as a crosslinking agent are added to the sodium acrylate water solution. A ratio of potassium persulfate to acrylic acid is 0.1 percent by mole. Subsequently, a nitrogen gas is blown into the sodium acrylate water solution to eliminate dissolved oxygens.

The sodium acrylate water solution is poured into the dropping funnel, so that the sodium acrylate water solution drops into the reactor in an hour and the reactant solution undergoes polymerization. When the dropping ends, the reactant solution is kept at 75° C. and let the same undergo polymerization for another hour. When the reaction ends, cyclohexane is removed under a vacuumed pressure. As a result, a swelling polymer is produced.

Then, the swelling polymer is taken out and dried at 80° C.–100° C. under a vacuumed pressure to produce a dried product, namely, a water absorptive resin for comparison. The water absorption factor and biodegrability of the resulting water absorptive resin are evaluated, in the same manner as EXAMPLE 57, as 38 g/g and 0%, respectively. The result of evaluation is set forth in TABLE 4 below.

COMPARATIVE EXAMPLE 9

Herein, 50 parts by weight of corn starch and 300 parts by weight of water are put into a reactor equipped with a thermometer, a nitrogen gas blowing pipe, and a stirring device. Then, the resulting solution is stirred for an hour at 50° C. under a nitrogen current. Then, after the solution is cooled to 30° C., 20 parts by weight of acrylic acid, 80 parts by weight of sodium acrylate, 0.1 part by weight of ammonium persulfate serving as a radical polymerization initiator, 0.01 part by weight of sodium hydrogen sulfite serving as a reducing agent, and 0.04 part by weight of N,N'-methylenebisacrylamide serving as a crosslinking agent are added to let the reactant undergo polymerization for four hours at temperatures ranging from 30° C. to 80° C. As a result, a polymer of hydrous gel is produced.

Then, the polymer of hydrous gel is taken out and dried with hot air of 120° C. The dried polymer of hydrous gel is ground to produce a water absorptive resin for comparison made of a starch graft polymer.

The water absorption factor and biodegrability of the water absorptive resin are evaluated, in the same manner as EXAMPLE 57, as 20 g/g and 2%, respectively. The result of evaluation is set forth in TABLE 4 below.

TABLE 4

|  | WATER ABSORPTION FACTOR (g/g) | BIODEGRABILITY (%) |
|---|---|---|
| EXAMPLE 57 | 3.6 | 30 |
| EXAMPLE 58 | 31 | 27 |
| EXAMPLE 59 | 41 | 5 |
| EXAMPLE 60 | 50 | 4 |
| EXAMPLE 61 | 23 | 7 |
| EXAMPLE 62 | 32 | 5 |
| COMPARATIVE EXAMPLE 8 | 38 | 0 |
| COMPARATIVE EXAMPLE 9 | 20 | 2 |

TABLE 4 reveals that the water absorptive resins of the present invention render better water absorption factor representing water absorption power and better biodegrability than the comparative counterparts.

The invention being thus described, it will be obvious that the same may be varied in many ways. Such variations are not to be regarded as a departure from the spirit and scope of the invention, and all such modification as would be obvious to one skilled in the art are intended to be included within the scope of the following claims.

What is claimed is:

1. An acrylic ester derivative expressed by:

where $R_1$ represents one of a hydrogen atom and an organic residue, $R_2$ represents one of a hydrogen atom, a counter ion, and an organic residue, and G represents a saccharic residue, wherein said organic residue for each of $R_1$ and $R_2$ is independently selected from the group consisting of a straight-chain, branched chain, or cyclic alkyl group having up to eighteen carbon atoms; a hydroxyalkyl group having up to eight carbon atoms; an alkoxyalkyl group having two to twenty carbon atoms; an alkyl halide group having up to eight carbon atoms; and an aryl group.

2. The acrylic ester derivative as defined in claim 1, wherein $R_1$ represents a hydrogen atom, $R_2$ represents a substitutional group selected from a group consisting of a hydrogen atom, alkaline metal, alkaline earth metal, and an alkyl group having up to eight carbon atoms.

3. The acrylic ester derivative as defined in claim 1, wherein $R_1$ represents a hydrogen atom, $R_2$ represents an alkyl group having up to eight carbon atoms, G represents a saccharic residue selected from a group consisting of glucose, galactose, mannose, glucosamine, N-acetylglucosamine, xylose, ribose, maltose, lactose, chitobiose, maltotriose, cellulose, amylose, chitin, and chitosan.

4. The acrylic ester derivative as defined in claim 1, wherein $R_1$ represents a hydrogen atom, $R_2$ represents an alkyl group having up to eight carbon atoms, and G represents a saccharic residue selected from a group consisting of glucose, galactose, mannose, N-acetylglucosamine, xylose, maltose, lactose, maltotriose, and amylose.

5. The acrylic ester derivative as defined in claim 1, wherein said acrylic ester derivative contains 5 or less percent by weight of impurities having more than one double bond in a single molecule.

6. The acrylic ester derivative as defined in claim 1, wherein a 50 wt % water solution of said acrylic ester derivative has a yellow index of 50 or below.

* * * * *